(12) United States Patent
Achab et al.

(10) Patent No.: US 12,240,867 B2
(45) Date of Patent: Mar. 4, 2025

(54) ARGINASE INHIBITORS AND METHODS OF USE

(71) Applicant: Merck Sharp & Dohme LLC, Rahway, NJ (US)

(72) Inventors: Abdelghani Abe Achab, Melrose, MA (US); Matthew L. Childers, Medfield, MA (US); Jared N. Cumming, Winchester, MA (US); Symon Gathiaka, Waltham, MA (US); Charles A. Lesburg, Waban, MA (US); Derun Li, West Roxbury, MA (US); Min Lu, Brookline, MA (US); Matthew J. Mitcheltree, Jamaica Plain, MA (US); Anandan Palani, Needham, MA (US); Rachel L. Palte, Melrose, MA (US); Hongjun Zhang, Boston, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 751 days.

(21) Appl. No.: 17/312,480

(22) PCT Filed: Dec. 13, 2019

(86) PCT No.: PCT/US2019/066128
§ 371 (c)(1),
(2) Date: Jun. 10, 2021

(87) PCT Pub. No.: WO2020/131598
PCT Pub. Date: Jun. 25, 2020

(65) Prior Publication Data
US 2022/0056051 A1    Feb. 24, 2022

Related U.S. Application Data

(60) Provisional application No. 62/780,990, filed on Dec. 18, 2018.

(51) Int. Cl.
C07F 5/02           (2006.01)
(52) U.S. Cl.
CPC .................................... C07F 5/025 (2013.01)
(58) Field of Classification Search
CPC ................................. C07F 5/025; A61P 35/00
See application file for complete search history.

(56) References Cited

U.S. PATENT DOCUMENTS

| | | | |
|---|---|---|---|
| 8,894,970 B2 | 11/2014 | Tomczuk et al. | |
| 9,233,985 B2 | 1/2016 | Van Zandt et al. | |
| 9,592,221 B2 | 3/2017 | Ebright et al. | |
| 2012/0129806 A1 | 5/2012 | Van Zandt et al. | |
| 2014/0371175 A1 | 12/2014 | Van Zandt et al. | |
| 2017/0319536 A1 | 11/2017 | Blaszczyk et al. | |

FOREIGN PATENT DOCUMENTS

| | | |
|---|---|---|
| WO | 2011133653 A1 | 10/2011 |
| WO | 2012058065 A1 | 5/2012 |
| WO | 2016108707 A1 | 7/2016 |
| WO | 2017075363 A1 | 5/2017 |
| WO | 2017189386 A1 | 11/2017 |
| WO | 2017191130 A2 | 11/2017 |
| WO | 2018119440 A1 | 6/2018 |
| WO | 2019173188 A1 | 9/2019 |
| WO | 2019177873 A1 | 9/2019 |
| WO | 2019245890 A1 | 12/2019 |
| WO | 2020131598 A1 | 6/2020 |

OTHER PUBLICATIONS

Pham, Drug Discovery Today, vol. 23, No. 4, 2018 (Year: 2018).*
Development of OAT-1746: A Novel Arginase 1 and 2 Inhibitor for Cancer Immunotherapy, ESMO 2017 Poster, 2017, 1-1.
Marciniec, Bogdan et al., Ruthenium(II) Complex Catalyzed O-Borylation of Alcohols with Vinylboronates, Synlett, 2009, 2433-2436, 15.
Papadopoulos et al., CX-1158-101: A First-in-Human Phase 1 Study of CB-1158, a Small Molecule Inhibitor of Arginase, as Monotherapy and in Combination with an anti-PD-1 Checkpoint Inhibitor in Patients with Solid Tumors, ASCO Annual Meeting '17, 2017, 1-22.
Public presentation by OncoArendi: ESMO 2017 poster (1 page).
Pubmed Comound Summary for CID 65165396, 2-(Oxolan-2-yl)ethylboronic acid, U.S. National Library of Medicine, Oct. 23, 2019 (Oct. 23, 2012), p. 1-11; p. 2 (https://pubchem.ncbi.nlm.nih.gov/compound/65165396).

(Continued)

Primary Examiner — Susanna Moore
Assistant Examiner — Luisalberto Gonzalez
(74) Attorney, Agent, or Firm — Su Kyung Suh; Anna L. Cocuzzo

(57) ABSTRACT

Described herein are compounds of Formula (I), or a pharmaceutically acceptable salt thereof. The compounds of Formula (I) act as arginase inhibitors and can be useful in preventing, treating or acting as a remedial agent for arginase-related diseases.

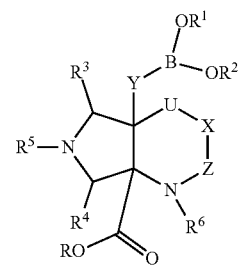

23 Claims, No Drawings

(56) References Cited

OTHER PUBLICATIONS

Pubmed Compound Summary for CID 10654176, 5-Methyl-4-oxaspiro[2,3]hexane, U.S. National Library of Medicine, Oct. 25, 2006 (Oct. 25, 2006), p. 1-12; p. 2 (https://pubchem.ncbi.nlm.nih.gov/compound/10654176).
PUBCHEM-CID: 59894381 Create Date: Aug. 20, 2012 (Aug. 20, 2012) pp. 1-6; p. 2, structure.
International Search Report mailed Feb. 27, 2020 in PCT/US2019/066128 (WO2020131598).

* cited by examiner

ARGINASE INHIBITORS AND METHODS OF USE

CROSS-REFERENCE TO RELATED APPLICATIONS

This application is a U.S. National Phase application under 35 U.S.C. § 371 of PCT Application No. PCT/US19/066128, filed Dec. 13, 2019, which published as WO2020/131598 A1 on Jun. 25, 2020, and claims priority under 35 U.S.C. § 365 (b) from U.S. provisional patent application No. 62/780,990, filed Dec. 18, 2018.

TECHNICAL FIELD

The present invention is directed to arginase inhibitors. Specifically, the arginase inhibitors described herein can be useful in preventing, treating or acting as a remedial agent for arginase-related diseases.

BACKGROUND

Arginase is an enzyme that metabolizes L-arginine to L-ornithine and urea. There are two types of arginase, and they are both products of distinct genes that are regulated independently and located on different chromosomes. Arginase I is a cytosolic protein (34.7 kDa) and is dominant in the liver, but also expressed extrahepatically. Arginase II is a mitochondrial protein and is expressed in kidney, small intestine, brain, monocytes and macrophages.

In addition to its fundamental role in the hepatic urea cycle, arginase also influences the immune systems in humans and mice. Arginase participates in many inflammatory disorders by decreasing the synthesis of nitric oxide and inducing fibrosis and tissue regeneration. L-Arginine deficiency, which is modulated by myeloid cell arginase, suppresses T-cell immune response. This mechanism plays a fundamental role in inflammation-associated immunosuppression.

Arginase expression and L-arginine depletion is also a known immune-suppressive pathway of the mammalian immune system. The depletion of arginine in the tumor microenvironment renders cytotoxic T-cells unable to proliferate and therefore unable to effectively mount an anti-tumor attack. Similarly, M2 macrophages and polymorphonuclear cells (PMNs) express high levels of arginase and may contribute to the local suppression of immune responses. Restoration of arginine levels in the tumor microenvironment via arginase inhibition would be expected to allow T-cell activation and proliferation to occur and result in T-cell mediated anti-tumor responses.

Small-molecule arginase inhibitors are currently described as promising therapeutics for the treatment of several diseases, including allergic asthma, inflammatory bowel disease, ulcerative colitis, cardiovascular diseases (atherosclerosis and hypertension), diseases associated with pathogens (e.g., *Helicobacter pylori*, *Trypanosoma cruzi*, *Leishmania*, *Mycobacterium tuberculosis* and *Salmonella*), cancer and induced or spontaneous immune disorders. Development of potent and specific inhibitors of arginase would be useful for the treatment of diseases where depletion of L-arginine from the microenvironment or induction of arginase pathway is involved in the evasion of anti-tumor immunity, especially for immuno-oncology indications.

SUMMARY

A compound of Formula I:

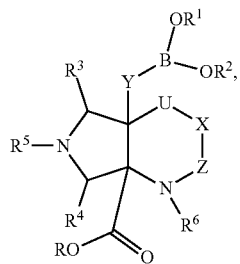

I wherein U, X, Y, Z, R, $R^1$, $R^2$, $R^3$, $R^4$, $R^5$ and $R^6$ are described below.

The compounds described herein are arginase inhibitors, which can be useful in the prevention, treatment or amelioration of diseases where depletion of L-arginine from the microenvironment or induction of arginase pathway is involved in the evasion of anti-tumor immunity, especially for immuno-oncology indications.

Also described herein are methods of treating cancer comprising administering to a patient in need thereof a compound described herein, or a pharmaceutically acceptable salt thereof.

Also described herein are uses of a compound described herein, or a pharmaceutically acceptable salt thereof, to treat cancer in a patient in need thereof.

Also described herein are pharmaceutical compositions comprising a compound described herein, or a pharmaceutically acceptable salt thereof and a pharmaceutically acceptable carrier. Also described herein are pharmaceutical compositions comprising a compound described herein and a pharmaceutically acceptable carrier.

DETAILED DESCRIPTION

Compounds

Described herein are compounds of Formula I:

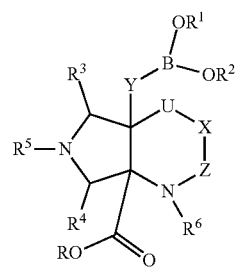

I or a pharmaceutically acceptable salt thereof, wherein:
Y is a straight or branched ($C_2$-$C_5$)alkylenyl, wherein one or more —$CH_2$— groups in Y are optionally and independently replaced with a moiety selected from the group consisting of O, S and NH;
U is $CR^7R^8$ or O;
X is a bond or $CR^9R^{10}$;
Z is a bond or $CR^{11}R^{12}$;
R is hydrogen, $C_1$-$C_6$alkyl, halo$C_1$-$C_6$alkyl, $C_1$-$C_6$alkylOH or $C_1$-$C_6$alkylO$C_1$-$C_6$alkyl;

$R^1$ is hydrogen, $C_3$-$C_6$cycloalkyl or $C_1$-$C_6$alkyl or, taken with $R^2$ forms a $C_3$-$C_8$cycloalkyl, wherein the $C_3$-$C_8$cycloalkyl is unsubstituted or substituted with one to four substituents selected from the group consisting of halogen, $C_1$-$C_6$alkyl, oxo and OH;

$R^2$ is hydrogen, $C_3$-$C_6$cycloalkyl or $C_1$-$C_6$alkyl or, taken with $R^1$ forms a $C_3$-$C_8$cycloalkyl, wherein the $C_3$-$C_8$cycloalkyl is unsubstituted or substituted with one to four substituents selected from the group consisting of halogen, $C_1$-$C_6$alkyl, oxo and OH;

$R^3$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylNH$_2$ or $C_1$-$C_6$alkylOC$_1$-$C_6$alkyl, or when taken with the carbon to which it is attached and the adjacent hydrogen forms C=O;

$R^4$ is hydrogen, $C_1$-$C_6$alkyl, $C_3$-$C_6$cycloalkyl, halo$C_1$-$C_6$alkyl, $C_1$-$C_6$alkylOH, or $C_1$-$C_6$alkylOC$_1$-$C_6$alkyl, or when taken with the carbon to which it is attached and the adjacent hydrogen forms C=O;

$R^5$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylNH$_2$;

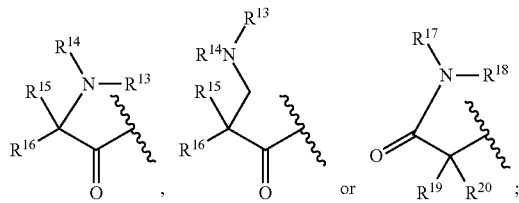

$R^6$ is hydrogen, $C_1$-$C_6$alkyl, $C_3$-$C_6$cycloalkyl, halo$C_1$-$C_6$alkyl, $C_1$-$C_6$alkylOH or $C_1$-$C_6$alkylOC$_1$-$C_6$alkyl;

$R^7$ is hydrogen, $C_1$-$C_6$alkyl, $C_3$-$C_6$cycloalkyl, halo$C_1$-$C_6$alkyl, OH, $C_1$-$C_6$alkylOH, NH$_2$, or $C_1$-$C_6$alkylOC$_1$-$C_6$alkyl, or when taken with $R^8$ forms =O;

$R^8$ is hydrogen, $C_1$-$C_6$alkyl, $C_3$-$C_6$cycloalkyl, halo$C_1$-$C_6$alkyl, OH, $C_1$-$C_6$alkylOH, NH$_2$, or $C_1$-$C_6$alkylOC$_1$-$C_6$alkyl, or when taken with $R^7$ forms =O;

$R^9$ is hydrogen, $C_1$-$C_6$alkyl, $C_3$-$C_6$cycloalkyl, halo$C_1$-$C_6$alkyl, OH, $C_1$-$C_6$alkylOH, $C_1$-$C_6$alkylN($R^{23}$)($R^{24}$) or $C_1$-$C_6$alkylOC$_1$-$C_6$alkyl, or when taken with $R^{10}$ forms =O;

$R^{10}$ is hydrogen, $C_1$-$C_6$alkyl, $C_3$-$C_6$cycloalkyl, halo$C_1$-$C_6$alkyl, OH, $C_1$-$C_6$alkylOH, $C_1$-$C_6$alkylN($R^{23}$)($R^{24}$) or $C_1$-$C_6$alkylOC$_1$-$C_6$alkyl, or when taken with $R^9$ forms =O;

$R^{11}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylN($R^{23}$)($R^{24}$) or $C_1$-$C_6$alkylOC$_1$-$C_6$alkyl, or when taken with $R^{12}$ forms =O;

$R^{12}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylN($R^{23}$)($R^{24}$) or $C_1$-$C_6$alkylOC$_1$-$C_6$alkyl, or when taken with $R^{11}$ forms =O;

$R^{13}$ is hydrogen, $C_1$-$C_6$alkyl, $C_3$-$C_6$cycloalkyl, halo$C_1$-$C_6$alkyl, $C_1$-$C_6$alkylOH, COC$_1$-$C_6$alkylN($R^{21}$)($R^{22}$), or $C_1$-$C_6$alkylOC$_1$-$C_6$alkyl or when taken with $R^{14}$ forms a nitrogen containing heterocycle or when taken with $R^{15}$ or $R^{16}$ forms a nitrogen containing heteroaryl or heterocycle;

$R^{14}$ is hydrogen, $C_1$-$C_6$alkyl, $C_3$-$C_6$cycloalkyl, halo$C_1$-$C_6$alkyl, $C_1$-$C_6$alkylOH, COC$_1$-$C_6$alkylN($R^{21}$)($R^{22}$), or $C_1$-$C_6$alkylOC$_1$-$C_6$alkyl or when taken with $R^{13}$ forms a nitrogen containing heterocycle or when taken with $R^{15}$ or $R^{16}$ forms a nitrogen containing heteroaryl or heterocycle;

$R^{15}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylN($R^{21}$)($R^{22}$), $C_1$-$C_6$alkylCOOR$^{21}$, $C_1$-$C_6$alkylCON($R^{21}$)($R^{22}$), $C_1$-$C_6$alkylSH, $C_1$-$C_6$alkylSC$_1$-$C_6$alkyl or $C_1$-$C_6$alkylOC$_1$-$C_6$alkyl, $C_1$-$C_6$alkylaryl, $C_1$-$C_6$alkylheteroaryl, $C_1$-$C_6$alkylheterocycle or when taken with $R^{13}$ or $R^{14}$ forms a nitrogen containing heterocycle, or when taken with $R^{16}$ forms a $C_3$-$C_7$cycloalkyl or heterocycle;

$R^{16}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylN($R^{21}$)($R^{22}$), $C_1$-$C_6$alkylCOOR$^{21}$, $C_1$-$C_6$alkylCON($R^{21}$)($R^{22}$), $C_1$-$C_6$alkylSH, $C_1$-$C_6$alkylSC$_1$-$C_6$alkyl or $C_1$-$C_6$alkylOC$_1$-$C_6$alkyl, $C_1$-$C_6$alkylaryl, $C_1$-$C_6$alkylheteroaryl, $C_1$-$C_6$alkylheterocycle or when taken with $R^{13}$ or $R^{14}$ forms a nitrogen containing heterocycle, or when taken with $R^{15}$ forms a $C_3$-$C_7$cycloalkyl or heterocycle;

$R^{17}$ is hydrogen, $C_1$-$C_6$alkyl, $C_3$-$C_6$cycloalkyl, halo$C_1$-$C_6$alkyl, OH, $C_1$-$C_6$alkylOH, or $C_1$-$C_6$alkylOC$_1$-$C_6$alkyl or when taken with $R^{18}$ forms a nitrogen containing heterocycle;

$R^{18}$ is hydrogen, $C_1$-$C_6$alkyl, $C_3$-$C_6$cycloalkyl, halo$C_1$-$C_6$alkyl, OH, $C_1$-$C_6$alkylOH, or $C_1$-$C_6$alkylOC$_1$-$C_6$alkyl or when taken with $R^{17}$ forms a nitrogen containing heterocycle;

$R^{19}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylS $C_1$-$C_6$alkyl or $C_1$-$C_6$alkylOC$_1$-$C_6$alkyl;

$R^{20}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylS $C_1$-$C_6$alkyl or $C_1$-$C_6$alkylOC$_1$-$C_6$alkyl;

each occurrence of $R^{21}$ is independently selected from the group consisting of hydrogen, $C_1$-$C_6$alkyl and $C_3$-$C_6$cycloalkyl;

each occurrence of $R^{22}$ is independently selected from the group consisting of hydrogen, $C_1$-$C_6$alkyl and $C_3$-$C_6$cycloalkyl;

each occurrence of $R^{23}$ is independently selected from the group consisting of hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylN($R^{21}$)($R^{22}$), $C_1$-$C_6$alkylCOOR$^{21}$, $C_1$-$C_6$alkylCON($R^{21}$)($R^{22}$), $C_1$-$C_6$alkylSH, $C_1$-$C_6$alkylSC$_1$-$C_6$alkyl, $C_1$-$C_6$alkylOC$_1$-$C_6$alkyl, $C_1$-$C_6$alkylaryl, $C_1$-$C_6$alkylheteroaryl or $C_1$-$C_6$alkylheterocycle; and each occurrence of $R^{24}$ is independently selected from the group consisting of hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylN($R^{21}$)($R^{22}$), $C_1$-$C_6$alkylCOOR$^{21}$, $C_1$-$C_6$alkylCON($R^{21}$)($R^{22}$), $C_1$-$C_6$alkylSH, $C_1$-$C_6$alkylSC$_1$-$C_6$alkyl, $C_1$-$C_6$alkylOC$_1$-$C_6$alkyl, $C_1$-$C_6$alkylaryl, $C_1$-$C_6$alkylheteroaryl or $C_1$-$C_6$alkylheterocycle.

With regard to the compounds described herein, Y is selected from the group consisting of straight or branched ($C_2$-$C_5$)alkylenyl, wherein one or more —CH$_2$— groups in Y are optionally and independently replaced with a moiety selected from the group consisting of O, S and NH. In certain embodiments, Y is ethylenyl, propylenyl, butylenyl or pentylenyl. In certain embodiments Y is propylenyl. In other embodiments, one or more —CH$_2$— groups in Y are optionally and independently replaced with a moiety selected from the group consisting of O, S and NH. In certain embodiments, one —CH2- group in Y is replaced with a moiety selected from the group consisting of O, S and NH. In certain embodiments, Y is (C$_2$-C$_5$)alkylenyl or O—C$_1$-C$_4$alkylenyl,

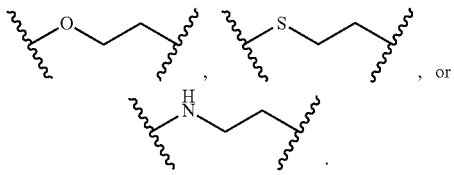

In certain embodiments, Y is

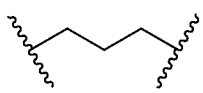

With regard to the compounds described herein, U is CR$^7$R$^8$ or O. In certain embodiments, U is CH$_2$. In certain embodiments, U is O. In certain embodiments, when U is O, X and Z are not bonds.

With regard to the compounds described herein, X is a bond or CR$^9$R$^{10}$. In certain embodiments, X is a bond. In certain embodiments, X is CR$^9$R$^{10}$. In certain embodiments, X is CH$_2$.

With regard to the compounds described herein, Z is a bond or CR$^{11}$R$^{12}$. In certain embodiments, Z is a bond. In certain embodiments, Z is CR$^{11}$R$^{12}$. In certain embodiments, Z is CH$_2$. In certain embodiments, X and Z are not simultaneously bonds.

In certain embodiments, X is CR$^9$R$^{10}$ and Z is a bond. In certain embodiments, U and X are CH$_2$ and Z is a bond, as shown in the compound of Formula II

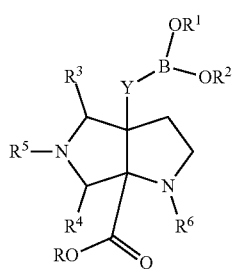

II

With regard to the compounds described herein, R is hydrogen, C$_1$-C$_6$alkyl, haloC$_1$-C$_6$alkyl, C$_1$-C$_6$alkylOH or C$_1$-C$_6$alkylOC$_1$-C$_6$alkyl. In certain embodiments, R is hydrogen. In certain embodiments, R is C$_1$-C$_6$alkyl. Examples of suitable C$_1$-C$_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, R is haloC$_1$-C$_6$alkyl. Suitable haloC$_1$-C$_6$alkyls include but are not limited to, fluoromethyl, difluoromethyl, trifluoromethyl, 2-fluoroethyl, 1,2-difluoroethyl and 2,2-difluoroethyl. In certain embodiments, R is C$_1$-C$_6$alkylOH. Examples of suitable alcohols, include, but are not limited to, hydroxymethyl, hydroxyethyl, hydroxypropyl and hydroxybutyl. In certain embodiments, R is C$_1$-C$_6$alkylOC$_1$-C$_6$alkyl. Suitable C$_1$-C$_6$alkylOC$_1$-C$_6$alkyls include but are not limited to, dimethyl ether, ethyl methyl ether, diethyl ether, dipropyl ether, dibutyl ether and diisopropyl ether.

With regard to the compounds described herein, 1e is hydrogen, C$_3$-C$_6$cycloalkyl or C$_1$-C$_6$alkyl, or when taken with R$^2$, forms a C$_3$-C$_8$cycloalkyl, wherein the C$_3$-C$_8$cycloalkyl is unsubstituted or substituted with one to four substituents selected from the group consisting of halogen, C$_1$-C$_6$alkyl and OH. In certain embodiments, 1e is hydrogen. In certain embodiments, 1e is C$_3$-C$_6$cycloalkyl. Suitable cycloalkyl groups include, but are not limited to, cyclopropyl, cyclobutyl, cyclopentyl, cyclohexyl. In certain embodiments, 1e is C$_1$-C$_6$alkyl. Examples of suitable C$_1$-C$_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, R$^1$ and R$^2$ taken together form a C$_3$-C$_8$cycloalkyl, wherein the C$_3$-C$_8$cycloalkyl is unsubstituted or substituted with one to four substituents selected from the group consisting of halogen, C$_1$-C$_6$alkyl, oxo and OH. In certain embodiments, the C$_3$-C$_8$cycloalkyl is a six or seven-membered carbon ring. In certain embodiments, the C$_3$-C$_8$cycloalkyl is a six or seven-membered, saturated carbon ring. In certain embodiments, the C$_3$-C$_8$cycloalkyl is a bridged ring. In certain embodiments, the C$_3$-C$_8$cycloalkyl is substituted with one substituent selected from the group consisting of halogen, C$_1$-C$_6$alkyl and OH. In certain embodiments, the C$_3$-C$_8$cycloalkyl is substituted with two substituents selected from the group consisting of halogen, C$_1$-C$_6$alkyl and OH. In certain embodiments, the C$_3$-C$_8$cycloalkyl is substituted with three substituents selected from the group consisting of halogen, C$_1$-C$_6$alkyl and OH. In certain embodiments, the C$_3$-C$_8$cycloalkyl is substituted with four substituents selected from the group consisting of halogen, C$_1$-C$_6$alkyl and OH. In certain embodiments, the C$_3$-C$_8$cycloalkyl is substituted with three substituents, wherein all the substituents are C$_1$-C$_6$alkyl groups. In certain embodiments, the C$_3$-C$_8$cycloalkyl is substituted with three substituents, wherein all the substituents are methyl. In certain embodiments, the C$_3$-C$_8$cycloalkyl is substituted with four substituents, wherein all the substituents are C$_1$-C$_6$alkyl groups. In certain embodiments, the C$_3$-C$_8$cycloalkyl is substituted with four substituents, wherein all the substituents are methyl.

In certain embodiments, R$^1$ and R$^2$, when taken together form a C$_3$-C$_8$cycloalkyl selected from the group consisting of:

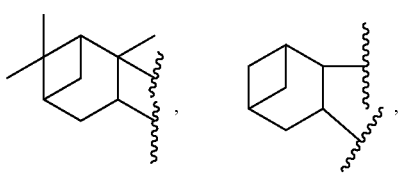

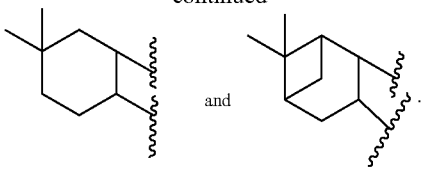

In certain embodiments, $R^1$ and $R^2$ when taken together form the following $C_3$-$C_8$cycloalkyl

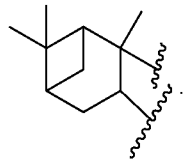 [SMILES: *C1CC2CC(C1(*)C)C2(C)C]

With regard to the compounds described herein, $R^2$ is hydrogen, $C_3$-$C_6$cycloalkyl or $C_1$-$C_6$alkyl, or when taken with R', forms a $C_3$-$C_8$cycloalkyl, wherein the $C_3$-$C_8$cycloalkyl is unsubstituted or substituted with one to four substituents selected from the group consisting of halogen, $C_1$-$C_6$alkyl and OH. In certain embodiments, $R^2$ is hydrogen. In certain embodiments, $R^2$ is $C_3$-$C_6$cycloalkyl. Suitable cycloalkyl groups include, but are not limited to, cyclopropyl, cyclobutyl, cyclopentyl, cyclohexyl. In certain embodiments, $R^2$ is $C_1$-$C_6$alkyl. Examples of suitable $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^2$ when taken with R', forms a $C_3$-$C_8$cycloalkyl, wherein the $C_3$-$C_8$cycloalkyl is unsubstituted or substituted with one to four substituents selected from the group consisting of halogen, $C_1$-$C_6$alkyl, oxo and OH. In certain embodiments, the $C_3$-$C_8$cycloalkyl is a six or seven carbon ring. In certain embodiments, the $C_3$-$C_8$cycloalkyl is a six or seven-membered saturated carbon ring. In certain embodiments, the $C_3$-$C_8$cycloalkyl is a bridged ring. In certain embodiments, the $C_3$-$C_8$cycloalkyl is substituted with one substituent selected from the group consisting of halogen, $C_1$-$C_6$alkyl and OH. In certain embodiments, the $C_3$-$C_8$cycloalkyl is substituted with two substituents selected from the group consisting of halogen, $C_1$-$C_6$alkyl and OH. In certain embodiments, the $C_3$-$C_8$cycloalkyl is substituted with three substituents selected from the group consisting of halogen, $C_1$-$C_6$alkyl and OH. In certain embodiments, the $C_3$-$C_8$cycloalkyl is substituted with four substituents selected from the group consisting of halogen, $C_1$-$C_6$alkyl and OH. In certain embodiments, the $C_3$-$C_8$cycloalkyl is substituted with three substituents, wherein all the substituents are $C_1$-$C_6$alkyl groups. In certain embodiments, the $C_3$-$C_8$cycloalkyl is substituted with three substituents, wherein all the substituents are methyl. In certain embodiments, the $C_3$-$C_8$cycloalkyl is substituted with four substituents, wherein all the substituents are $C_1$-$C_6$alkyl groups. In certain embodiments, the $C_3$-$C_8$cycloalkyl is substituted with four substituents, wherein all the substituents are methyl.

In certain embodiments, $R^1$ and $R^2$, when taken together form a $C_3$-$C_8$cycloalkyl selected from the group consisting of:

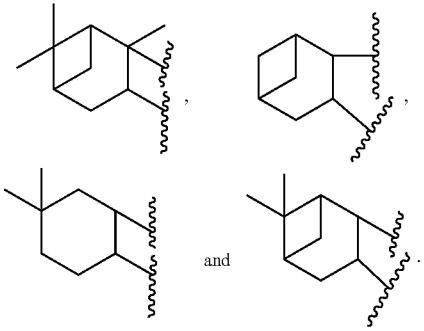

In certain embodiments, $R^1$ and $R^2$ when taken together form the following $C_3$-$C_8$cycloalkyl

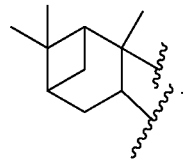 [SMILES: *C1CC2CC(C1(*)C)C2(C)C]

In certain embodiments, $R^1$ and $R^2$ are both hydrogen. In certain embodiments, $R^1$ and $R^2$ are each hydrogen or taken together form a pinane.

With regard to the compounds described herein, $R^3$ is hydrogen, $C_1$-$C_6$alkyl, $C_3$-$C_6$cycloalkyl, halo$C_1$-$C_6$alkyl, $C_1$-$C_6$alkylOH, or $C_1$-$C_6$alkylOC$_1$-$C_6$alkyl, or when taken with the carbon to which it is attached and the adjacent hydrogen forms C=O. In certain embodiments, $R^3$ is hydrogen. In certain embodiments described herein, $R^3$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^3$ is $C_3$-$C_6$cycloalkyl. Suitable cycloalkyl groups include, but are not limited to, cyclopropyl, cyclobutyl, cyclopentyl, cyclohexyl. In certain embodiments, $R^3$ is hydrogen or methyl.

In certain embodiments, $R^3$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^3$ is $C_1$-$C_6$alkylOH. Examples of suitable alcohols, include, but are not limited to, hydroxymethyl, hydroxyethyl, hydroxypropyl and hydroxybutyl. In certain embodiments, $R^3$ is $C_1$-$C_6$alkylNH$_2$. Suitable amines include but are not limited to, —CH$_2$NH$_2$ and CH$_2$CH$_2$NH$_2$. In certain embodiments, $R^3$ is $C_1$-$C_6$alkylOC$_1$-$C_6$alkyl. Suitable $C_1$-$C_6$alkylOC$_1$-$C_6$alkyls include but are not limited to, dimethyl ether, ethyl methyl ether, diethyl ether, dipropyl ether, dibutyl ether and diisopropyl ether.

In certain embodiments, when $R^3$ is taken with the carbon to which it is attached and the adjacent hydrogen $R^3$ forms, C=O.

With regard to the compounds described herein, $R^4$ is hydrogen, $C_1$-$C_6$alkyl, $C_3$-$C_6$cycloalkyl, halo$C_1$-$C_6$alkyl, $C_1$-$C_6$alkylOH, or $C_1$-$C_6$alkylOC$_1$-$C_6$alkyl, or when taken with the carbon to which it is attached and the adjacent hydrogen forms C=O. In certain embodiments, $R^4$ is hydrogen. In certain embodiments described herein, $R^4$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^4$ is $C_3$-$C_6$cycloalkyl. Suitable cycloalkyl groups include, but are not limited to, cyclopropyl, cyclobutyl, cyclopentyl, cyclohexyl. In certain embodiments, $R^4$ is hydrogen or methyl.

In certain embodiments, $R^4$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^4$ is $C_1$-$C_6$alkylOH. Examples of suitable alcohols, include, but are not limited to, hydroxymethyl, hydroxyethyl, hydroxypropyl and hydroxybutyl. In certain embodiments, $R^4$ is $C_1$-$C_6$alkylOC$_1$-$C_6$alkyl. Suitable $C_1$-$C_6$alkylOC$_1$-$C_6$alkyls include but are not limited to, dimethyl ether, ethyl methyl ether, diethyl ether, dipropyl ether, dibutyl ether and diisopropyl ether.

In certain embodiments, when $R^4$ is taken with the carbon to which it is attached and the adjacent hydrogen $R^4$ forms, C=O.

With regard to the compounds described herein, $R^5$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylNH$_2$;

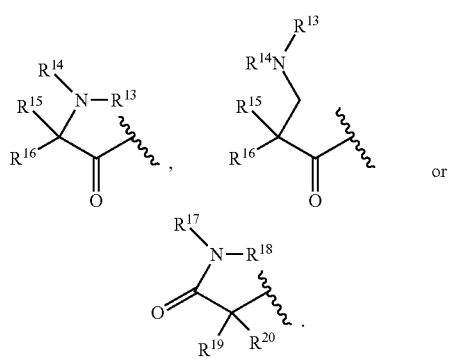

In certain embodiments described herein, $R^5$ is hydrogen. In certain embodiments described herein, $R^5$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^5$ is methyl. In certain embodiments, $R^5$ is $C_3$-$C_6$cycloalkyl. Suitable cycloalkyl groups include, but are not limited to, cyclopropyl, cyclobutyl, cyclopentyl, cyclohexyl.

In certain embodiments, $R^5$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^5$ is $C_1$-$C_6$alkylOH. Examples of suitable alcohols, include, but are not limited to, hydroxymethyl, hydroxyethyl, hydroxypropyl and hydroxybutyl. In certain embodiments, $R^5$ is $C_1$-$C_6$alkylNH$_2$.

In certain embodiments, $R^5$ is:

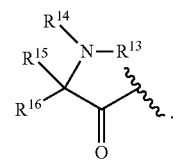

In certain embodiments, $R^5$ is:

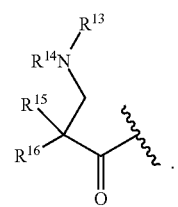

In certain embodiments, $R^5$ is:

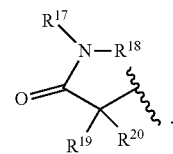

With regard to the compounds described herein, $R^6$ is hydrogen, $C_1$-$C_6$alkyl, $C_3$-$C_6$cycloalkyl, halo$C_1$-$C_6$alkyl, $C_1$-$C_6$alkylOH or $C_1$-$C_6$alkylOC$_1$-$C_6$alkyl.

In certain embodiments, $R^6$ is hydrogen. In certain embodiments described herein, $R^6$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^6$ is $C_3$-$C_6$cycloalkyl. Suitable cycloalkyl groups include, but are not limited to, cyclopropyl, cyclobutyl, cyclopentyl, cyclohexyl.

In certain embodiments, $R^6$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^6$ is $C_1$-$C_6$alkylOH. Examples of suitable alcohols, include, but are not limited to, hydroxymethyl, hydroxyethyl, hydroxypropyl and hydroxybutyl. In certain embodiments, $R^6$ is $C_1$-$C_6$alkylO$C_1$-$C_6$alkyl. Suitable $C_1$-$C_6$alkylO$C_1$-$C_6$alkyls include but are not limited to, dimethyl ether, ethyl methyl ether, diethyl ether, dipropyl ether, dibutyl ether and diisopropyl ether.

With regard to the compounds described herein, $R^7$ is hydrogen, $C_1$-$C_6$alkyl, $C_3$-$C_6$cycloalkyl, halo$C_1$-$C_6$alkyl, OH, $C_1$-$C_6$alkylOH, $NH_2$, or $C_1$-$C_6$alkylO$C_1$-$C_6$alkyl, or when taken with $R^8$ forms =O.

In certain embodiments described herein, $R^7$ is hydrogen. In certain embodiments described herein, $R^7$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^7$ is $C_3$-$C_6$cycloalkyl. Suitable cycloalkyl groups include, but are not limited to, cyclopropyl, cyclobutyl, cyclopentyl, cyclohexyl.

In certain embodiments, $R^7$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^7$ is OH. In certain embodiments, $R^7$ is $C_1$-$C_6$alkylOH. Examples of suitable alcohols, include, but are not limited to, hydroxymethyl, hydroxyethyl, hydroxypropyl and hydroxybutyl. In certain embodiments, $R^7$ is $NH_2$. In certain embodiments, $R^7$ is $C_1$-$C_6$alkylO$C_1$-$C_6$alkyl. Suitable $C_1$-$C_6$alkylO$C_1$-$C_6$alkyls include but are not limited to, dimethyl ether, ethyl methyl ether, diethyl ether, dipropyl ether, dibutyl ether and diisopropyl ether. In certain embodiments, $R^7$, when taken with $R^8$, forms an oxo group (=O).

With regard to the compounds described herein, $R^8$ is hydrogen, $C_1$-$C_6$alkyl, $C_3$-$C_6$cycloalkyl, halo$C_1$-$C_6$alkyl, OH, $C_1$-$C_6$alkylOH, $NH_2$, or $C_1$-$C_6$alkylO$C_1$-$C_6$alkyl, or when taken with $R^7$, forms =O.

In certain embodiments described herein, $R^8$ is hydrogen. In certain embodiments described herein, $R^8$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^8$ is $C_3$-$C_6$cycloalkyl. Suitable cycloalkyl groups include, but are not limited to, cyclopropyl, cyclobutyl, cyclopentyl, cyclohexyl.

In certain embodiments, $R^8$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^8$ is OH. In certain embodiments, $R^8$ is $C_1$-$C_6$alkylOH. Examples of suitable alcohols, include, but are not limited to, hydroxymethyl, hydroxyethyl, hydroxypropyl and hydroxybutyl. In certain embodiments, $R^8$ is $NH_2$. In certain embodiments, $R^8$ is $C_1$-$C_6$alkylO$C_1$-$C_6$alkyl. Suitable $C_1$-$C_6$alkylO$C_1$-$C_6$alkyls include but are not limited to, dimethyl ether, ethyl methyl ether, diethyl ether, dipropyl ether, dibutyl ether and diisopropyl ether. In certain embodiments, $R^8$, when taken with $R^7$, forms an oxo group (=O).

With regard to the compounds described herein, $R^9$ is hydrogen, $C_1$-$C_6$alkyl, $C_3$-$C_6$cycloalkyl, halo$C_1$-$C_6$alkyl, OH, $C_1$-$C_6$alkylOH, $C_1$-$C_6$alkylN($R^{23}$)($R^{24}$) or $C_1$-$C_6$alkylO$C_1$-$C_6$alkyl, or when taken with $R^{10}$ forms =O.

In certain embodiments described herein, $R^9$ is hydrogen. In certain embodiments described herein, $R^9$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^9$ is $C_3$-$C_6$cycloalkyl. Suitable cycloalkyl groups include, but are not limited to, cyclopropyl, cyclobutyl, cyclopentyl, cyclohexyl.

In certain embodiments, $R^9$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^9$ is OH. In certain embodiments, $R^9$ is $C_1$-$C_6$alkylOH. Examples of suitable alcohols, include, but are not limited to, hydroxymethyl, hydroxyethyl, hydroxypropyl and hydroxybutyl. In certain embodiments, $R^9$ is $C_1$-$C_6$alkylN($R^{23}$)($R^{24}$). Suitable $C_1$-$C_6$alkylN($R^{23}$)($R^{24}$)s include but are not limited to, $CH_2NH_2$ and $CH_2N(CH_3)_2$. In certain embodiments, $R^9$ is $C_1$-$C_6$alkylO$C_1$-$C_6$alkyl. Suitable $C_1$-$C_6$alkylO$C_1$-$C_6$alkyls include but are not limited to, dimethyl ether, ethyl methyl ether, diethyl ether, dipropyl ether, dibutyl ether and diisopropyl ether. In certain embodiments, $R^9$, when taken with $R^m$, forms an oxo group (=O).

In certain embodiments, if Z is a bond, then $R^9$ is not OH.

With regard to the compounds described herein, $R^{10}$ is hydrogen, $C_1$-$C_6$alkyl, $C_3$-$C_6$cycloalkyl, halo$C_1$-$C_6$alkyl, OH, $C_1$-$C_6$alkylOH, $C_1$-$C_6$alkylN($R^{23}$)($R^{24}$) or $C_1$-$C_6$alkylO$C_1$-$C_6$alkyl, or when taken with $R^9$ forms =O.

In certain embodiments described herein, $R^{10}$ is hydrogen. In certain embodiments described herein, $10°$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $10°$ is methyl. In certain embodiments, $10°$ is $C_3$-$C_6$cycloalkyl. Suitable cycloalkyl groups include, but are not limited to, cyclopropyl, cyclobutyl, cyclopentyl, cyclohexyl.

In certain embodiments, $R^{10}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{10}$ is OH. In certain embodiments, $R^{10}$ is $C_1$-$C_6$alkylOH. Examples of suitable alcohols, include, but are not limited to, hydroxymethyl, hydroxyethyl, hydroxypropyl and hydroxybutyl. In certain embodiments, $10°$ is ethanol. In certain embodiments, $R^{10}$ is $C_6$alkylN($R^{23}$)($R^{24}$). Suitable $C_1$-$C_6$alkylN($R^{23}$)($R^{24}$)s include but are not limited to, $CH_2NH_2$ and $CH_2N(CH_3)_2$. In certain embodiments, $R^{10}$ is $C_1$-$C_6$alkylO$C_1$-$C_6$alkyl. Suitable $C_1$-$C_6$alkylO$C_1$-$C_6$alkyls include but are not limited to, dimethyl ether, ethyl methyl ether, diethyl ether, dipropyl ether, dibutyl ether and diisopropyl ether. In certain embodiments, $R^m$, when taken with $R^9$, forms an oxo group (=O). In certain embodiments, $R^{10}$ is hydrogen, methyl or ethanol.

In certain embodiments, if Z is a bond, then $R^{10}$ is not OH.

With regard to the compounds described herein, $R^{11}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylN($R^{23}$)($R^{24}$) or $C_1$-$C_6$alkylO$C_1$-$C_6$alkyl, or when taken with $R^{12}$ forms =O.

In certain embodiments described herein, $R^{11}$ is hydrogen. In certain embodiments described herein, $R^{11}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{11}$ is $C_3$-$C_6$cycloalkyl. Suitable cycloalkyl groups include, but are not limited to, cyclopropyl, cyclobutyl, cyclopentyl, cyclohexyl.

In certain embodiments, $R^{11}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{11}$ is $C_1$-$C_6$alkylOH. Examples of suitable alcohols, include, but are not limited to, hydroxymethyl, hydroxyethyl, hydroxypropyl and hydroxybutyl. In certain embodiments, $R^{11}$ is $C_1$-$C_6$alkylN($R^{23}$)($R^{24}$). Suitable $C_1$-$C_6$alkylN($R^{23}$)($R^{24}$)s include but are not limited to, $CH_2NH_2$ and $CH_2N(CH_3)_2$. In certain embodiments, $R^{11}$ is $C_1$-$C_6$alkylO$C_1$-$C_6$alkyl. Suitable $C_1$-$C_6$alkylO$C_1$-$C_6$alkyls include but are not limited to, dimethyl ether, ethyl methyl ether, diethyl ether, dipropyl ether, dibutyl ether and diisopropyl ether. In certain embodiments, $R^{11}$, when taken with $R^{12}$, forms an oxo group (=O).

With regard to the compounds described herein, $R^{12}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylN($R^{23}$)($R^{24}$) or $C_1$-$C_6$alkylO$C_1$-$C_6$alkyl, or when taken with $R^{11}$, forms =O.

In certain embodiments described herein, $R^{12}$ is hydrogen. In certain embodiments described herein, $R^{12}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{12}$ is $C_3$-$C_6$cycloalkyl. Suitable cycloalkyl groups include, but are not limited to, cyclopropyl, cyclobutyl, cyclopentyl, cyclohexyl.

In certain embodiments, $R^{12}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{12}$ is $C_1$-$C_6$alkylOH. Examples of suitable alcohols, include, but are not limited to, hydroxymethyl, hydroxyethyl, hydroxypropyl and hydroxybutyl. In certain embodiments, $R^{12}$ is $C_1$-$C_6$alkylN($R^{23}$)($R^{24}$). Suitable $C_1$-$C_6$alkylN($R^{23}$)($R^{24}$)s include but are not limited to, $CH_2NH_2$ and $CH_2N(CH_3)_2$. In certain embodiments, $R^{12}$ is $C_1$-$C_6$alkylO$C_1$-$C_6$alkyl. Suitable $C_1$-$C_6$alkylO$C_1$-$C_6$alkyls include but are not limited to, dimethyl ether, ethyl methyl ether, diethyl ether, dipropyl ether, dibutyl ether and diisopropyl ether. In certain embodiments, $R^{12}$, when taken with $R^{11}$, forms an oxo group (=O).

With regard to the compounds described herein, $R^{13}$ is hydrogen, $C_1$-$C_6$alkyl, $C_3$-$C_6$cycloalkyl, halo$C_1$-$C_6$alkyl, $C_1$-$C_6$alkylOH, $COC_1$-$C_6$alkylN($R^{21}$)($R^{22}$), or $C_1$-$C_6$alkylO$C_1$-$C_6$alkyl or when taken with $R^{14}$, forms a nitrogen containing heterocycle or when taken with $R^{15}$ or $R^{16}$ forms a nitrogen containing heteroaryl or heterocycle.

In certain embodiments, $R^{13}$ is hydrogen. In certain embodiments described herein, $R^{13}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{13}$ is $C_3$-$C_6$cycloalkyl. Suitable cycloalkyl groups include, but are not limited to, cyclopropyl, cyclobutyl, cyclopentyl, cyclohexyl.

In certain embodiments, $R^{13}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{13}$ is $C_1$-$C_6$alkylOH. Examples of suitable alcohols, include, but are not limited to, hydroxymethyl, hydroxyethyl, hydroxypropyl and hydroxybutyl. In certain embodiments, $R^{13}$ is $COC_1$-$C_6$alkylN($R^{21}$)($R^{22}$). In certain embodiments, $R^{13}$ is $C_1$-$C_6$alkylO$C_1$-$C_6$alkyl. Suitable $C_1$-$C_6$alkylO$C_1$-$C_6$alkyls include but are not limited to, dimethyl ether, ethyl methyl ether, diethyl ether, dipropyl ether, dibutyl ether and diisopropyl ether.

In certain embodiments, $R^{13}$, when taken with $R^{14}$, forms a nitrogen containing heterocycle.

In certain embodiments, $R^{13}$, when taken with $R^{15}$ or $R^{16}$, forms a nitrogen containing heteroaryl or heterocycle. In certain embodiments, $R^{13}$, when taken with $R^{15}$, forms a nitrogen containing heteroaryl or heterocycle. In certain embodiments, $R^{13}$, when taken with $R^{16}$, forms a nitrogen containing heteroaryl or heterocycle. Suitable include, but are not limited to, pyridyl (pyridinyl), imidazolyl, triazolyl, triazinyl, pyrimidyl, pyridazinyl, indolizinyl, cinnolinyl, phthalazinyl, quinazolinyl, naphthyridinyl, quinoxalinyl, purinyl, benzimidazolyl, quinolyl, isoquinolyl.

Suitable heterocycles include, but are not limited to, mono- or bicyclic or bridged partially unsaturated and saturated rings containing at least one nitrogen, each of said ring having from 3 to 10 atoms in which the point of attachment may be carbon or nitrogen. Examples include tetrahydropyranyl, pyrrolidinyl, piperidinyl, piperazinyl, imidazolidinyl, 2,3-dihydrofuro(2,3-b)pyridyl, isoindolinyl, tetrahydropyran, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

With regard to the compounds described herein, $R^{14}$ is hydrogen, $C_1$-$C_6$alkyl, $C_3$-$C_6$cycloalkyl, halo$C_1$-$C_6$alkyl, $C_1$-$C_6$alkylOH, $COC_1$-$C_6$alkylN($R^{21}$)($R^{22}$), or $C_1$-$C_6$alkylO$C_1$-$C_6$alkyl or when taken with $R^{13}$, forms a nitrogen containing heterocycle or when taken with $R^{15}$ or $R^{16}$, forms a nitrogen containing heteroaryl or heterocycle.

In certain embodiments, $R^{14}$ is hydrogen. In certain embodiments described herein, $R^{14}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{14}$ is $C_3$-$C_6$cycloalkyl. Suitable cycloalkyl groups include, but are not limited to, cyclopropyl, cyclobutyl, cyclopentyl, cyclohexyl.

In certain embodiments, $R^{14}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{14}$ is $C_1$-$C_6$alkylOH. Examples of suitable alcohols, include, but are not limited to, hydroxymethyl, hydroxyethyl, hydroxypropyl and hydroxybutyl. In certain embodiments, $R^{14}$ is COC$_1$-$C_6$alkylN($R^{21}$)($R^{22}$). In certain embodiments, $R^{14}$ is $C_1$-$C_6$alkylOC$_1$-$C_6$alkyl. Suitable $C_1$-$C_6$alkylOC$_1$-$C_6$alkyls include but are not limited to, dimethyl ether, ethyl methyl ether, diethyl ether, dipropyl ether, dibutyl ether and diisopropyl ether.

In certain embodiments, $R^{14}$, when taken with $R^{13}$, forms a nitrogen containing heterocycle or when taken with $R^{15}$ or $R^{16}$ forms a nitrogen containing heteroaryl or heterocycle. In certain embodiments, $R^{14}$ when taken with $R^{13}$, forms a nitrogen containing heterocycle. In certain embodiments, $R^{14}$, when taken with $R^{15}$, forms a nitrogen containing heteroaryl or heterocycle. In certain embodiments, $R^{14}$, when taken with $R^{16}$, forms a nitrogen containing heteroaryl or heterocycle. Suitable heteroaryls include, but are not limited to, pyridyl (pyridinyl), imidazolyl, triazolyl, triazinyl, pyrimidyl, pyridazinyl, indolizinyl, cinnolinyl, phthalazinyl, quinazolinyl, naphthyridinyl, quinoxalinyl, purinyl, benzimidazolyl, quinolyl, isoquinolyl.

Suitable heterocycles include, but are not limited to, mono- or bicyclic or bridged partially unsaturated and saturated rings containing at least one nitrogen, each of said ring having from 3 to 10 atoms in which the point of attachment may be carbon or nitrogen. Examples include tetrahydropyranyl, pyrrolidinyl, piperidinyl, piperazinyl, imidazolidinyl, 2,3-dihydrofuro(2,3-b)pyridyl, isoindolinyl, tetrahydropyran, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

With regard to the compounds described herein, $R^{15}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylN($R^{21}$)($R^{22}$), $C_1$-$C_6$alkylCOOR$^{21}$, $C_1$-$C_6$alkylCON($R^{21}$)($R^{22}$), $C_1$-$C_6$alkylSH, $C_1$-$C_6$alkylSC$_1$-$C_6$alkyl or $C_1$-$C_6$alkylOC$_1$-$C_6$alkyl, $C_1$-$C_6$alkylaryl, $C_1$-$C_6$alkylheteroaryl, $C_1$-$C_6$alkylheterocycle, or when taken with $R^{13}$ or $R^{14}$, forms a nitrogen containing heteroaryl or heterocycle, or when taken with $R^{16}$, forms a $C_3$-$C_7$cycloalkyl or heterocycle.

In certain embodiments, $R^{15}$ is hydrogen. In certain embodiments described herein, $R^{15}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{15}$ is $C_3$-$C_6$cycloalkyl. Suitable cycloalkyl groups include, but are not limited to, cyclopropyl, cyclobutyl, cyclopentyl, cyclohexyl.

In certain embodiments, $R^{15}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{15}$ is $C_1$-$C_6$alkylOH. Examples of suitable alcohols, include, but are not limited to, hydroxymethyl, hydroxyethyl, hydroxypropyl and hydroxybutyl. In certain embodiments, $R^{15}$ is COC$_1$-$C_6$alkylN($R^{21}$)($R^{22}$). In certain embodiments, $R^{15}$ is $C_1$-$C_6$alkylOC$_1$-$C_6$alkyl. Suitable $C_1$-$C_6$alkylOC$_1$-$C_6$alkyls include but are not limited to, dimethyl ether, ethyl methyl ether, diethyl ether, dipropyl ether, dibutyl ether and diisopropyl ether.

In certain embodiments, $R^{15}$ is $C_1$-$C_6$alkylCOOR$^{21}$. In certain embodiments, $R^{15}$ is $C_1$-$C_6$alkylCON($R^{21}$)($R^{22}$). Examples of suitable COC$_1$-$C_6$alkylN($R^{21}$)($R^{22}$) groups include, but are not limited to, COCH$_2$NH$_2$, COCH$_2$NH(CH$_3$), COCH$_2$N(CH$_3$)$_2$ and COCH$_2$CH$_2$N(CH$_3$)$_2$. In certain embodiments, $R^{15}$ is $C_1$-$C_6$alkylSH. In certain embodiments, $R^{15}$ is $C_1$-$C_6$alkylSC$_1$-$C_6$alkyl. In certain embodiments, $R^{15}$ is $C_1$-$C_6$alkylOC$_1$-$C_6$alkyl. In certain embodiments, $R^{15}$ is $C_1$-$C_6$alkylaryl. In certain embodiments, $R^{15}$ is $C_1$-$C_6$alkylheteroaryl. In certain embodiments, $R^{15}$ is $C_1$-$C_6$alkylaryl. In certain embodiments, $R^{15}$ is $C_1$-$C_6$alkylheterocycle. In certain embodiments, $R^{15}$ is when taken with $R^{13}$ or $R^{14}$, forms a nitrogen containing heteroaryl or heterocycle, or when taken with $R^{16}$, forms a $C_3$-$C_7$cycloalkyl or heterocycle.

In certain embodiments, $R^{15}$, when taken with $R^{13}$ or $R^{14}$, forms a nitrogen containing heteroaryl or heterocycle. In certain embodiments, $R^{15}$, when taken with $R^{13}$ and $R^{14}$, forms a nitrogen containing heteroaryl or heterocycle. In certain embodiments, $R^{15}$, when taken with $R^{14}$, forms a nitrogen containing heteroaryl or heterocycle. Suitable heteroaryls include, but are not limited to, pyridyl (pyridinyl), imidazolyl, triazolyl, triazinyl, pyrimidyl, pyridazinyl, indolizinyl, cinnolinyl, phthalazinyl, quinazolinyl, naphthyridinyl, quinoxalinyl, purinyl, benzimidazolyl, quinolyl, isoquinolyl.

With regard to the compounds described herein, $R^{16}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylN($R^{21}$)($R^{22}$), $C_1$-$C_6$alkylCOOR$^{21}$, $C_1$-$C_6$alkylCON($R^{21}$)($R^{22}$), $C_1$-$C_6$alkylSH, $C_1$-$C_6$alkylSC$_1$-$C_6$alkyl or $C_1$-$C_6$alkylOC$_1$-$C_6$alkyl, $C_1$-$C_6$alkylaryl, $C_1$-$C_6$alkylheteroaryl, $C_1$-$C_6$alkylheterocycle or when taken with $R^{13}$ or $R^{14}$, forms a nitrogen containing heteroaryl or heterocycle, or when taken with $R^{15}$, forms a $C_3$-$C_7$cycloalkyl or heterocycle.

In certain embodiments, $R^{16}$ is hydrogen. In certain embodiments described herein, $R^{16}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{16}$ is methyl. In certain embodiments, $R^{16}$ is isopropyl. In certain embodiments, $R^{16}$ is isobutyl. In certain embodiments, $R^{16}$ is tertbutyl. In certain embodiments, $R^{16}$ is $C_3$-$C_6$cycloalkyl.

Suitable cycloalkyl groups include, but are not limited to, cyclopropyl, cyclobutyl, cyclopentyl, cyclohexyl.

In certain embodiments, $R^{16}$ is haloC$_1$-C$_6$alkyl. Suitable haloC$_1$-C$_6$alkyls include but are not limited to, fluoromethyl, difluoromethyl, trifluoromethyl, 2-fluoroethyl, 1,2-difluoroethyl and 2,2-difluoroethyl. In certain embodiments, $R^{16}$ is C$_1$-C$_6$alkylOH. Examples of suitable alcohols, include, but are not limited to, hydroxymethyl, hydroxyethyl, hydroxypropyl and hydroxybutyl. In certain embodiments, $R^{16}$ is COC$_1$-C$_6$alkylN($R^{21}$)($R^{22}$). In certain embodiments, $R^{16}$ is C$_1$-C$_6$alkylOC$_1$-C$_6$alkyl. Suitable C$_1$-C$_6$alkylOC$_1$-C$_6$alkyls include but are not limited to, dimethyl ether, ethyl methyl ether, diethyl ether, dipropyl ether, dibutyl ether and diisopropyl ether.

In certain embodiments, $R^{16}$ is C$_1$-C$_6$alkylCOOR$^{21}$. In certain embodiments, $R^{16}$ is C$_1$-C$_6$alkylCON($R^{21}$)($R^{22}$). Examples of suitable COC$_1$-C$_6$alkylN($R^{21}$)($R^{22}$) groups include, but are not limited to, COCH$_2$NH$_2$, COCH$_2$NH (CH$_3$), COCH$_2$N(CH$_3$)$_2$ and COCH$_2$CH$_2$N(CH$_3$)$_2$. In certain embodiments, $R^{16}$ is C$_1$-C$_6$alkylSH. In certain embodiments, $R^{16}$ is C$_1$-C$_6$alkylSC$_1$-C$_6$alkyl. In certain embodiments, $R^{16}$ is C$_1$-C$_6$alkylOC$_1$-C$_6$alkyl. In certain embodiments, $R^{16}$ is C$_1$-C$_6$alkylaryl. In certain embodiments, $R^{16}$ is C$_1$-C$_6$alkylheteroaryl. In certain embodiments, $R^{16}$ is C$_1$-C$_6$alkylheterocycle. In certain embodiments, $R^{16}$ is when taken with $R^{13}$ or $R^{14}$, forms a nitrogen containing heteroaryl or heterocycle, or when taken with $R^{15}$, forms a C$_3$-C$_7$cycloalkyl or heterocycle.

In certain embodiments, $R^{16}$, when taken with $R^{13}$ or $R^{14}$, forms a nitrogen containing heteroaryl or heterocycle. In certain embodiments, $R^{16}$, when taken with $R^{13}$ and $R^{14}$, forms a nitrogen containing heteroaryl or heterocycle. In certain embodiments, $R^{16}$, when taken with $R^{14}$, forms a nitrogen containing heteroaryl or heterocycle. Suitable heteroaryls include, but are not limited to, pyridyl (pyridinyl), imidazolyl, triazolyl, triazinyl, pyrimidyl, pyridazinyl, indolizinyl, cinnolinyl, phthalazinyl, quinazolinyl, naphthyridinyl, quinoxalinyl, purinyl, benzimidazolyl, quinolyl, isoquinolyl.

With regard to the compounds described herein, $R^{17}$ is hydrogen, C$_1$-C$_6$alkyl, C$_3$-C$_6$cycloalkyl, haloC$_1$-C$_6$alkyl, OH, C$_1$-C$_6$alkylOH, or C$_1$-C$_6$alkylOC$_1$-C$_6$alkyl or when taken with $R^{18, \text{forms}}$ a nitrogen containing heterocycle.

In certain embodiments, $R^{17}$ is hydrogen. In certain embodiments described herein, $R^{17}$ is C$_1$-C$_6$alkyl. Examples of suitable C$_1$-C$_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{17}$ is C$_3$-C$_6$cycloalkyl. Suitable cycloalkyl groups include, but are not limited to, cyclopropyl, cyclobutyl, cyclopentyl, cyclohexyl.

In certain embodiments, $R^{17}$ is haloC$_1$-C$_6$alkyl. Suitable haloC$_1$-C$_6$alkyls include but are not limited to, fluoromethyl, difluoromethyl, trifluoromethyl, 2-fluoroethyl, 1,2-difluoroethyl and 2,2-difluoroethyl. In certain embodiments, $R^{17}$ is OH. In certain embodiments, $R^{17}$ is C$_1$-C$_6$alkylOH. Examples of suitable alcohols, include, but are not limited to, hydroxymethyl, hydroxyethyl, hydroxypropyl and hydroxybutyl. In certain embodiments, $R^{17}$ is C$_1$-C$_6$alkylOC$_1$-C$_6$alkyl. Suitable C$_1$-C$_6$alkylOC$_1$-C$_6$alkyls include but are not limited to, dimethyl ether, ethyl methyl ether, diethyl ether, dipropyl ether, dibutyl ether and diisopropyl ether.

In certain embodiments, $R^{17}$, when taken with $R^{18}$, forms a nitrogen containing heterocycle. Suitable heterocycles include, but are not limited to, mono- or bicyclic or bridged partially unsaturated and saturated rings containing at least one nitrogen, each of said ring having from 3 to 10 atoms in which the point of attachment may be carbon or nitrogen. Examples include tetrahydropyranyl, pyrrolidinyl, piperidinyl, piperazinyl, imidazolidinyl, 2,3-dihydrofuro(2,3-b)pyridyl, isoindolinyl, tetrahydropyran, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

With regard to the compounds described herein, $R^{18}$ is hydrogen, C$_1$-C$_6$alkyl, C$_3$-C$_6$cycloalkyl, haloC$_1$-C$_6$alkyl, OH, C$_1$-C$_6$alkylOH, or C$_1$-C$_6$alkylOC$_1$-C$_6$alkyl or when taken with $R^{17}$, forms a nitrogen containing heterocycle.

In certain embodiments, $R^{18}$ is hydrogen. In certain embodiments described herein, $R^{18}$ is C$_1$-C$_6$alkyl. Examples of suitable C$_1$-C$_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{18}$ is C$_3$-C$_6$cycloalkyl. Suitable cycloalkyl groups include, but are not limited to, cyclopropyl, cyclobutyl, cyclopentyl, cyclohexyl.

In certain embodiments, $R^{18}$ is haloC$_1$-C$_6$alkyl. Suitable haloC$_1$-C$_6$alkyls include but are not limited to, fluoromethyl, difluoromethyl, trifluoromethyl, 2-fluoroethyl, 1,2-difluoroethyl and 2,2-difluoroethyl. In certain embodiments, $R^{18}$ is OH. In certain embodiments, $R^{18}$ is C$_1$-C$_6$alkylOH. Examples of suitable alcohols, include, but are not limited to, hydroxymethyl, hydroxyethyl, hydroxypropyl and hydroxybutyl. In certain embodiments, $R^{18}$ is C$_1$-C$_6$alkylOC$_1$-C$_6$alkyl. Suitable C$_1$-C$_6$alkylOC$_1$-C$_6$alkyls include but are not limited to, dimethyl ether, ethyl methyl ether, diethyl ether, dipropyl ether, dibutyl ether and diisopropyl ether.

In certain embodiments, $R^{18}$, when taken with $R^{17}$, forms a nitrogen containing heterocycle. Suitable heterocycles include, but are not limited to, include mono- or bicyclic or bridged partially unsaturated and saturated rings containing at least one nitrogen, each of said ring having from 3 to 10 atoms in which the point of attachment may be carbon or nitrogen. Examples include tetrahydropyranyl, pyrrolidinyl, piperidinyl, piperazinyl, imidazolidinyl, 2,3-dihydrofuro(2, 3-b)pyridyl, isoindolinyl, tetrahydropyran, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

With regard to the compounds described herein, $R^{19}$ is hydrogen, C$_1$-C$_6$alkyl, C$_3$-C$_6$cycloalkyl, haloC$_1$-C$_6$alkyl, C$_1$-C$_6$alkylOH, C$_1$-C$_6$alkylS C$_1$-C$_6$alkyl or C$_1$-C$_6$alkylOC$_1$-C$_6$alkyl. In certain embodiments, $R^{19}$ is hydrogen. In certain embodiments described herein, $R^{19}$ is C$_1$-C$_6$alkyl. Examples of suitable C$_1$-C$_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{19}$ is $C_3$-$C_6$cycloalkyl. Suitable cycloalkyl groups include, but are not limited to, cyclopropyl, cyclobutyl, cyclopentyl, cyclohexyl.

In certain embodiments, $R^{19}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{19}$ is $C_1$-$C_6$alkylS $C_1$-$C_6$alkyl. In certain embodiments, $R^{19}$ is $C_1$-$C_6$alkylOH. Examples of suitable alcohols, include, but are not limited to, hydroxymethyl, hydroxyethyl, hydroxypropyl and hydroxybutyl. In certain embodiments, $R^{19}$ is $C_1$-$C_6$alkylO$C_1$-$C_6$alkyl. Suitable $C_1$-$C_6$alkylO$C_1$-$C_6$alkyls include but are not limited to, dimethyl ether, ethyl methyl ether, diethyl ether, dipropyl ether, dibutyl ether and diisopropyl ether.

With regard to the compounds described herein, $R^{20}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylS $C_1$-$C_6$alkyl or $C_1$-$C_6$alkylO$C_1$-$C_6$alkyl. In certain embodiments, $R^{20}$ is hydrogen. In certain embodiments described herein, $R^{20}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{20}$ is $C_3$-$C_6$cycloalkyl. Suitable cycloalkyl groups include, but are not limited to, cyclopropyl, cyclobutyl, cyclopentyl, cyclohexyl.

In certain embodiments, $R^{20}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{20}$ is $C_1$-$C_6$alkylS $C_1$-$C_6$alkyl. In certain embodiments, $R^{20}$ is $C_1$-$C_6$alkylOH. Examples of suitable alcohols, include, but are not limited to, hydroxymethyl, hydroxyethyl, hydroxypropyl and hydroxybutyl. In certain embodiments, $R^{20}$ is $C_1$-$C_6$alkylO$C_1$-$C_6$alkyl. Suitable $C_1$-$C_6$alkylO$C_1$-$C_6$alkyls include but are not limited to, dimethyl ether, ethyl methyl ether, diethyl ether, dipropyl ether, dibutyl ether and diisopropyl ether.

With regard to the compounds described herein, each occurrence of $R^{21}$ is independently selected from the group consisting of hydrogen, $C_1$-$C_6$alkyl and $C_3$-$C_6$cycloalkyl. In certain embodiments, each occurrence of $R^{21}$ is independently hydrogen. In certain embodiments described herein, $R^{21}$ is independently $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, each occurrence of $R^{21}$ is independently $C_3$-$C_6$cycloalkyl. Suitable cycloalkyl groups include, but are not limited to, cyclopropyl, cyclobutyl, cyclopentyl, cyclohexyl.

With regard to the compounds described herein, each occurrence of $R^{22}$ is independently selected from the group consisting of hydrogen, $C_1$-$C_6$alkyl and $C_3$-$C_6$cycloalkyl. In certain embodiments, each occurrence of $R^{22}$ is independently hydrogen. In certain embodiments described herein, $R^{22}$ is independently $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, each occurrence of $R^{22}$ is independently $C_3$-$C_6$cycloalkyl. Suitable cycloalkyl groups include, but are not limited to, cyclopropyl, cyclobutyl, cyclopentyl, cyclohexyl.

Also described herein are compounds of Formula III;

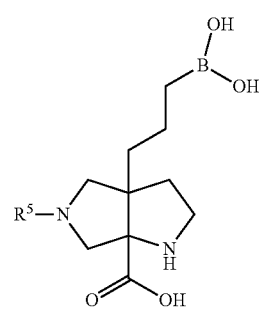

III or pharmaceutically acceptable salts thereof, wherein
$R^5$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylNH$_2$;

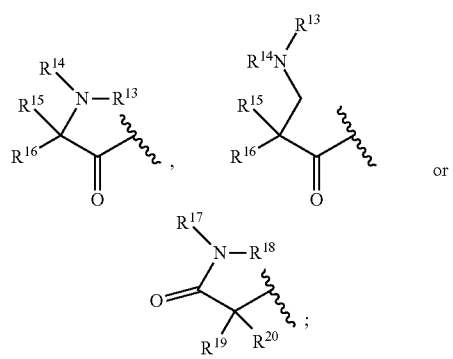

$R^{13}$ is hydrogen, $C_1$-$C_6$alkyl, $C_3$-$C_6$cycloalkyl, halo$C_1$-$C_6$alkyl, $C_1$-$C_6$alkylOH, COC$_1$-$C_6$alkylN($R^{21}$)($R^{22}$), or $C_1$-$C_6$alkylO$C_1$-$C_6$alkyl or when taken with $R^{14}$, forms a nitrogen containing heterocycle or when taken with $R^{15}$ or $R^{16}$ forms a nitrogen containing heteroaryl or heterocycle;

$R^{14}$ is hydrogen, $C_1$-$C_6$alkyl, $C_3$-$C_6$cycloalkyl, halo$C_1$-$C_6$alkyl, $C_1$-$C_6$alkylOH, COC$_1$-$C_6$alkylN($R^{21}$)($R^{22}$), or $C_1$-$C_6$alkylO$C_1$-$C_6$alkyl or when taken with $R^{13}$, forms a nitrogen containing heterocycle or when taken with $R^{15}$ or $R^{16}$, forms a nitrogen containing heteroaryl or heterocycle;

$R^{15}$ is hydrogen, $C_1$-$C_6$alkyl, $C_3$-$C_6$cycloalkyl, halo$C_1$-$C_6$alkyl, OH, $C_1$-$C_6$alkylOH, $C_1$-$C_6$alkylN($R^{21}$)($R^{22}$), $C_1$-$C_6$alkylCOOR$^{21}$, $C_1$-$C_6$alkylCON($R^{21}$)($R^{22}$), $C_1$-$C_6$alkylSH, $C_1$-$C_6$alkylSC$_1$-$C_6$alkyl or $C_1$-$C_6$alkylOC$_1$-$C_6$alkyl, $C_1$-$C_6$alkylaryl, $C_1$-$C_6$alkylheteroaryl, $C_1$-$C_6$alkylheterocycle or when taken with $R^{13}$ or $R^{14}$, forms a nitrogen containing heteroaryl or heterocycle, or when taken with $R^{16}$, forms a $C_3$-$C_7$cycloalkyl or heterocycle;

$R^{16}$ is hydrogen, $C_1$-$C_6$alkyl, $C_3$-$C_6$cycloalkyl, halo$C_1$-$C_6$alkyl, OH, $C_1$-$C_6$alkylOH, $C_1$-$C_6$alkylN($R^{21}$)($R^{22}$), $C_1$-$C_6$alkylCOOR$^{21}$, $C_1$-$C_6$alkylCON($R^{21}$)($R^{22}$), $C_1$-$C_6$alkylSH, $C_1$-$C_6$alkylSC$_1$-$C_6$alkyl or $C_1$-$C_6$alkylOC$_1$-$C_6$alkyl, $C_1$-$C_6$alkylaryl, $C_1$-$C_6$alkylheteroaryl, $C_1$-$C_6$alkylheterocycle or when taken with $R^{13}$ or $R^{14}$, forms a nitrogen containing heteroaryl or heterocycle, or when taken with $R^{15}$, forms a $C_3$-$C_7$cycloalkyl or heterocycle;

$R^{17}$ is hydrogen, $C_1$-$C_6$alkyl, $C_3$-$C_6$cycloalkyl, halo$C_1$-$C_6$alkyl, OH, $C_1$-$C_6$alkylOH, or $C_1$-$C_6$alkylOC$_1$-$C_6$alkyl or when taken with $R^{18}$, forms a nitrogen containing heterocycle;

$R^{18}$ is hydrogen, $C_1$-$C_6$alkyl, $C_3$-$C_6$cycloalkyl, halo$C_1$-$C_6$alkyl, OH, $C_1$-$C_6$alkylOH, or $C_1$-$C_6$alkylOC$_1$-$C_6$alkyl or when taken with $R^{17}$, forms a nitrogen containing heterocycle;

$R^{19}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylS $C_1$-$C_6$alkyl or $C_1$-$C_6$alkylOC$_1$-$C_6$alkyl;

$R^{20}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylS $C_1$-$C_6$alkyl or $C_1$-$C_6$alkylOC$_1$-$C_6$alkyl;

each occurrence of $R^{21}$ is independently selected from the group consisting of hydrogen, $C_1$-$C_6$alkyl and $C_3$-$C_6$cycloalkyl; and each occurrence of $R^{22}$ is independently selected from the group consisting of hydrogen, $C_1$-$C_6$alkyl and $C_3$-$C_6$cycloalkyl.

With regard to the compounds described herein, $R^5$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylNH$_2$;

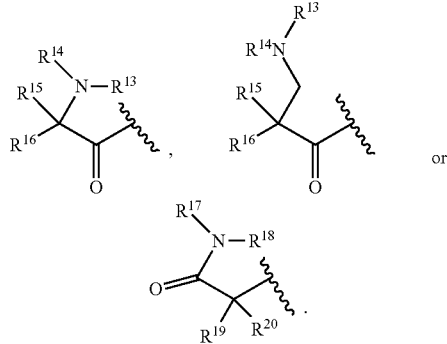

In certain embodiments described herein, $R^5$ is hydrogen. In certain embodiments described herein, $R^5$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^5$ is $C_3$-$C_6$cycloalkyl. Suitable cycloalkyl groups include, but are not limited to, cyclopropyl, cyclobutyl, cyclopentyl, cyclohexyl.

In certain embodiments, $R^5$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^5$ is $C_1$-$C_6$alkylOH. Examples of suitable alcohols, include, but are not limited to, hydroxymethyl, hydroxyethyl, hydroxypropyl and hydroxybutyl. In certain embodiments, $R^5$ is $C_1$-$C_6$alkylNH$_2$.

In certain embodiments, $R^5$ is:

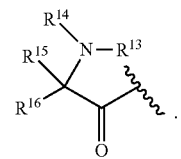

In certain embodiments, $R^5$ is:

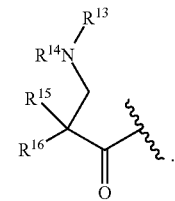

In certain embodiments, $R^5$ is:

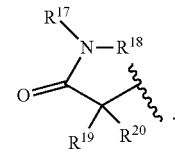

In certain embodiments, $R^{13}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{13}$ is $C_1$-$C_6$alkylOH. Examples of suitable alcohols, include, but are not limited to, hydroxymethyl, hydroxyethyl, hydroxypropyl and hydroxybutyl. In certain embodiments, $R^{13}$ is COC$_1$-$C_6$alkylN($R^{21}$)($R^{22}$). In certain embodiments, $R^{13}$ is $C_1$-$C_6$alkylOC$_1$-$C_6$alkyl. Suitable $C_1$-$C_6$alkylOC$_1$-$C_6$alkyls include but are not limited to, dimethyl ether, ethyl methyl ether, diethyl ether, dipropyl ether, dibutyl ether and diisopropyl ether.

In certain embodiments, $R^{13}$, when taken with $R^{14}$, forms a nitrogen containing heterocycle or when taken with $R^{15}$ or $R^{16}$, forms a nitrogen containing heteroaryl or heterocycle. In certain embodiments, $R^{13}$, when taken with $R^{14}$, forms a nitrogen containing heterocycle. In certain embodiments, $R^{13}$, when taken with $R^{15}$ and $R^{14}$, forms a nitrogen containing heteroaryl or heterocycle. In certain embodiments, $R^{13}$, when taken with $R^{16}$ and $R^{14}$, forms a nitrogen containing heteroaryl or heterocycle. Suitable heteroaryls include, but are not limited to, pyridyl (pyridinyl), imidazolyl, triazolyl, triazinyl, pyrimidyl, pyridazinyl, indolizinyl, cinnolinyl, phthalazinyl, quinazolinyl, naphthyridinyl, quinoxalinyl, purinyl, benzimidazolyl, quinolyl, isoquinolyl.

Suitable heterocycles include, but are not limited to, include mono- or bicyclic or bridged partially unsaturated and saturated rings containing at least one nitrogen, each of said ring having from 3 to 10 atoms in which the point of attachment may be carbon or nitrogen. Examples include tetrahydropyranyl, pyrrolidinyl, piperidinyl, piperazinyl, imidazolidinyl, 2,3-dihydrofuro(2,3-b)pyridyl, isoindolinyl, tetrahydropyran, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

In certain embodiments wherein $R^{13}$ forms a heterocycle or heteroaryl with $R^{15}$ or $R^{16}$, $R^{14}$ may become a bond to accommodate stability of the heterocycle or heteroaryl. Alternatively, in certain embodiments wherein $R^{14}$ forms a heterocycle or heteroaryl with $R^{15}$ or $R^{16}$, $R^{13}$ may become a bond to accommodate stability of the heterocycle or heteroaryl.

With regard to the compounds described herein, $R^{14}$ hydrogen, $C_1$-$C_6$alkyl, $C_3$-$C_6$cycloalkyl, halo$C_1$-$C_6$alkyl, $C_1$-$C_6$alkylOH, COC$_1$-$C_6$alkylN($R^{21}$)($R^{22}$), or $C_1$-$C_6$alkylOC$_1$-$C_6$alkyl or when taken with $R^{13}$, forms a nitrogen containing heterocycle or when taken with $R^{15}$ or $R^{16}$, forms a nitrogen containing heteroaryl or heterocycle.

In certain embodiments, $R^{14}$ is hydrogen. In certain embodiments described herein, $R^{14}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{14}$ is $C_3$-$C_6$cycloalkyl. Suitable cycloalkyl groups include, but are not limited to, cyclopropyl, cyclobutyl, cyclopentyl, cyclohexyl.

In certain embodiments, $R^{14}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{14}$ is $C_1$-$C_6$alkylOH. Examples of suitable alcohols, include, but are not limited to, hydroxymethyl, hydroxyethyl, hydroxypropyl and hydroxybutyl. In certain embodiments, $R^{14}$ is COC$_1$-$C_6$alkylN($R^{21}$)($R^{22}$). In certain embodiments, $R^{14}$ is $C_1$-$C_6$alkylOC$_1$-$C_6$alkyl. Suitable $C_1$-$C_6$alkylOC$_1$-$C_6$alkyls include but are not limited to, dimethyl ether, ethyl methyl ether, diethyl ether, dipropyl ether, dibutyl ether and diisopropyl ether.

In certain embodiments, $R^{14}$, when taken with $R^{13}$, forms a nitrogen containing heterocycle or when taken with $R^{15}$ or $R^{16}$, forms a nitrogen containing heteroaryl or heterocycle. In certain embodiments, $R^{14}$, when taken with $R^{13}$, forms a nitrogen containing heterocycle. In certain embodiments, $R^{14}$, when taken with $R^{15}$, forms a nitrogen containing heteroaryl or heterocycle. In certain embodiments, $R^{14}$, when taken with $R^{16}$, forms a nitrogen containing heteroaryl or heterocycle. Suitable heteroaryls include, but are not limited to, pyridyl (pyridinyl), imidazolyl, triazolyl, triazinyl, pyrimidyl, pyridazinyl, indolizinyl, cinnolinyl, phthalazinyl, quinazolinyl, naphthyridinyl, quinoxalinyl, purinyl, benzimidazolyl, quinolyl, isoquinolyl.

Suitable heterocycles include, but are not limited to, include mono- or bicyclic or bridged partially unsaturated and saturated rings containing at least one nitrogen, each of said ring having from 3 to 10 atoms in which the point of attachment may be carbon or nitrogen. Examples include tetrahydropyranyl, pyrrolidinyl, piperidinyl, piperazinyl, imidazolidinyl, 2,3-dihydrofuro(2,3-b)pyridyl, isoindolinyl, tetrahydropyran, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

With regard to the compounds described herein, $R^{15}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylN($R^{21}$)($R^{22}$), $C_1$-$C_6$alkylCOOR$^{21}$, $C_1$-$C_6$alkylCON($R^{21}$)($R^{22}$), $C_1$-$C_6$alkylSH, $C_1$-$C_6$alkylSC$_1$-$C_6$alkyl or $C_1$-$C_6$alkylOC$_1$-$C_6$alkyl, $C_1$-$C_6$alkylaryl, $C_1$-$C_6$alkylheteroaryl, $C_1$-$C_6$alkylheterocycle or when taken with $R^{13}$ or $R^{14}$, forms a nitrogen containing heteroaryl or heterocycle, or when taken with $R^{16}$, forms a $C_3$-$C_7$cycloalkyl or heterocycle.

In certain embodiments, $R^{15}$ is hydrogen. In certain embodiments described herein, $R^{15}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{15}$ is $C_3$-$C_6$cycloalkyl. Suitable cycloalkyl groups include, but are not limited to, cyclopropyl, cyclobutyl, cyclopentyl, cyclohexyl.

In certain embodiments, $R^{15}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{14}$ is $C_1$-$C_6$alkylOH. Examples of suitable alcohols, include, but are not limited to, hydroxymethyl, hydroxyethyl, hydroxypropyl and hydroxybutyl. In certain embodiments, $R^{15}$ is COC$_1$-$C_6$alkylN($R^{21}$)($R^{22}$). In certain embodiments, $R^{15}$ is $C_1$-$C_6$alkylOC$_1$-$C_6$alkyl. Suitable $C_1$-$C_6$alkylOC$_1$-$C_6$alkyls include but are not limited to, dimethyl ether, ethyl methyl ether, diethyl ether, dipropyl ether, dibutyl ether and diisopropyl ether.

In certain embodiments, $R^{15}$ is $C_1$-$C_6$alkylCOOR$^{21}$. In certain embodiments, $R^{15}$ is $C_1$-$C_6$alkylCON($R^{21}$)($R^{22}$). Examples of suitable COC$_1$-$C_6$alkylN($R^{21}$)($R^{22}$) groups include, but are not limited to, COCH$_2$NH$_2$, COCH$_2$NH(CH$_3$), COCH$_2$N(CH$_3$)$_2$ and COCH$_2$CH$_2$N(CH$_3$)$_2$. In certain embodiments, $R^{15}$ is $C_1$-$C_6$alkylSH. In certain embodiments, $R^{15}$ is $C_1$-$C_6$alkylSC$_1$-$C_6$alkyl. In certain embodiments, $R^{15}$ is $C_1$-$C_6$alkylOC$_1$-$C_6$alkyl. In certain embodiments, $R^{15}$ is $C_1$-$C_6$alkylaryl. In certain embodiments, $R^{15}$ is $C_1$-$C_6$alkylheteroaryl. In certain embodiments, $R^{15}$ is $C_1$-$C_6$alkylheterocycle. In certain embodiments, $R^{15}$ is when taken with $R^{13}$ or $R^{14}$, forms a nitrogen containing heteroaryl or heterocycle, or when taken with $R^{16}$, forms a $C_3$-$C_7$cycloalkyl or heterocycle.

In certain embodiments, $R^{15}$, when taken with $R^{13}$ or $R^{14}$, forms a nitrogen containing heteroaryl or heterocycle. In certain embodiments, $R^{15}$, when taken with $R^{13}$ and $R^{14}$, forms a nitrogen containing heteroaryl or heterocycle. In certain embodiments, $R^{15}$, when taken with $R^{14}$, forms a nitrogen containing heteroaryl or heterocycle. Suitable heteroaryls include, but are not limited to, pyridyl (pyridinyl), imidazolyl, triazolyl, triazinyl, pyrimidyl, pyridazinyl, indolizinyl, cinnolinyl, phthalazinyl, quinazolinyl, naphthyridinyl, quinoxalinyl, purinyl, benzimidazolyl, quinolyl, isoquinolyl.

With regard to the compounds described herein, $R^{16}$ is hydrogen, $C_1$-$C_6$alkyl, $C_3$-$C_6$cycloalkyl, haloC$_1$-$C_6$alkyl, $C_1$-$C_6$alkylOH, $C_1$-$C_6$alkylN(R$^{21}$)(R$^{22}$), $C_1$-$C_6$alkylCOOR$^{21}$, $C_1$-$C_6$alkylCON(R$^{21}$)(R$^{22}$), $C_1$-$C_6$alkylSH, $C_1$-$C_6$alkylSC$_1$-$C_6$alkyl or $C_1$-$C_6$alkylOC$_1$-$C_6$alkyl, $C_1$-$C_6$alkylaryl, $C_1$-$C_6$alkylheteroaryl, $C_1$-$C_6$alkylheterocycle or when taken with $R^{13}$ or $R^{14}$, forms a nitrogen containing heteroaryl or heterocycle, or when taken with $R^{15}$, forms a $C_3$-$C_7$cycloalkyl or heterocycle.

In certain embodiments, $R^{16}$ is hydrogen. In certain embodiments described herein, $R^{16}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{16}$ is $C_3$-$C_6$cycloalkyl. Suitable cycloalkyl groups include, but are not limited to, cyclopropyl, cyclobutyl, cyclopentyl, cyclohexyl.

In certain embodiments, $R^{16}$ is haloC$_1$-$C_6$alkyl. Suitable haloC$_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{16}$ is $C_1$-$C_6$alkylOH. Examples of suitable alcohols, include, but are not limited to, hydroxymethyl, hydroxyethyl, hydroxypropyl and hydroxybutyl. In certain embodiments, $R^{16}$ is COC$_1$-$C_6$alkylN(R$^{21}$)(R$^{22}$). In certain embodiments, $R^{16}$ is $C_1$-$C_6$alkylOC$_1$-$C_6$alkyl. Suitable $C_1$-$C_6$alkylOC$_1$-$C_6$alkyls include but are not limited to, dimethyl ether, ethyl methyl ether, diethyl ether, dipropyl ether, dibutyl ether and diisopropyl ether.

In certain embodiments, $R^{16}$ is $C_1$-$C_6$alkylCOOR$^{21}$. In certain embodiments, $R^{16}$ is $C_1$-$C_6$alkylCON(R$^{21}$)(R$^{22}$). Examples of suitable COC$_1$-$C_6$alkylN(R$^{21}$)(R$^{22}$) groups include, but are not limited to, COCH$_2$NH$_2$, COCH$_2$NH(CH$_3$), COCH$_2$N(CH$_3$)$_2$ and COCH$_2$CH$_2$N(CH$_3$)$_2$. In certain embodiments, $R^{16}$ is $C_1$-$C_6$alkylSH. In certain embodiments, $R^{16}$ is $C_1$-$C_6$alkylSC$_1$-$C_6$alkyl. In certain embodiments, $R^{16}$ is $C_1$-$C_6$alkylOC$_1$-$C_6$alkyl. In certain embodiments, $R^{16}$ is $C_1$-$C_6$alkylaryl. In certain embodiments, $R^{16}$ is $C_1$-$C_6$alkylheteroaryl. In certain embodiments, $R^{16}$ is $C_1$-$C_6$alkylheterocycle. In certain embodiments, $R^{16}$ is when taken with $R^{13}$ or $R^{14}$, forms a nitrogen containing heteroaryl or heterocycle, or when taken with $R^{15}$, forms a $C_3$-$C_7$cycloalkyl or heterocycle.

In certain embodiments, $R^{16}$, when taken with $R^{13}$ or $R^{14}$, forms a nitrogen containing heteroaryl or heterocycle. In certain embodiments, $R^{16}$, when taken with $R^{13}$ and $R^{14}$, forms a nitrogen containing heteroaryl or heterocycle. In certain embodiments, $R^{16}$, when taken with $R^{14}$, forms a nitrogen containing heteroaryl or heterocycle. Suitable heteroaryls include, but are not limited to, pyridyl (pyridinyl), imidazolyl, triazolyl, triazinyl, pyrimidyl, pyridazinyl, indolizinyl, cinnolinyl, phthalazinyl, quinazolinyl, naphthyridinyl, quinoxalinyl, purinyl, benzimidazolyl, quinolyl, isoquinolyl.

With regard to the compounds described herein, $R^{17}$ is hydrogen, $C_1$-$C_6$alkyl, $C_3$-$C_6$cycloalkyl, haloC$_1$-$C_6$alkyl, OH, $C_1$-$C_6$alkylOH, or $C_1$-$C_6$alkylOC$_1$-$C_6$alkyl or when taken with $R^{18}$, forms a nitrogen containing heterocycle.

In certain embodiments, $R^{17}$ is hydrogen. In certain embodiments described herein, $R^{17}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{17}$ is $C_3$-$C_6$cycloalkyl. Suitable cycloalkyl groups include, but are not limited to, cyclopropyl, cyclobutyl, cyclopentyl, cyclohexyl.

In certain embodiments, $R^{17}$ is haloC$_1$-$C_6$alkyl. Suitable haloC$_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{17}$ is OH. In certain embodiments, $R^{17}$ is $C_1$-$C_6$alkylOH. Examples of suitable alcohols, include, but are not limited to, hydroxymethyl, hydroxyethyl, hydroxypropyl and hydroxybutyl. In certain embodiments, $R^{17}$ is $C_1$-$C_6$alkylOC$_1$-$C_6$alkyl. Suitable $C_1$-$C_6$alkylOC$_1$-$C_6$alkyls include but are not limited to, dimethyl ether, ethyl methyl ether, diethyl ether, dipropyl ether, dibutyl ether and diisopropyl ether. In certain embodiments, $R^{17}$, when taken with $R^{18}$, forms a nitrogen containing heterocycle.

With regard to the compounds described herein, $R^{18}$ is hydrogen, $C_1$-$C_6$alkyl, $C_3$-$C_6$cycloalkyl, haloC$_1$-$C_6$alkyl, OH, $C_1$-$C_6$alkylOH, or $C_1$-$C_6$alkylOC$_1$-$C_6$alkyl or when taken with $R^{17}$, forms a nitrogen containing heterocycle.

In certain embodiments, $R^{18}$ is hydrogen. In certain embodiments described herein, $R^{18}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{18}$ is $C_3$-$C_6$cycloalkyl. Suitable cycloalkyl groups include, but are not limited to, cyclopropyl, cyclobutyl, cyclopentyl, cyclohexyl.

In certain embodiments, $R^{18}$ is haloC$_1$-$C_6$alkyl. Suitable haloC$_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{18}$ is OH. In certain embodiments, $R^{18}$ is $C_1$-$C_6$alkylOH. Examples of suitable alcohols, include, but are not limited to, hydroxymethyl, hydroxyethyl, hydroxypropyl and hydroxybutyl. In certain embodiments, $R^{18}$ is $C_1$-$C_6$alkylOC$_1$-$C_6$alkyl. Suitable $C_1$-$C_6$alkylOC$_1$-$C_6$alkyls include but are not limited to, dimethyl ether, ethyl methyl ether, diethyl ether, dipropyl ether, dibutyl ether and diisopropyl ether.

In certain embodiments, $R^{18}$, when taken with $R^{17}$, forms a nitrogen containing heterocycle. Suitable heterocycles include, but are not limited to, mono- or bicyclic or bridged partially unsaturated and saturated rings containing at least one nitrogen, each of said ring having from 3 to 10 atoms in which the point of attachment may be carbon or nitrogen.

Examples include tetrahydropyranyl, pyrrolidinyl, piperidinyl, piperazinyl, imidazolidinyl, 2,3-dihydrofuro(2,3-b) pyridyl, isoindolinyl, tetrahydropyran, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

With regard to the compounds described herein, $R^{19}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylS $C_1$-$C_6$alkyl or $C_1$-$C_6$alkylO$C_1$-$C_6$alkyl. In certain embodiments, $R^{19}$ is hydrogen. In certain embodiments described herein, $R^{19}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{19}$ is $C_3$-$C_6$cycloalkyl. Suitable cycloalkyl groups include, but are not limited to, cyclopropyl, cyclobutyl, cyclopentyl, cyclohexyl.

In certain embodiments, $R^{19}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{19}$ is $C_1$-$C_6$alkylS $C_1$-$C_6$alkyl. In certain embodiments, $R^{19}$ is $C_1$-$C_6$alkylOH. Examples of suitable alcohols, include, but are not limited to, hydroxymethyl, hydroxyethyl, hydroxypropyl and hydroxybutyl. In certain embodiments, $R^{19}$ is $C_1$-$C_6$alkylO$C_1$-$C_6$alkyl. Suitable $C_1$-$C_6$alkylO$C_1$-$C_6$alkyls include but are not limited to, dimethyl ether, ethyl methyl ether, diethyl ether, dipropyl ether, dibutyl ether and diisopropyl ether.

With regard to the compounds described herein, $R^{20}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylS $C_1$-$C_6$alkyl or $C_1$-$C_6$alkylO$C_1$-$C_6$alkyl. In certain embodiments, $R^{20}$ is hydrogen. In certain embodiments described herein, $R^{20}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{20}$ is $C_3$-$C_6$cycloalkyl. Suitable cycloalkyl groups include, but are not limited to, cyclopropyl, cyclobutyl, cyclopentyl, cyclohexyl.

In certain embodiments, $R^{20}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{20}$ is $C_1$-$C_6$alkylS $C_1$-$C_6$alkyl. In certain embodiments, $R^{20}$ is $C_1$-$C_6$alkylOH. Examples of suitable alcohols, include, but are not limited to, hydroxymethyl, hydroxyethyl, hydroxypropyl and hydroxybutyl. In certain embodiments, $R^{20}$ is $C_1$-$C_6$alkylO$C_1$-$C_6$alkyl. Suitable $C_1$-$C_6$alkylO$C_1$-$C_6$alkyls include but are not limited to, dimethyl ether, ethyl methyl ether, diethyl ether, dipropyl ether, dibutyl ether and diisopropyl ether.

With regard to the compounds described herein, each occurrence of $R^{21}$ is independently selected from the group consisting of hydrogen, $C_1$-$C_6$alkyl and $C_3$-$C_6$cycloalkyl. In certain embodiments, each occurrence of $R^{21}$ is independently hydrogen. In certain embodiments described herein, $R^{21}$ is independently $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, each occurrence of $R^{21}$ is independently $C_3$-$C_6$cycloalkyl. Suitable cycloalkyl groups include, but are not limited to, cyclopropyl, cyclobutyl, cyclopentyl, cyclohexyl.

With regard to the compounds described herein, each occurrence of $R^{22}$ is independently selected from the group consisting of hydrogen, $C_1$-$C_6$alkyl and $C_3$-$C_6$cycloalkyl. In certain embodiments, each occurrence of $R^{22}$ is independently hydrogen. In certain embodiments described herein, $R^{22}$ is independently $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, each occurrence of $R^{22}$ is independently $C_3$-$C_6$cycloalkyl. Suitable cycloalkyl groups include, but are not limited to, cyclopropyl, cyclobutyl, cyclopentyl, cyclohexyl.

With regard to the compounds described herein, $R^{23}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylN($R^{21}$)($R^{22}$), $C_1$-$C_6$alkylCOO$R^{21}$, $C_1$-$C_6$alkylCON($R^{21}$)($R^{22}$), $C_1$-$C_6$alkylSH, $C_1$-$C_6$alkylS$C_1$-$C_6$alkyl, $C_1$-$C_6$alkylO$C_1$-$C_6$alkyl, $C_1$-$C_6$alkylaryl, $C_1$-$C_6$alkylheteroaryl or $C_1$-$C_6$alkylheterocycle.

In certain embodiments, $R^{23}$ is hydrogen. In certain embodiments described herein, $R^{23}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{23}$ is methyl. In certain embodiments, $R^{23}$ is isopropyl. In certain embodiments, $R^{23}$ is isobutyl. In certain embodiments, $R^{23}$ is $C_3$-$C_6$cycloalkyl. Suitable cycloalkyl groups include, but are not limited to, cyclopropyl, cyclobutyl, cyclopentyl, cyclohexyl.

In certain embodiments, $R^{23}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{23}$ is $C_1$-$C_6$alkylOH. Examples of suitable alcohols, include, but are not limited to, hydroxymethyl, hydroxyethyl, hydroxypropyl and hydroxybutyl. In certain embodiments, $R^{23}$ is COC$_1$-$C_6$alkylN($R^{21}$)($R^{22}$). In certain embodiments, $R^{23}$ is $C_1$-$C_6$alkylO$C_1$-$C_6$alkyl. Suitable $C_1$-$C_6$alkylO$C_1$-$C_6$alkyls include but are not limited to, dimethyl ether, ethyl methyl ether, diethyl ether, dipropyl ether, dibutyl ether and diisopropyl ether.

In certain embodiments, $R^{23}$ is $C_1$-$C_6$alkylCOOR$^{21}$. In certain embodiments, $R^{23}$ is $C_1$-$C_6$alkylCON($R^{21}$)($R^{22}$). Examples of suitable COC$_1$-$C_6$alkylN($R^{21}$)($R^{22}$) groups include, but are not limited to, COCH$_2$NH$_2$, COCH$_2$NH(CH$_3$), COCH$_2$N(CH$_3$)$_2$ and COCH$_2$CH$_2$N(CH$_3$)$_2$. In certain embodiments, $R^{23}$ is $C_1$-$C_6$alkylSH. In certain embodiments, $R^{23}$ is $C_1$-$C_6$alkylSC$_1$-$C_6$alkyl. In certain embodiments, $R^{23}$ is $C_1$-$C_6$alkylOC$_1$-$C_6$alkyl. In certain embodiments, $R^{23}$ is $C_1$-$C_6$alkylaryl. In certain embodiments, $R^{23}$ is $C_1$-$C_6$alkylheteroaryl. In certain embodiments, $R^{23}$ is $C_1$-$C_6$alkylheterocycle. Suitable heteroaryls include, but are not limited to, pyridyl (pyridinyl), imidazolyl, triazolyl, triazinyl, pyrimidyl, pyridazinyl, indolizinyl, cinnolinyl, phthalazinyl, quinazolinyl, naphthyridinyl, quinoxalinyl, purinyl, benzimidazolyl, quinolyl, isoquinolyl. Suitable heterocycles include, but are not limited to, mono- or bicyclic or bridged partially unsaturated and saturated rings containing at least one nitrogen, each of said ring having from 3 to 10 atoms in which the point of attachment may be carbon or nitrogen. Examples include tetrahydropyranyl, pyrrolidinyl, piperidinyl, piperazinyl, imidazolidinyl, 2,3-dihydrofuro(2,3-b)pyridyl, isoindolinyl, tetrahydropyran, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

With regard to the compounds described herein, $R^{24}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylN($R^{21}$)($R^{22}$), $C_1$-$C_6$alkylCOOR$^{21}$, $C_1$-$C_6$alkylCON($R^{21}$)($R^{22}$), $C_1$-$C_6$alkylSH, $C_1$-$C_6$alkylSC$_1$-$C_6$alkyl, $C_1$-$C_6$alkylOC$_1$-$C_6$alkyl, $C_1$-$C_6$alkylaryl, $C_1$-$C_6$alkylheteroaryl or $C_1$-$C_6$alkylheterocycle.

In certain embodiments, $R^{24}$ is hydrogen. In certain embodiments described herein, $R^{24}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{24}$ is methyl. In certain embodiments, $R^{24}$ is isopropyl. In certain embodiments, $R^{24}$ is isobutyl. In certain embodiments, $R^{23}$ is $C_3$-$C_6$cycloalkyl. Suitable cycloalkyl groups include, but are not limited to, cyclopropyl, cyclobutyl, cyclopentyl, cyclohexyl.

In certain embodiments, $R^{24}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{24}$ is $C_1$-$C_6$alkylOH. Examples of suitable alcohols, include, but are not limited to, hydroxymethyl, hydroxyethyl, hydroxypropyl and hydroxybutyl. In certain embodiments, $R^{24}$ is COC$_1$-$C_6$alkylN($R^{21}$)($R^{22}$). In certain embodiments, $R^{24}$ is $C_1$-$C_6$alkylOC$_1$-$C_6$alkyl. Suitable $C_1$-$C_6$alkylOC$_1$-$C_6$alkyls include but are not limited to, dimethyl ether, ethyl methyl ether, diethyl ether, dipropyl ether, dibutyl ether and diisopropyl ether.

In certain embodiments, $R^{24}$ is $C_1$-$C_6$alkylCOOR$^{21}$. In certain embodiments, $R^{24}$ is $C_1$-$C_6$alkylCON($R^{21}$)($R^{22}$). Examples of suitable COC$_1$-$C_6$alkylN($R^{21}$)($R^{22}$) groups include, but are not limited to, COCH$_2$NH$_2$, COCH$_2$NH(CH$_3$), COCH$_2$N(CH$_3$)$_2$ and COCH$_2$CH$_2$N(CH$_3$)$_2$. In certain embodiments, $R^{24}$ is $C_1$-$C_6$alkylSH. In certain embodiments, $R^{24}$ is $C_1$-$C_6$alkylSC$_1$-$C_6$alkyl. In certain embodiments, $R^{24}$ is $C_1$-$C_6$alkylOC$_1$-$C_6$alkyl. In certain embodiments, $R^{24}$ is $C_1$-$C_6$alkylaryl. In certain embodiments, $R^{24}$ is $C_1$-$C_6$alkylheteroaryl. In certain embodiments, $R^{24}$ is $C_1$-$C_6$alkylheterocycle. Suitable heteroaryls include, but are not limited to, pyridyl (pyridinyl), imidazolyl, triazolyl, triazinyl, pyrimidyl, pyridazinyl, indolizinyl, cinnolinyl, phthalazinyl, quinazolinyl, naphthyridinyl, quinoxalinyl, purinyl, benzimidazolyl, quinolyl, isoquinolyl. Suitable heterocycles include, but are not limited to, mono- or bicyclic or bridged partially unsaturated and saturated rings containing at least one nitrogen, each of said ring having from 3 to 10 atoms in which the point of attachment may be carbon or nitrogen. Examples include tetrahydropyranyl, pyrrolidinyl, piperidinyl, piperazinyl, imidazolidinyl, 2,3-dihydrofuro(2,3-b)pyridyl, isoindolinyl, tetrahydropyran, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

Also described herein are compounds, selected from the following:

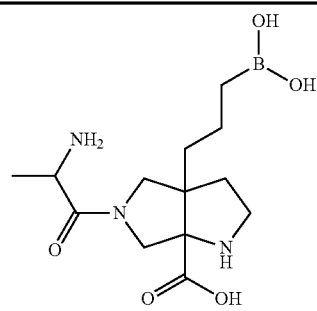

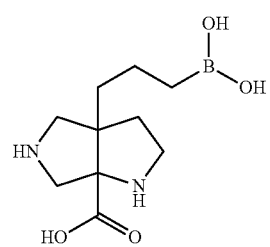 [SMILES: O=C(O)C12CNCC1(CCCB(O)O)CCN2]

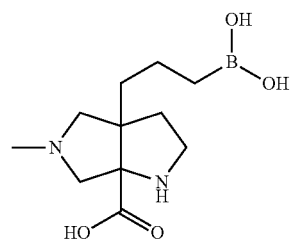 [SMILES: CN1CC2(CCCB(O)O)CCNC2(C(=O)O)C1]

-continued
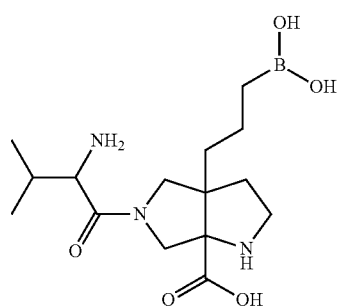 [SMILES: CC(C)C(N)C(=O)N1CC2(CCCB(O)O)CCNC2(C(=O)O)C1]
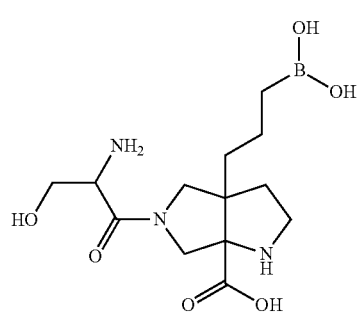 [SMILES: NC(CO)C(=O)N1CC2(CCCB(O)O)CCNC2(C(=O)O)C1]
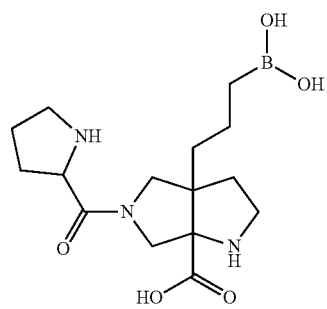 [SMILES: O=C(C1CCCN1)N1CC2(CCCB(O)O)CCNC2(C(=O)O)C1]
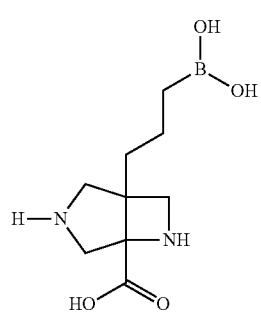
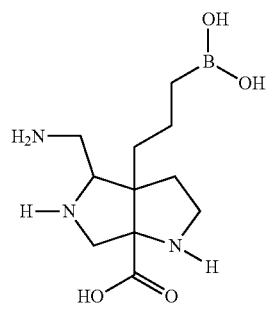 [SMILES: NCC1NCC2(C(=O)O)NCCC12CCCB(O)O]
-continued
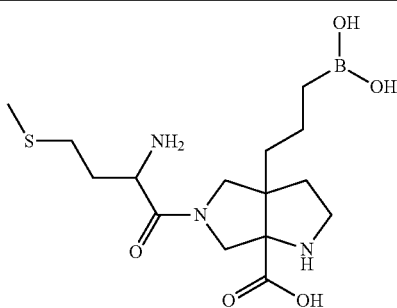
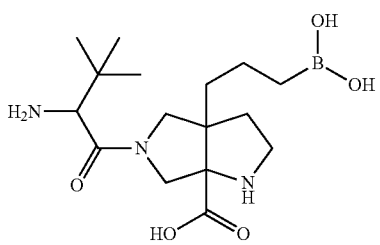 [SMILES: CC(C)(C)C(N)C(=O)N1CC2(CCCB(O)O)CCNC2(C(=O)O)C1]
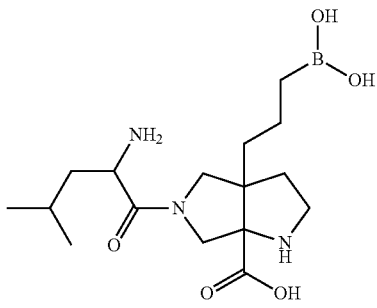
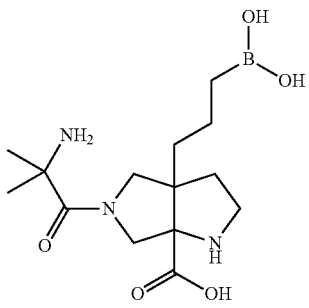 [SMILES: CC(C)(N)C(=O)N1CC2(CCCB(O)O)CCNC2(C(=O)O)C1]
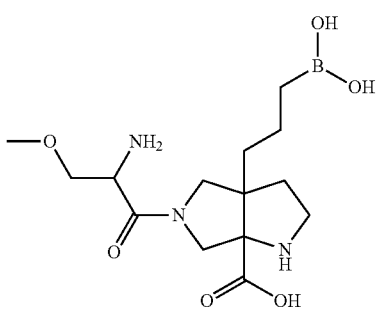 [SMILES: COCC(N)C(=O)N1CC2(CCCB(O)O)CCNC2(C(=O)O)C1]

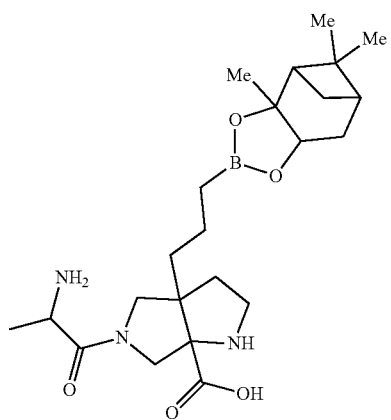 [SMILES: CC(N)C(=O)N1CC2(CCCB3OC4CC5CC(C5(C)C)C4(C)O3)CCNC2(C(=O)O)C1]
Specifically, described herein are compounds, selected from the following:
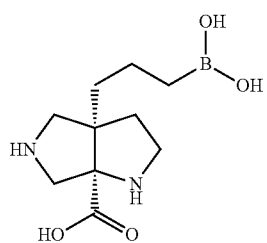 [SMILES: O=C(O)[C@]12CNC[C@@]1(CCCB(O)O)CCN2]
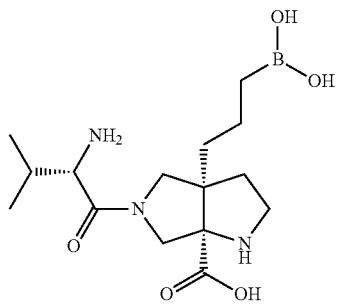 [SMILES: CC(C)[C@H](N)C(=O)N1C[C@@]2(CCCB(O)O)CCN[C@@]2(C(=O)O)C1]
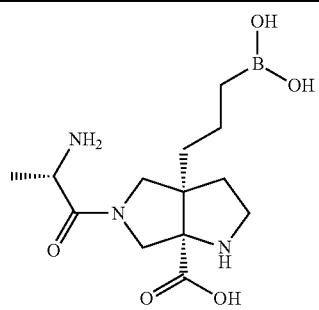
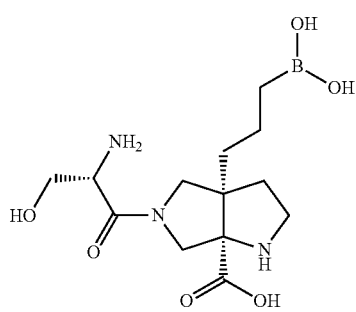 [SMILES: N[C@@H](CO)C(=O)N1C[C@@]2(CCCB(O)O)CCN[C@@]2(C(=O)O)C1]
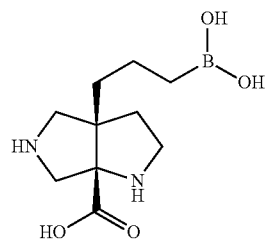
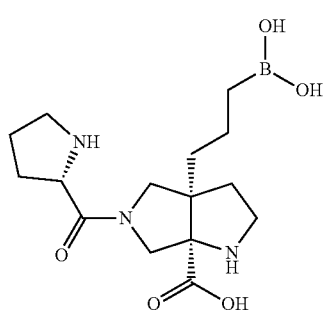 [SMILES: O=C([C@@H]1CCCN1)N1C[C@@]2(CCCB(O)O)CCN[C@@]2(C(=O)O)C1]
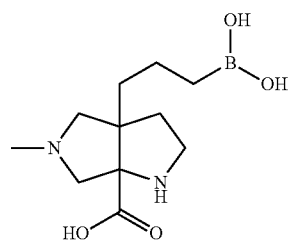
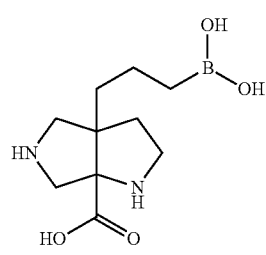
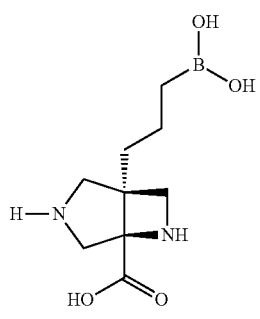 [SMILES: O=C(O)[C@]12CNC[C@@]1(CCCB(O)O)CN2]

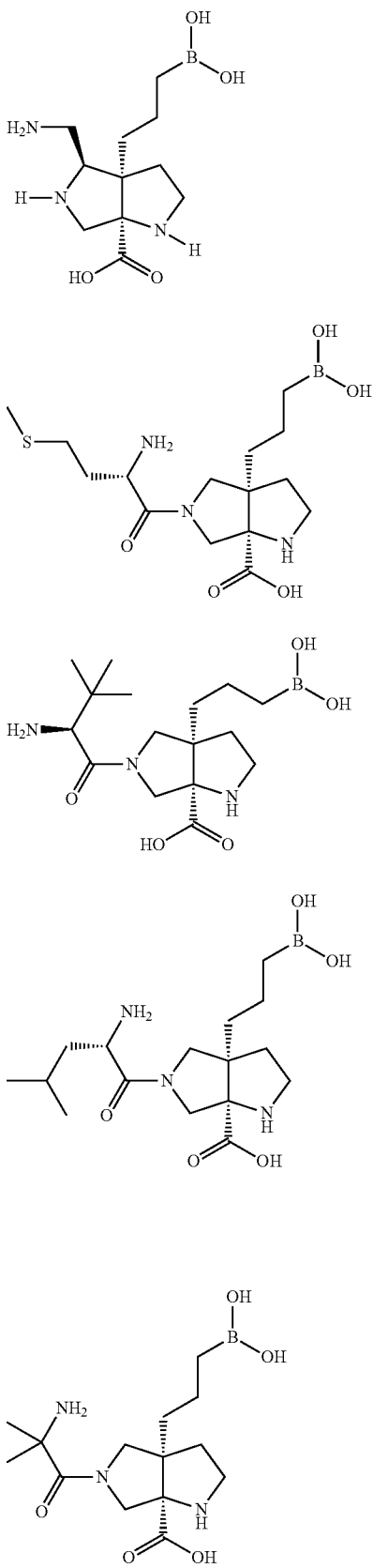
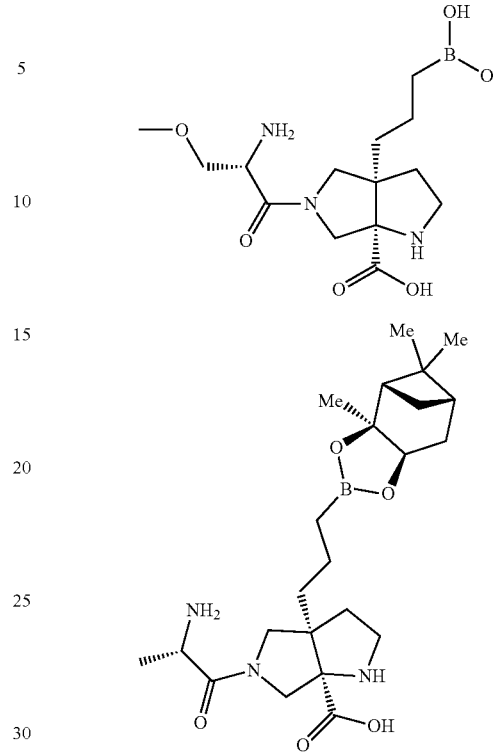

Definitions

The term "alkylene," or "alkylenyl" by itself or as part of another substituent means a divalent straight, branched or cyclic chain hydrocarbon radical having the stated number of carbon atoms. For example, —($C_1$-$C_5$) alkylenyl, would include, e.g., —$CH_2$—, —$CH_2CH_2$—, —$CH_2CH_2CH_2$—, —$CH_2CH_2CH_2CH_2$—, —$CH_2CH(CH_3)CH_2$— or —$CH_2CH_2CH_2CH_2CH_2$—.

The term "halogen" includes a fluorine, a chlorine, a bromine or an iodine radical.

The term "$C_1$-$C_6$alkyl" encompasses straight alkyl having a carbon number of 1 to 6 and branched alkyl having a carbon number of 3 to 6. Specific examples thereof include methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl, and the like.

The term "COOC$_1$-C$_6$alkyl" refers to a —COOH group wherein the OH is replaced with an alkoxy group as defined above. Examples include methoxycarbonyl, ethoxycarbonyl, isopropylcarbonyl and butoxycarbonyl.

The term "$C_3$-$C_6$cycloalkyl" encompasses bridged, saturated or unsaturated cycloalkyl groups having 3 to 6 carbons. "Cycloalkyl" also includes non-aromatic rings as well as monocyclic, non-aromatic rings fused to a saturated cycloalkyl group. Examples of cycloalkyl include cyclopropyl, cyclobutyl, cyclopentyl and cyclohexyl.

The term "$C_3$-$C_7$cycloalkyl" encompasses bridged, saturated or unsaturated cycloalkyl groups having 3 to 8 carbons.

"Cycloalkyl" also includes non-aromatic rings as well as monocyclic, non-aromatic rings fused to a saturated cycloalkyl group. Examples of cycloalkyl include cyclopropyl, cyclobutyl, cyclopentyl, cyclohexyl and cycloheptyl.

The term "$C_3$-$C_8$cycloalkyl" encompasses bridged, saturated or unsaturated cycloalkyl groups having 3 to 8 carbons. "Cycloalkyl" also includes non-aromatic rings as well as monocyclic, non-aromatic rings fused to a saturated cycloalkyl group. Examples of cycloalkyl include cyclopropyl, cyclobutyl, cyclopentyl, cyclohexyl, cycloheptyl, tetrahydronaphthyl, decahydronaphthyl, indanyl and the like.

The term "heteroaryl" means an aromatic heterocycle that contains at least one ring heteroatom selected from O, S and N. Examples of heteroaryl groups include pyridyl (pyridinyl), oxazolyl, imidazolyl, triazolyl, furyl, triazinyl, thienyl, pyrimidyl, pyridazinyl, indolizinyl, cinnolinyl, phthalazinyl, quinazolinyl, naphthyridinyl, quinoxalinyl, purinyl, benzimidazolyl, quinolyl, isoquinolyl, and the like.

The term "heterocycle" means mono- or bicyclic or bridged partially unsaturated and saturated rings containing at least one heteroatom selected from N, S and O, each of said rings having from 3 to 10 atoms in which the point of attachment may be carbon or nitrogen. Examples include tetrahydropyranyl, tetrahydrofuranyl, pyrrolidinyl, piperidinyl, piperazinyl, dioxanyl, imidazolidinyl, 2,3-dihydrofuro(2,3-b)pyridyl, benzoxazinyl, benzoxazolinyl, 2-H-phthalazinyl, isoindolinyl, benzoxazepinyl, 5,6-dihydroimidazo[2,1-b]thiazolyl, tetrahydroquinolinyl, morpholinyl, tetrahydroisoquinolinyl, dihydroindolyl, tetrahydropyran, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils). The term also includes bridged rings such as 5-azabicyclo[2.2.1]heptyl, 2,5-diazabicyclo[2.2.1]heptyl, 2-azabicyclo[2.2.1]heptyl, 7-azabicyclo[2.2.1]heptyl, 2,5-diazabicyclo[2.2.2]octyl, 2-azabicyclo[2.2.2]octyl, and 3-azabicyclo[3.2.2]nonyl, and azabicyclo[2.2.1]heptanyl.

The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidinyl, glucamine, glucosamine, histidine, hydrabamine, isopropylamine, lysine, methylglucamine, morpholine, piperazine, piperidinyl, polyamine resins, procaine, purines, theobromine, triethylamine, trimethylamine, tripropylamine, tromethamine, and the like.

The term "patient" refers to a mammalian patient, preferably a human patient, receiving or about to receive medical treatment.

The compounds of the present invention may contain one or more asymmetric centers and can thus occur as racemates, racemic mixtures, single enantiomers, diastereomeric mixtures, and individual diastereomers. The present invention is meant to comprehend all such isomeric forms of these compounds.

Some of the compounds described herein contain olefinic double bonds, and unless specified otherwise, are meant to include both E and Z geometric isomers.

Some of the compounds described herein contain substituted cycloalkanes having cis- and trans-isomers, and unless specified otherwise, are meant to include both cis- and trans-geometric isomers.

The independent syntheses of these diastereomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

It will be understood that the present invention is meant to include the pharmaceutically acceptable salts, and also salts that are not pharmaceutically acceptable, of the compounds described herein, when they are used as precursors to the free compounds or their pharmaceutically acceptable salts or in other synthetic manipulations.

Solvates, and in particular, the hydrates of the compounds of the structural formulas described herein are included in the present invention as well.

Some of the compounds described herein may exist as tautomers, which have different points of attachment of hydrogen accompanied by one or more double bond shifts.

For example, a ketone and its enol form are keto-enol tautomers. The individual tautomers as well as mixtures thereof are encompassed with compounds of the present invention.

The compounds of the present invention may also exist in open-chain or cyclized forms. In some cases one or more of the cyclized forms may result in loss of water. The specific composition of the open-chain and cyclized forms may be dependent on how the compound is isolated, stored or administered. For example, the compound may exist primarily in an open-chained form under acidic conditions but cyclize under neutral conditions. All forms are included in the invention.

In the compounds described herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the formulas described herein. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the Schemes and Examples herein using appropriate isotopically-enriched reagents or Intermediates.

It should be noted that chemically unstable compounds are excluded from the embodiments contained herein.

Methods of Treatment

Also encompassed by the present invention are methods of treating arginase-related diseases. The compounds described herein can be effective in preventing or treating various arginase-related diseases, such as gastrointestinal diseases, pulmonary inflammatory diseases, sexual arousal disorders, cardiovascular disorders, diseases caused by pathogenic microorganisms, immunological disorders, cancer, pre-term labor, Reynaud's disease, psoriasis, rheumatoid arthritis, and Peyronie's Disease, among others.

An increase in arginase activity has been associated with the pathophysiology of a number of conditions including impairment in non-adrenergic and non-cholinergic (NANC) nerve-mediated relaxation of gastrointestinal smooth muscle. An arginase inhibitor can be used to alleviate such impairment by administering the inhibitor to a mammal experiencing such impairment or a mammal which is anticipated to experience such impairment (e.g., a human afflicted with a gastrointestinal motility disorder).

Accordingly, the compounds of the invention may be useful in the treatment or prevention of gastrointestinal motility disorders, which is based on the observation that arginase is present in opossum internal anal sphincter muscle and the known arginase inhibitor, (S)-2-amino-6-boronohexanoic acid (ABH), has been shown to relax this muscle. See, e.g., Baggio et al., J. Pharm. Exp. Ther. 290, 1409-16 (1999).

The compounds of the invention may also be useful in the treatment or prevention of inflammatory bowel disease (IBD, e.g., Crohn's disease and ulcerative colitis). In fact, IBD has been shown to be characterized by increased arginase activity and endothelial dysfunction. See, e.g., Horowitz et al., Am. J. Physiol. Gastrointest. Liver Physiol. 292, G1323-36 (2007).

Likewise, the compounds of the invention may be useful in the treatment or prevention of gastric ulcers, because the bacterium that causes stomach ulcers, *Helicobacter pylori*, exhibits increased arginase activity upon colonization in order to evade the human immune response. See, e.g., Gobert et al., Proc. Natl. Acad. Sci. (USA) 98, 13844-49 (2001).

The compounds of the invention may be useful in the treatment or prevention of asthma based on the observation that arginase is upregulated in the asthmatic airway. See, e.g., Zimmermann and Rothenberg, Eur. J. Pharmacol. 533, 253-62 (2006). Furthermore, nebulizer treatment of guinea pigs with ABH in an allergic asthma model prevents airway hyperresponsiveness. See, e.g., Maarsingh, "Arginase: A Novel Key Enzyme in the Pathophysiology of Allergic Asthma," Ph. D. dissertation, Chapter 9, University of Groningen, Netherlands (2006); Maarsingh et al., Am. J. Respir. Crit. Care Med. 178, 565-73 (2008). The asthma phenotype is characterized by airway constriction, airway smooth muscle hyperplasia, and the chronic accumulation of fibrotic tissue; an arginase inhibitor can relax airway smooth muscle and attenuate cellular hyperplasia and fibrosis.

Additionally, the compounds of the invention may be useful in the treatment or prevention of chemically-induced lung fibrosis because arginase I and II are induced in bleomycin-induced lung fibrosis in order to provide more L-ornithine for collagen biosynthesis. See, e.g., Endo et al., Am. J. Physiol. Lung Cell Mol. Physiol. 285, L313-21 (2003).

The compounds of the invention may also be useful in the treatment or prevention of idiopathic pulmonary fibrosis, based on the observation that virus-induced upregulation of arginase I is observed in an animal model. See, e.g., Mora et al., Am. J. Respir. Cell Mol. Biol. 35, 466-73 (2006).

Furthermore, the compounds of the invention may be useful in the treatment or prevention of cystic fibrosis. Increased sputum arginase activity contributes to nitric oxide deficiency in cystic fibrosis lung disease; arginase activity also contributes to fibrosis. See, e.g., Graseman et al., Am. J. Respir. Crit. Care Med. 172, 1523-28 (2005).

Erectile dysfunction afflicts one-half of the male population over the age of forty. This malady often results from defects in the complex cascade of enzyme-catalyzed reactions governing blood flow into and out of the corpus cavernosum, a chamber of muscular, spongy tissue that becomes engorged with blood in the erect penis. Defects that compromise cavernosal blood flow often occur as secondary complications related to other health conditions, such as heart disease, hypertension, diabetes, use of certain medications, and the like.

In an important embodiment, the invention relates to use of an arginase inhibitor described herein for enhancing penile erectile function in a mammal (preferably a male human) or for alleviating erectile dysfunction in a mammal. Nitric oxide is an important regulator of erectile function and mediates NANC neurotransmission in penile corpus cavernosum smooth muscle, leading to rapid relaxation, which in turn leads to erection. Nitric oxide synthase, which catalyzes oxidation of L-arginine to form L-citrulline and nitric oxide, is for this reason a key enzyme in penile smooth muscle physiology. Arginase catalyzes hydrolysis of L-arginine to form L-ornithine and urea. Arginase regulates nitric oxide synthase activity by affecting the amount of L-arginine available for oxidation catalyzed by nitric oxide synthase activity. Thus, inhibition of arginase activity can enhance nitric oxide synthase activity, thereby enhancing nitric oxide-dependent smooth muscle relaxation in the corpus cavernosum and enhancing penile erection.

Arginase is present in rabbit and human penile corpus cavernosum and ABH enhances the nitric oxide-dependent relaxation of this tissue. See, e.g., Cox et al., Nature Struct. Biol. 6, 1043-47 (1999). The arginase inhibitor, ABH, enhances the erectile response in live male rabbits. See, e.g., Cama et al., Biochemistry 42, 8445-51 (2003). Arginase II is upregulated in the corpus cavernosum of the diabetic man, resulting in reduced nitric oxide biosynthesis which, in turn, leads to erectile dysfunction; administration of ABH in ex vivo experiments restores nitric oxide biosynthesis. See, e.g., Bivalacqua et al., Biochem. Biophys. Res. Commun. 283, 923-27 (2001). Arginase I is upregulated in the penis of aged mice and impairs erectile function. See, e.g., Bivalacqua et al., Am. J. Physiol. Heart Circ. Physiol. 292, H1340-51 (2007).

The compounds of the invention may also be useful in the treatment or prevention of female sexual arousal disorder. The arginase inhibitor, ABH, enhances the engorgement response in the genitalia of live female rabbits. See, e.g., Cama et al., Biochemistry 42, 8445-51 (2003).

The compounds of the invention may be useful in the treatment or prevention of endothelial vascular dysfunction in atherosclerosis, hypertension, hypercholesterolemia, and diabetes. Arginase modulates NOS activity by regulation of L-arginine availability, and the deleterious effects of arginase can be blocked by an arginase inhibitor. See, e.g., Berkowitz et al., Circulation 108, 2000-06 (2003); Yang and Ming, Clin. Med. Res. 4, 53-65 (2006). Increased arginase activity in diabetes contributes to vascular endothelial dysfunction by decreasing L-arginine availability to nitric oxide synthase. See, e.g., Romero et al., Circ. Res. 102, 95-102 (2008). Arginase inhibition attenuates hypertension in spontaneously hypertensive rats. See, e.g., Demougeot et al., J. Hypertens. 23, 971-78 (2005). Other relevant conditions include ischemia-reperfusion injury, peripheral vascular disease (PVD), peripheral arterial disease (PAD), and subarachnoid hemorrhage. Arginase has been identified as a new drug target for the treatment of atherosclerosis. See, e.g., Yang and Ming, Curr. Hypertension Rep. 8, 54-59 (2006).

The compounds of the invention may be useful in the treatment or prevention of pulmonary arterial hypertension. Elevated arginase activity contributes to vascular endothelial dysfunction by compromising L-arginine availability to nitric oxide synthase. See, e.g., Morris et al., Adv. Pulmonary Hypertension 5, 31-36 (2007).

The compounds of the invention may be useful in the treatment or prevention of African sleeping sickness, Chagas' disease, leishmaniasis, malaria, and other diseases caused by pathogenic microorganisms. Polyamine biosynthetic enzymes are essential for growth and survival of protozoa. See, e.g., Heby et al., Biochem. Soc. Trans. 31, 415-19 (2003). Arginase is essential for viability. See, e.g., Roberts et al., J. Biol. Chem. 279, 23668-78 (2004). Therefore, inhibitors of protozoan arginases can kill the protozoa.

The compounds of the invention may be useful in the treatment or prevention of multiple sclerosis, and possibly other autoimmune diseases, based upon the observation that arginase I is upregulated in an animal model of multiple sclerosis (experimental autoimmune encephalomyelitis) and administration of the arginase inhibitor ABH improves the disease score of animals. See, e.g., Xu et al., Immunology 110, 141-48 (2003).

Tumor-induced tolerance impairs the therapeutic efficacy of immunotherapy; one mechanism leading to T-cell tolerance is the generation of myeloid-derived suppressor cells (MDSCs), which produce arginase, thereby depleting the tumor microenvironment of L-arginine, which impairs T-cell signal transduction and function. Notably, arginase activity is a mechanism of immune system evasion that is also shared by certain bacteria, e.g., *Helicobacter pylori*. MDSCs are regarded as "cancer's bulwark against immune attack." See, e.g., Marx, Science 319, 154-56 (2008).

Accordingly, arginase is upregulated in the following types of cancers, which may be treated with an arginase inhibitor described herein: Renal cell carcinoma (see, e.g., Zea et al., Cancer Res. 65, 3044-48 (2005); Ochoa et al., Clin. Cancer Res. 13, 721s-26s (2007)); prostate cancer (see, e.g., Bronte et al., J. Exp. Med. 201, 1257-68 (2005) (arginase inhibition with N-hydroxy-L-arginine facilitates tumor immunotherapy); colorectal cancer (see, e.g., Leu and Wang, Cancer 70, 733-36 (1992); Bronte and Zanovello, Nature Rev. Immunol. 5, 641-54 (2005)); breast cancer (see, e.g., Singh et al., Cancer Res. 60, 3305-12 (2000); Bronte and Zanovello, Nature Rev. Immunol. 5, 641-54 (2005) (the arginase inhibitor, N-hydroxy-L-arginine, inhibits cell proliferation and induces apoptosis)); skin cancer (squamous cell and basal cell cancers) (see, e.g., Gokmen et al., J. Lab. Clin. Med. 137, 340-44 (2001); Bronte and Zanovello, Nature Rev. Immunol. 5, 641-54 (2005)); lung cancer (see, e.g., Rodriguez et al., J. Exp. Med. 202, 931-39 (2005); Bronte and Zanovello, Nature Rev. Immunol. 5, 641-54 (2005)); ovarian cancer (see, e.g., Melichar et al., J. Translational Med. 1, 1-5 (2003) (doi:10.11861479-5876-1-5)); and gastric cancer (see, e.g., Wu et al., Life Sci. 51, 1355-61 (1992)); among others.

Enhancement of uterine smooth muscle relaxation with an arginase inhibitor may be useful in the management of pre-term labor.

Reynaud's disease is a disease of the microvasculature. Because subcutaneous administration of the arginase inhibitor (S)-(2-Boronoethyl)-L-cysteine (BEC, which is an analogue of ABH) in humans is vasodilatory and enhances circulation, an arginase inhibitor may be useful in treating Reynaud's disease. See, e.g., Holowatz et al., J. Physiol. 574, 573-81 (2006).

Arginase I is highly overexpressed in the hyperproliferative psoriatic epidermis in human skin, and therefore arginase inhibitors may be useful in the treatment of psoriasis. See, e.g., Bruch-Gerharz et al., Am. J. Pathology 162, 203-11 (2003).

Arginase II is upregulated in synovial fluid from human patients, and therefore arginase inhibitors may be useful in the treatment of arthritis. See, e.g., Huang et al., Kaohsiung J. Med. Sci. 17, 358-63 (2001); Corraliza and Moncada, J. Rheumatol. 29, 2261-65 (2002).

The compounds of the invention may be useful in the treatment or prevention of Peyronie's disease. Arginase II is upregulated in the rat penis in an animal model for this disease. See, e.g., Bivalacqua et al., J. Andrology 22, 497-506 (2001). While this disorder can contribute to erectile dysfunction, it is principally an inflammatory condition in which fibrotic tissue builds up in the penis.

The composition of the invention can be used to treat a disorder in a mammal, wherein the disorder is associated with expression of an abnormally high level of arginase activity in a tissue of the mammal. Because nitric oxide synthase activity is regulated in a reciprocal fashion with respect to arginase activity in mammals, more particularly humans, the compounds and compositions of the invention can be used to treat a disorder in a mammal, wherein the disorder is associated with expression of an abnormally low level of nitric oxide synthase activity in a tissue of the mammal. Since the reciprocal interaction of arginase and nitric oxide synthase has implications for the function of smooth muscle, the use of the compounds described herein for the regulation of smooth muscle activity in an animal is also contemplated in the invention. Of course, a compound of the invention or a composition comprising the compound of the invention which comprises an arginase inhibitor described herein can also be used to inhibit arginase in a mammal having normal levels of arginase and nitric oxide synthase activity, particularly where the physiology which is desired to be effected is one which is affected by arginase or nitric oxide synthase activity, or where a disorder which is not caused by aberrant arginase or nitric oxide synthase activity levels can nonetheless be alleviated or inhibited by inhibiting arginase activity (e.g., certain forms of erectile dysfunction).

The invention also includes a method of enhancing smooth muscle relaxation comprising contacting the smooth muscle with an arginase inhibitor. The smooth muscle is preferably within the body of an animal. The type of smooth muscle to be relaxed includes, but is not limited to, gastrointestinal smooth muscle, anal sphincter smooth muscle, esophageal sphincter muscle, sphincter of Oddi, arterial smooth muscle, heart smooth muscle, pulmonary smooth muscle, kidney smooth muscle, uterine smooth muscle, vaginal smooth muscle, cervical smooth muscle, placental smooth muscle, and ocular smooth muscle. When the smooth muscle is gastrointestinal smooth muscle, the type of gastrointestinal smooth muscle includes, but is not limited to, the internal anal sphincter muscle.

When the smooth muscle is within the body of the animal, the invention includes a method of alleviating (e.g., reducing the incidence or severity) or inhibiting (e.g., reducing the likelihood of developing, or preventing) an arginase-related disorder in an animal. In a preferred embodiment, the animal is a human.

To alleviate an arginase-related disorder in a mammal, an arginase inhibitor described herein is administered to a mammal afflicted with the disorder. The inhibitor is preferably administered in combination with one or more pharmaceutically acceptable carriers, as described in further detail herein. The inhibitor (preferably in combination with a carrier) can also be administered to a mammal afflicted with a disorder characterized by aberrant nitric oxide synthase activity, or to one which exhibits normal (i.e. non-diseased) levels of arginase and nitric oxide synthase activities, but in which inhibition of arginase activity is desired. The invention also contemplates use of an arginase inhibitor in an in vitro arginase inhibition/smooth muscle relaxation functional assay, for the purpose of identifying compounds which affect smooth muscle function.

Accordingly, in certain embodiments, the invention is directed to methods of inhibiting arginase in a mammal, comprising the step of administering to said mammal an effective amount of a compound of the formulas described herein or a pharmaceutically acceptable salt thereof.

Accordingly, in certain embodiments, the invention is directed to methods of treating an arginase-related disorder in a mammal, comprising the step of administering to said mammal an effective amount of a compound of any of the formulas described herein or a pharmaceutically acceptable salt thereof. In certain preferred embodiments, the arginase-related disorder is a disorder associated with an abnormally low level of nitric oxide synthase activity in a tissue of the human, a disorder associated with an abnormally high level of arginase activity in a tissue of the human, or combinations thereof, including heart disease, systemic hypertension, pulmonary hypertension, erectile dysfunction, autoimmune encephalomyelitis, chronic renal failure, gastrointestinal motility disorders, gastric cancers, reduced hepatic blood flow, insufficient hepatic blood flow, cerebral vasospasm, or a combination thereof.

In still other certain embodiments, the invention is directed to methods of relaxing smooth muscle in a mammal, comprising the step of administering to said mammal an effective amount of a compound of the formulas described herein or a pharmaceutically acceptable salt thereof. In certain preferred embodiments, the smooth muscle which is relaxed according to this method is at least one selected from the group consisting of a gastrointestinal smooth muscle, anal sphincter smooth muscle, esophageal sphincter muscle, corpus cavernosum, sphincter of Oddi, arterial smooth muscle, heart smooth muscle, pulmonary smooth muscle, kidney smooth muscle, uterine smooth muscle, vaginal smooth muscle, cervical smooth muscle, placental smooth muscle, and ocular smooth muscle.

In certain embodiments, the invention is directed to methods of treating a disease or condition associated with upregulation of arginase in a mammal, comprising the step of administering to said mammal an effective amount of a compound of the formulas described herein or a pharmaceutically acceptable salt thereof; wherein said disease or condition is a gastrointestinal disease, a pulmonary inflammatory disease, a sexual arousal disorder, a cardiovascular disorder, a hemolytic disorder, an autoimmune disease, wound healing, a cancer, pre-term labor, psoriasis, or a combination thereof.

In certain embodiments, the invention is directed to methods of treating a disease or condition caused by parasitic protozoa, a disease caused by bacteria, or a combination thereof.

Inhibiting arginase impacts cancer in two ways. The first way is relief from immune-suppression that leads to tolerance of the tumor, and the second way is by restricting the production of ornithine and subsequent polyamines, which have a role in proliferation.

In certain preferred embodiments, the gastrointestinal disease is a gastrointestinal motility disorder, inflammatory bowel disease, Crohn's disease, ulcerative colitis, gastric ulcer, adenotonsilar disease or a combination thereof.

In certain preferred embodiments, the pulmonary inflammatory disease is asthma, chemically-induced lung fibrosis, idiopathic pulmonary fibrosis, cystic fibrosis, chronic obstructive pulmonary disease (COPD) or a combination thereof.

In certain preferred embodiments, the sexual arousal disorder is male erectile dysfunction, Peyronie's Disease, or a female sexual arousal disorder.

In certain preferred embodiments, the cardiovascular disorder is endothelial vascular dysfunction in atherosclerosis, hypertension, ischemia reperfusion injury, peripheral vascular disease, peripheral arterial disease, subarachnoid hemorrhage, hypercholesterolemia, diabetes, or a combination thereof, diabetic cardiovascular disease, pulmonary arterial hypertension, Reynaud's disease, or a combination thereof.

In certain preferred embodiments, the hemolytic disorder is paroxysmal nocturnal hemoglobinuria (PNH), sickle-cell disease, thalassemias, hereditary spherocytosis and stomatocytosis, microangiopathic hemolytic anemias, pyruvate kinase deficiency, ABO mismatch transfusion reaction, paroxysmal cold hemoglobinuria, severe idiopathic autoimmune hemolytic anemia, infection-induced anemia, malaria, cardiopulmonary bypass, mechanical heart valve-induced anemia, chemical induced anemia, or a combination thereof.

In certain preferred embodiments, the autoimmune disease is encephalomyelitis, multiple sclerosis, anti-phospholipid syndrome 1, autoimmune hemolytic anaemia, chronic inflammatory demyelinating polyradiculoneuropathy, dermatitis herpetiformis ("Celiac Disease"), dermatomyositis, myasthenia gravis, pemphigus, rheumatoid arthritis, stiff-person syndrome, type 1 diabetes, ankylosing spondylitis, or a combination thereof.

In certain preferred embodiments, the condition is wound healing.

In certain preferred embodiments, the disease caused by parasitic protozoa is African sleeping sickness, Chagas' disease, leishmaniasis, malaria, or a combination thereof.

In certain preferred embodiments, the cancer is renal cell carcinoma, prostate cancer, colorectal cancer, breast cancer, skin cancer, lung cancer, ovarian cancer, gastric cancer, or a combination thereof. In certain embodiments, the skin cancer is a squamous cell cancer, basal cell cancer, or a combination thereof.

In certain preferred embodiments, the condition is preterm labor.

In certain preferred embodiments, the condition is Reynaud's disease.

In certain embodiments, the invention is directed to methods of providing relief from immune suppression in a mammal, comprising the step of administering to said mammal an effective amount of a compound of the formulas described herein or a pharmaceutically acceptable salt thereof, wherein said mammal is suffering from a disease or condition selected from the group consisting of a chronic infectious disease, a bacterial infection, a parasitic infection, trauma, leprosy, tuberculosis, liver transplantation, a cancer, and combinations thereof.

In certain embodiments, the invention is directed to methods of inhibiting the production of ornithine or other related metabolites (e.g. agmatine, putrescine, spermine, spermidine, citruline, proline, glutamate, etc.) in a mammal suffering from at least one tumor, comprising the step of administering to said mammal an effective amount of a compound of the formulas described herein or a pharmaceutically acceptable salt thereof.

Pharmaceutical Compositions

Compounds described herein may be administered orally or parenterally. As formulated into a dosage form suitable for administration, the compounds described herein can be used as a pharmaceutical composition for the prevention, treatment, or remedy of the above diseases.

In clinical use of the compounds described herein, usually, the compound is formulated into various preparations together with pharmaceutically acceptable additives according to the dosage form, and may then be administered. By "pharmaceutically acceptable" it is meant the additive, carrier, diluent or excipient must be compatible with the other ingredients of the formulation and not deleterious to the recipient thereof. As such, various additives ordinarily used in the field of pharmaceutical preparations are usable. Specific examples thereof include gelatin, lactose, sucrose, titanium oxide, starch, crystalline cellulose, hydroxypropyl methylcellulose, carboxymethylcellulose, corn starch, microcrystalline wax, white petrolatum, magnesium metasilicate aluminate, anhydrous calcium phosphate, citric acid, trisodium citrate, hydroxypropylcellulose, sorbitol, sorbitan fatty acid ester, polysorbate, sucrose fatty acid ester, polyoxyethylene, hardened castor oil, polyvinylpyrrolidone, magnesium stearate, light silicic acid anhydride, talc, vegetable oil, benzyl alcohol, gum arabic, propylene glycol, polyalkylene glycol, cyclodextrin, hydroxypropyl cyclodextrin, and the like.

Preparations to be formed with those additives include, for example, solid preparations such as tablets, capsules, granules, powders and suppositories; and liquid preparations such as syrups, elixirs and injections. These may be formulated according to conventional methods known in the field of pharmaceutical preparations. The liquid preparations may also be in such a form that may be dissolved or suspended in water or in any other suitable medium in their use. Especially for injections, if desired, the preparations may be dissolved or suspended in physiological saline or glucose liquid, and a buffer or a preservative may be optionally added thereto.

The pharmaceutical compositions may contain the compound of the invention in an amount of from 1 to 99.9% by weight, preferably from 1 to 60% by weight of the composition. The compositions may further contain any other therapeutically-effective compounds.

In case where the compounds of the invention are used for prevention or treatment for the above-mentioned diseases, the dose and the dosing frequency may be varied, depending on the sex, the age, the body weight and the disease condition of the patient and on the type and the range of the intended remedial effect. In general, when orally administered, the dose may be from 0.001 to 50 mg/kg of body weight/day, and it may be administered at a time or in several times. In specific embodiments, the dose is from about 0.01 to about 25 mg/kg/day, in particular embodiments, from about 0.05 to about 10 mg/kg/day. For oral administration, the compositions are preferably provided in the form of tablets or capsules containing from 0.01 mg to 1,000 mg. In specific embodiments, the dose is 0.01, 0.05, 0.1, 0.2, 0.5, 1.0, 2.5, 5, 10, 15, 20, 25, 30, 40, 50, 75, 100, 125, 150, 175, 200, 225, 250, 500, 750, 850 or 1,000 milligrams of a compound described herein. This dosage regimen may be adjusted to provide the optimal therapeutic response.

Combination Therapy

The compounds of the present invention are further useful in methods for the prevention or treatment of the aforementioned diseases, disorders and conditions in combination with other therapeutic agents.

The compounds of the present invention may be used in combination with one or more other drugs in the treatment, prevention, suppression or amelioration of diseases or conditions for which compounds described herein or the other drugs may have utility, where the combination of the drugs together are safer or more effective than either drug alone. Such other drug(s) may be administered in an amount commonly used therefore, contemporaneously or sequentially with a compound described herein or a pharmaceutically acceptable salt thereof. When a compound described herein is used contemporaneously with one or more other drugs, the pharmaceutical composition may in specific embodiments contain such other drugs and the compound described herein or its pharmaceutically acceptable salt in unit dosage form. However, the combination therapy may also include therapies in which the compound described herein or its pharmaceutically acceptable salt and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound described herein or a pharmaceutically acceptable salt thereof.

Examples of other active ingredients that may be administered in combination with a compound of any of the Formulas described herein or a pharmaceutically acceptable salt thereof and either administered separately or in the same pharmaceutical composition, include, but are not limited to pain relieving agents, anti-angiogenic agents, anti-neoplastic agents, anti-diabetic agents, anti-infective agents, or gastrointestinal agents, or combinations thereof.

Suitable compounds that may be used in combination with a compound according to the present invention include without limitation sildenafil, vardenafil, tadalafil and alprostadil, epoprostenol, iloprost, bosentan, amlodipine, diltiazem, nifedipine, ambrisentan and warfarin, fluticasone, budesonide, mometasone, flunisolide, beclomethasone, montelukast, zafirlukast, zileuton, salmeterol, formoterol, theophylline, albuterol, levalbuterol, pirbuterol, ipratropium, prednisone, methylprednisolone, omalizumab, corticosteroid and cromolyn, atorvastatin, lovastatin, simvastatin, pravastatin, fluvastatin, rosuvastatin, gemfibrozil, fenofibrate, nicotinic acid, clopidogrel and pharmaceutically acceptable salts thereof.

Additionally, a compound of any of the Formulas disclosed herein may be used in combination with one or more other active agents, including but not limited to, other anti-cancer agents that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

Examples of vascular endothelial growth factor (VEGF) receptor inhibitors include, but are not limited to, bevacizumab (sold under the trademark AVASTIN by Genentech/Roche), axitinib, (N-methyl-2-[[3-[([pound])-2-pyridin-2-ylethenyl]-1H-indazol-6-yl]sulfanyl]benzamide, also known as AG013736, and described in PCT Publication No. WO01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indol-6-yl)-2-[(4-pyridinyimethy)amino]-3-pyridinecarboxamide. and described in PCT Publication No. WO 02/068470), pasireotide (also known as SO 230, and described in PCT Publication No. WO02/010192), and sorafenib (sold under the tradename NEXAVAR).

Examples of topoisomerase II inhibitors include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX and MYLERAN), carboplatin (sold under the tradename PARAPLATIN), lomustine (also known as CCNU, sold under the tradename CeeNU), cisplatin (also known as CDDP, sold under the tradenames PLATINOL and PLATINOL-AQ), chlorambucil (sold under the tradename LEUKERAN), cyclophosphamide (sold under the tradenames CYTOXAN and NEOSAR), dacarbazine (also known as DTIC, DIC and imidazole carboxamide, sold under the tradename DTIC-DOME), altretamine (also known as hexamethylmelamine (HMM) sold under the tradename HEXALEN), ifosfamide (sold under the tradename IFEX), procarbazine (sold under the tradename MATULANE), mechlorethamine (also known as nitrogen mustard, mustine and mechloroethamine hydrochloride, sold under the tradename MUSTARGEN), streptozocin (sold under the tradename ZANOSAR), thiotepa (also known as thiophosphoamide, TESPA and TSPA, and sold under the tradename THIOPLEX).

Examples of anti-tumor antibiotics include, but are not limited to, doxorubicin (sold under the tradenames ADRIAMYCIN and RUB EX), bleomycin (sold under the tradename LENOXANE), daunorubicin (also known as dauorubicin hydrochloride, daunomycin, and rubidomycin hydrochloride, sold under the tradename CERUBIDINE), daunorubicin liposomal (daunorubicin citrate liposome, sold under the tradename DAUNOXOME), mitoxantrone (also known as DHAD, sold under the tradename NOVANTRONE), epirubicin (sold under the tradename ELLENCE), idarubicin (sold under the tradenames IDAMYCIN, IDAMYCIN PFS), and mitomycin C (sold under the tradename MUTAMYCIN).

Examples of anti-metabolites include, but are not limited to, claribine (2-chlorodeoxyadenosine, sold under the tradename LEUSTATIN), 5-fluorouracil (sold under the tradename ADRUCIL), 6-thioguanine (sold under the tradename PURINETHOL), pemetrexed (sold under the tradename ALIMTA), cytarabine (also known as arabinosylcytosine (Ara-C), sold under the tradename CYTOSAR-U), cytarabine liposomal (also known as Liposomal Ara-C, sold under the tradename DEPOCYT), decitabine (sold under the tradename DACOGEN), hydroxyurea (sold under the tradenames HYDREA, DROXIA and MYLOCEL), fludarabine (sold under the tradename FLUDARA), floxuridine (sold under the tradename FUDR), cladribine (also known as 2-chlorodeoxyadenosine (2-CdA) sold under the tradename LEUSTATIN), methotrexate (also known as amethopterin, methotrexate sodium (MTX), sold under the tradenames RHEUMATREX and TREXALL), and pentostatin (sold under the tradename NIPENT).

Examples of retinoids include, but are not limited to, alitretinoin (sold under the tradename PANRETIN), tretinoin (all-trans retinoic acid, also known as ATRA, sold under the tradename VESANOID), Isotretinoin (13-c/s-retinoic acid, sold under the tradenames ACCUTANE, AMNESTEEM, CLARAVIS, CLARUS, DECUTAN, ISO- TANE, IZOTECH, ORATANE, ISOTRET, and SOTRET), and bexarotene (sold under the tradename TARGRETIN).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP 005009. Human PD-L1 and PD-L2 amino acid sequences can be found in NCBI Locus No.: NP 054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')2, scFv and Fv fragments. Examples of PD-1 antagonists include, but are not limited to, pembrolizumab (sold under the tradename KEYTRUDA) and nivolumab (sold under the tradename OPDIVO).

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions described in WO2013/019906.

Other PD-1 antagonists useful in any of the treatment method, medicaments and uses of the present invention include an immunoadhesin that specifically binds to PD-1 or PD-LI, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, but are not limited to, arsenic trioxide (sold under the tradename TRISENOX), asparaginase (also known as L-asparaginase, and Erwinia L-asparaginase, sold under the tradenames ELSPAR and KIDROLASE)

When a compound of the present invention is used contemporaneously with one or more other drugs a specific embodiment hereof pertains to, a pharmaceutical composition containing such other drugs in addition to the compound of the present invention. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, in particular embodiments from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

EXAMPLES

The meanings of the abbreviations in Examples are shown below.

Boc-Ser(Bzl)-OH=N-(tert-Butoxycarbonyl)-O-benzyl-L-serine
CELITE=diatomaceous earth
$CF_3CH_2OH$=2,2,2-trifluoroethanol
$CH_3CN$=MeCN=acetonitrile
Conc.=concentrated
$CO_2$=carbon dioxide
DCM=dichloromethane
DIEA=DIPEA=N,N-diisopropylethylamine=Hünig's base
DMF=N,N-dimethylformamide
DMSO=dimethyl sulfoxide
DPPE=1,2-bis(diphenylphosphino)ethane
EtOAc=ethyl acetate
h=hours
$H_2$=hydrogen
$H_2O$=water
HATU=1-[bis(dimethylamino)methylene]-1H-1,2,3-triazolo[4,5-b]pyridinium 3-oxid hexafluorophosphate
HBr=hydrogen bromide
HCl=hydrochloric acid
HFBA=heptafluorobutyric acid
$K_2CO_3$=potassium carbonate
LCMS=liquid chromatography-mass spectrometry
LHMDS=LiHMDS=lithium bis(trimethylsilyl)amide
LiF=lithium fluoride
LiOH=lithium hydroxide
min=minutes
MeOH=methanol
$NaBH_4$=sodium borohydride NaCl=sodium chloride
NaHCO$_3$=sodium bicarbonate
Na$_2$SO$_4$=sodium sulfate
NH$_4$Cl=ammonium chloride
NH$_4$OH=ammonium hydroxide
Pd(OH)$_2$/C=Pearlman's catalysts=palladium hydroxide on carbon
SFC=supercritical fluid chromatography
TEA=triethylamine
TFA=trifluoroacetic acid
THF=tetrahydrofuran
1 Standard atmosphere [atm]=101325 pascal [Pa]=14.6959488 psi The meanings of the abbreviations in the nuclear magnetic resonance spectra are shown below:

s=singlet, d=doublet, dd=double doublet, dt=double triplet, ddd=double double doublet, Sept=septet, t=triplet, m=multiplet, br=broad, brs=broad singlet, q=quartet J=coupling constant and Hz=hertz.

Compounds of this invention can be prepared using the intermediates and processes outlined below. The various starting materials used are commercially available or are readily made by persons skilled in the art.

Intermediate I-1: 1-benzyl 2-methyl 3-(3-(4,4,5,5-tetramethyl-1,3,2-dioxaborolan-2-yl)propyl)-4,5-dihydro-1H-pyrrole-1,2-dicarboxylate

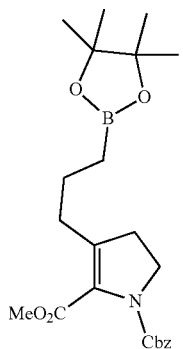

Step 1: 1-tert-butyl 2-methyl 3-bromo-1H-pyrrole-1,2-dicarboxylate

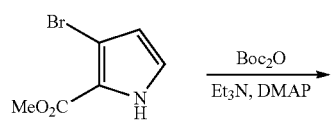

N,N-dimethylpyridin-4-amine (1.5 g, 12 mmol) was added to a solution of methyl 3-bromo-1H-pyrrole-2-carboxylate (5.0 g, 25 mmol), di-tert-butyl dicarbonate (8.0 g, 37 mmol) and triethylamine (14 mL, 98 mmol) in DCM (60 mL), and the reaction mixture was stirred at 25° C. for 2 h. The mixture was diluted with water and extracted with DCM, and the combined organic phase was washed with brine, dried over anhydrous Na$_2$SO$_4$, filtered, and concentrated under reduced pressure. The residue was purified by silica gel column chromatography (EtOAc in hexanes) to give 1-tert-butyl 2-methyl 3-bromo-1H-pyrrole-1,2-dicarboxylate. LCMS (C$_7$H$_7$BrNO$_4^+$) (ES, m/z): 248 [M-C$_4$H$_8$+H]$^+$.

Step 2: 1-tert-butyl 2-methyl 3-allyl-1H-pyrrole-1,2-dicarboxylate

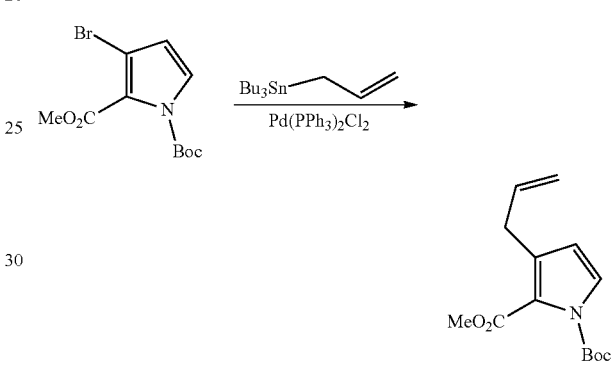

Bis(triphenylphosphine)-palladium (II) dichloride (0.99 g, 1.5 mmol) was added to a mixture of 1-tert-butyl 2-methyl 3-bromo-1H-pyrrole-1,2-dicarboxylate (3.0 g, 9.9 mmol), and allyltributylstannane (7.5 mL, 24 mmol) in DMF (65 mL), and the reaction mixture was stirred at 100° C. for 3 h under nitrogen. The mixture was quenched with 5% aqueous potassium fluoride, and stirred at 20° C. for 1 h, then extracted with EtOAc. The combined organic phase was dried over anhydrous Na$_2$SO$_4$, filtered and concentrated in vacuo. The residue was purified by silica gel column chromatography (EtOAc in hexanes) to give 1-tert-butyl 2-methyl 3-allyl-1H-pyrrole-1,2-dicarboxylate. LCMS (C$_{10}$H$_{12}$NO$_4^+$) (ES, m/z): 210 [M-C$_4$H$_8$+H]$^+$.

Step 3: 1-tert-butyl 2-methyl 3-(3-(4,4,5,5-tetramethyl-1,3,2-dioxaborolan-2-yl)propyl)-1H-pyrrole-1, 2-dicarboxylate

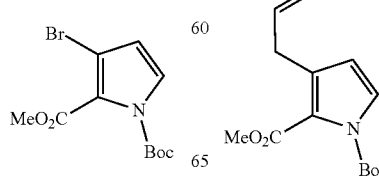
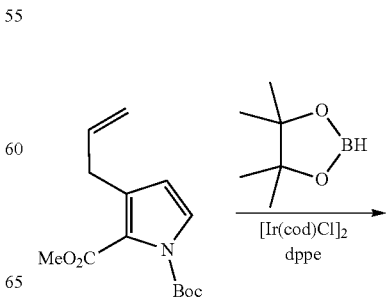

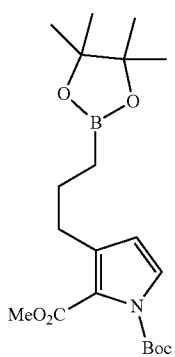

1-Tert-butyl 2-methyl 3-allyl-1H-pyrrole-1,2-dicarboxylate (2.2 g, 8.3 mmol) was added to a solution of 4,4,5,5-tetramethyl-1,3,2-dioxaborolane (3.6 mL, 25 mmol), chloro(1,5-cyclooctadiene)iridium (I) dimer (0.39 g, 0.58 mmol), and bis(diphenylphosphino)ethane (0.32 g, 0.83 mmol) in dry DCM (50 mL), and the reaction mixture was stirred at 20° C. for 13 h under nitrogen. The mixture was quenched with water and extracted with DCM, and the combined organic phase was dried over anhydrous Na$_2$SO$_4$, filtered and concentrated in vacuo. The residue was purified by silica gel column chromatography (EtOAc in hexanes) to give 1-tert-butyl 2-methyl 3-(3-(4,4,5,5-tetramethyl-1,3,2-dioxaborolan-2-yl)propyl)-1H-pyrrole-1,2-dicarboxylate. LCMS (C$_{16}$H$_{25}$BNO$_6^+$) (ES, m/z): 338 [M-C$_4$H$_8$+H]$^+$.

Step 4: 1-tert-butyl 2-methyl 3-(3-(4,4,5,5-tetramethyl-1,3,2-dioxaborolan-2-yl)propyl)pyrrolidine-1,2-dicarboxylate

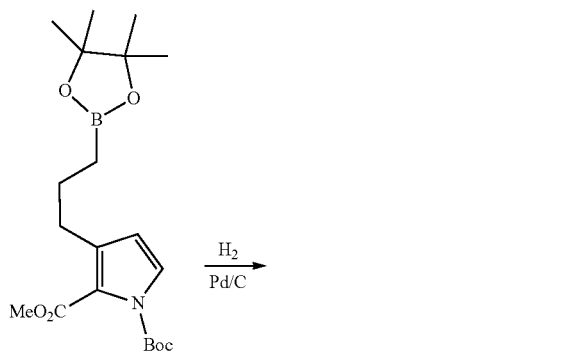

10% palladium on carbon (0.50 g, 0.21 mmol) was added to a solution of 1-tert-butyl 2-methyl 3-(3-(4,4,5,5-tetramethyl-1,3,2-dioxaborolan-2-yl)propyl)-1H-pyrrole-1,2-dicarboxylate (2.2 g, 5.6 mmol) in MeOH (35 mL) under nitrogen atmosphere, and the reaction mixture was degassed and backfilled with hydrogen (three times), and stirred under hydrogen (45-50 psi) at 45° C. for 12 h. The mixture was filtered and the filtrate was concentrated under reduced pressure, and the residue was purified by silica gel column chromatography (EtOAc in hexanes) to give 1-tert-butyl 2-methyl 3-(3-(4,4,5,5-tetramethyl-1,3,2-dioxaborolan-2-yl)propyl)pyrrolidine-1,2-dicarboxylate. LCMS (C$_{15}$H$_{29}$BNO$_4^+$) (ES, m/z): 298 [M-CO$_2$C$_4$H$_8$+H]$^+$.

Step 5: 3-(3-(4,4,5,5-tetramethyl-1,3,2-dioxaborolan-2-yl)propyl)pyrrolidine-2-carboxylate

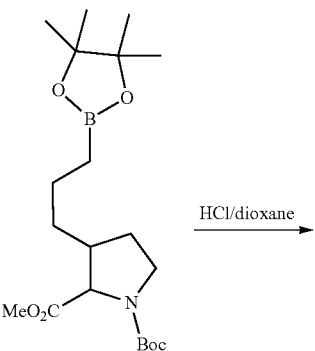

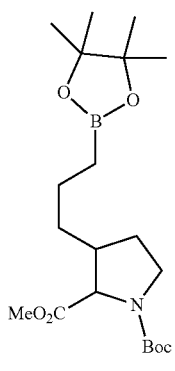

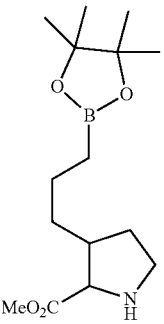

HCl in dioxane (4.0 M, 30 mL, 120 mmol) was added to a solution of 1-tert-butyl 2-methyl 3-(3-(4,4,5,5-tetramethyl-1,3,2-dioxaborolan-2-yl)propyl)pyrrolidine-1,2-dicarboxylate (3.2 g, 8.1 mmol) in DCM (30 mL) under nitrogen at 20° C., and the reaction mixture was stirred for 1 h at 20° C. The mixture was concentrated under reduced pressure to give methyl 3-(3-(4,4,5,5-tetramethyl-1,3,2-dioxaborolan-2-yl)propyl)pyrrolidine-2-carboxylate, which was used in next step without further purification. $^1$H NMR (400 MHz, CDCl$_3$) δ 4.39 (br s, 1H), 3.83 (s, 3H), 3.60-3.67 (m, 1H), 3.47 (br s, 1H), 2.59 (br s, 1H), 2.19 (br s, 1H), 1.75-1.83 (m, 1H), 1.62 (br s, 2H), 1.46 (br d, J=7.45 Hz, 2H), 1.23 (s, 12H), 0.78 (br s, 2H).

Step 6: 1-benzyl 2-methyl 3-(3-(4,4,5,5-tetramethyl-1,3,2-dioxaborolan-2-yl)propyl)pyrrolidine-1,2-dicarboxylate

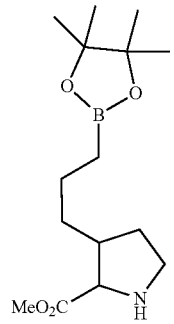

CbzCl, TEA
→

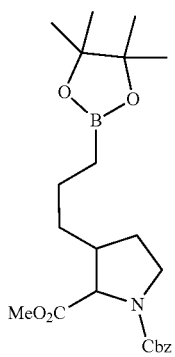

Benzyl chloroformate (1.5 mL, 10 mmol) was added to a stirred solution of methyl 3-(3-(4,4,5,5-tetramethyl-1,3,2-dioxaborolan-2-yl)propyl)pyrrolidine-2-carboxylate (2.4 g, 9.4 mmol) and triethylamine (3.9 mL, 28 mmol) in dry DCM (5 mL) at 0° C., and the reaction mixture was stirred for 3 h at 20° C. The mixture was quenched with saturated aqueous NH$_4$Cl and extracted with DCM, and the combined organic phase was washed with brine, dried over Na$_2$SO$_4$, filtered and concentrated. The residue was purified by silica gel column chromatography (EtOAc in hexanes) to give 1-benzyl 2-methyl 3-(3-(4,4,5,5-tetramethyl-1,3,2-dioxaborolan-2-yl)propyl)pyrrolidine-1,2-dicarboxylate. LCMS (C$_{23}$H$_{35}$BNO$_6$$^+$) (ES, m/z): 432 [M+H]$^+$.

Step 7: 1-benzyl 2-methyl 3-(3-(4,4,5,5-tetramethyl-1,3,2-dioxaborolan-2-yl)propyl)-4,5-dihydro-1H-pyrrole-1,2-dicarboxylate

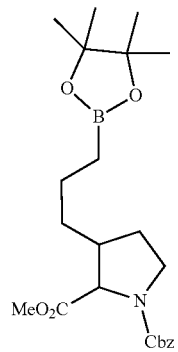

1) LiHMDS
2) Br$_2$
→

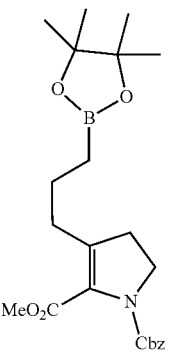

LiHMDS (1.0 M solution in toluene, 58 mL, 58 mmol) was added to a solution of 1-benzyl 2-methyl 3-(3-(4,4,5,5-tetramethyl-1,3,2-dioxaborolan-2-yl)propyl)pyrrolidine-1,2-dicarboxylate (12 g, 28 mmol) in THF (185 mL) at −78° C. The mixture was stirred at 0° C. for 30 min, then bromine (1.6 mL, 31 mmol) was added dropwise at −90° C. The mixture was gradually warm to room temperature, and stirred overnight at room temperature. The reaction was quenched with saturated aqueous NH$_4$Cl, and brine. The mixture was extracted with EtOAc twice. The combined organic layers were dried over Na$_2$SO$_4$, filtered and concentrated under reduced pressure. The residue was purified by silica gel column chromatography (EtOAc in hexanes) to provide 1-benzyl 2-methyl 3-(3-(4,4,5,5-tetramethyl-1,3,2-dioxaborolan-2-yl)propyl)-4,5-dihydro-1H-pyrrole-1,2-dicarboxylate. LCMS (C$_{23}$H$_{33}$BNO$_6$$^+$) (ES, m/z): 430 [M+H]$^+$.

Intermediate I-2: methyl (3aR,6aR)-3a-(3-(4,4,5,5-tetramethyl-1,3,2-dioxaborolan-2-yl)propyl)hexahydropyrrolo[3,4-b]pyrrole-6a(1H)-carboxylate

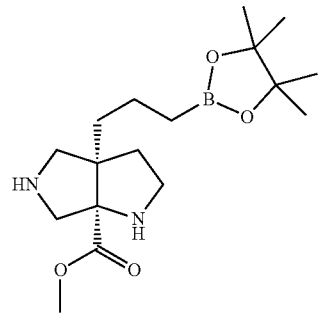 [SMILES: COC(=O)[C@]12CNC[C@@]1(CCCB1OC(C)(C)C(C)(C)O1)CCN2]

Step 1: 1-benzyl 6a-methyl 5-benzyl-3a-(3-(4,4,5,5-tetramethyl-1,3,2-dioxaborolan-2-yl)propyl)hexahydropyrrolo[3,4-b]pyrrole-1,6a-dicarboxylate

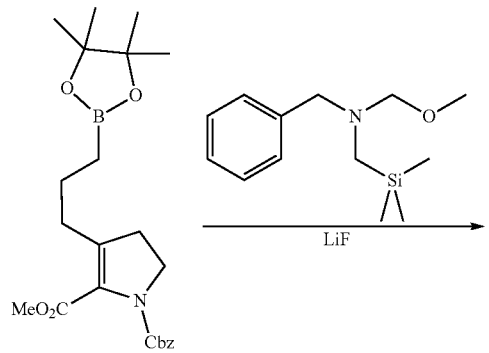

Step 2: 1-benzyl 6a-methyl (3aR,6aR)-5-benzyl-3a-(3-(4,4,5,5-tetramethyl-1,3,2-dioxaborolan-2-yl)propyl)hexahydropyrrolo[3,4-b]pyrrole-1,6a-dicarboxylate (P1) and (1-benzyl 6a-methyl (3aS,6aS)-5-benzyl-3a-(3-(4,4,5,5-tetramethyl-1,3,2-dioxaborolan-2-yl)propyl)hexahydropyrrolo[3,4-b]pyrrole-1,6a-dicarboxylate (P2)

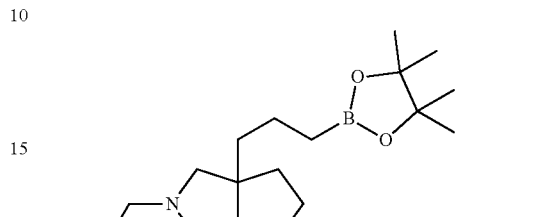

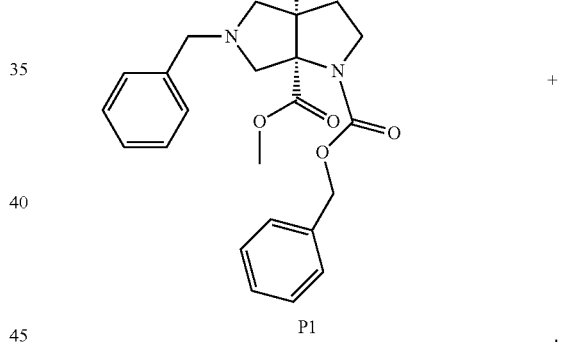

A solution N-benzyl-1-methoxy-N-((trimethylsilyl)methyl)methanamine (7.8 mL, 30 mmol) in DMF (4.0 mL) was added dropwise via a syringe pump (0.11 mL/min) to a stirred mixture of 1-benzyl 2-methyl 3-(3-(4,4,5,5-tetramethyl-1,3,2-dioxaborolan-2-yl)propyl)-4,5-dihydro-1H-pyrrole-1,2-dicarboxylate (1.0 g, 2.3 mmol), LiF (0.79 g, 30 mmol) and DMF (6.0 mL) with the internal temperature around 149° C. After the addition, the reaction mixture was cooled to room temperature, and diluted with EtOAc (100 mL). The mixture was washed with brine twice. The organic layer was dried over $Na_2SO_4$, filtered and concentrated under reduced pressure. The residue was purified by silica gel column chromatography (EtOAc in DCM) to provide 1-benzyl 6a-methyl 5-benzyl-3a-(3-(4,4,5,5-tetramethyl-1,3,2-dioxaborolan-2-yl)propyl)hexahydropyrrolo[3,4-b]pyrrole-1,6a-dicarboxylate. LCMS ($C_{32}H_{44}BN_2O_6^+$) (ES, m/z): 563 $[M+H]^+$.

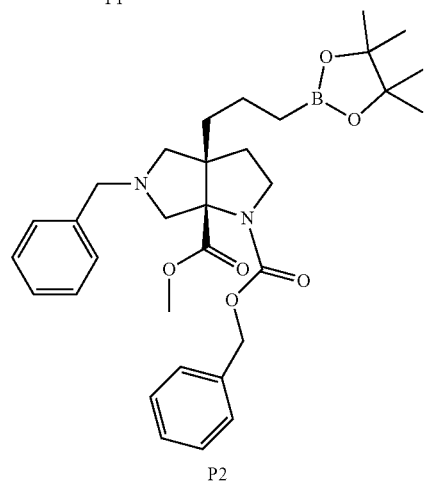

Racemic 1-benzyl 6a-methyl 5-benzyl-3a-(3-(4,4,5,5-tetramethyl-1,3,2-dioxaborolan-2-yl)propyl)hexahydropyrrolo[3,4-b]pyrrole-1,6a-dicarboxylate was resolved by Chiral-SFC [Column: Lux-2 (250 mm*21 mm), Mobile phase: A: $CO_2$, B: $CH_3CN$, Gradient: 25% of B. Flow Rate (mL/min) 70] to give 1-benzyl 6a-methyl (3aR,6aR)-5-benzyl-3a-(3-(4,4,5,5-tetramethyl-1,3,2-dioxaborolan-2-yl)propyl)hexahydropyrrolo[3,4-b]pyrrole-1,6a-dicarboxylate (P1, tr=5.83 min, analytical method: Chiral-SFC [Column: Lux-2 (250 mm*21 mm), Mobile phase: A: $CO_2$, B: MeOH with 0.1% $NH_4OH$. Gradient: 10% of B. Flow Rate (mL/min) 4) as the first eluting peak, and (1-benzyl 6a-methyl (3aS,6aS)-5-benzyl-3a-(3-(4,4,5,5-tetramethyl-1,3,2-dioxaborolan-2-yl)propyl)hexahydropyrrolo[3,4-b]pyrrole-1,6a-dicarboxylate (P2, tr=6.59 min, analytical method: Chiral-SFC [Column: Lux-2 (250 mm*21 mm), Mobile phase: A: $CO_2$, B: MeOH with 0.1% $NH_4OH$. Gradient: 10% of B. Flow Rate (mL/min) 4) as the second eluting peak. P1 LCMS ($C_{32}H_{44}BN_2O_6^+$) (ES, m/z): 563 $[M+H]^+$. P2 LCMS ($C_{32}H_{44}BN_2O_6^+$) (ES, m/z): 563 $[M+H]^+$.

Step 3: methyl (3aR,6aR)-3a-(3-(4,4,5,5-tetramethyl-1,3,2-dioxaborolan-2-yl)propyl)hexahydropyrrolo[3,4-b]pyrrole-6a(1H)-carboxylate, TFA Salt (P1, 7.6 g, 14 mmol) was evacuated under vacuum and refilled with nitrogen (three times). Palladium over carbon (10 wt %, 4.3 g, 4.1 mmol) was added, followed by MeOH (84 mL) and TFA (2.1 mL, 28 mmol). The mixture was evacuated under vacuum and refilled with hydrogen (three times). The reaction mixture was stirred under hydrogen (balloon) at room temperature for 2 h. The reaction mixture was filtered through a plug of CELITE. The filter cake was washed with MeOH. The combined filtrate was concentrated under reduced pressure to give methyl (3aR,6aR)-3a-(3-(4,4,5,5-tetramethyl-1,3,2-dioxaborolan-2-yl)propyl)hexahydropyrrolo[3,4-b]pyrrole-6a(1H)-carboxylate as a TFA salt, which was directly used in the next step without further purification. LCMS ($C_{17}H_{32}BN_2O_4^+$) (ES, m/z): 339 $[M+H]^+$.

Intermediate I-3: methyl (3aS,6aS)-3a-(3-(4,4,5,5-tetramethyl-1,3,2-dioxaborolan-2-yl)propyl)hexahydropyrrolo[3,4-b]pyrrole-6a(1H)-carboxylate

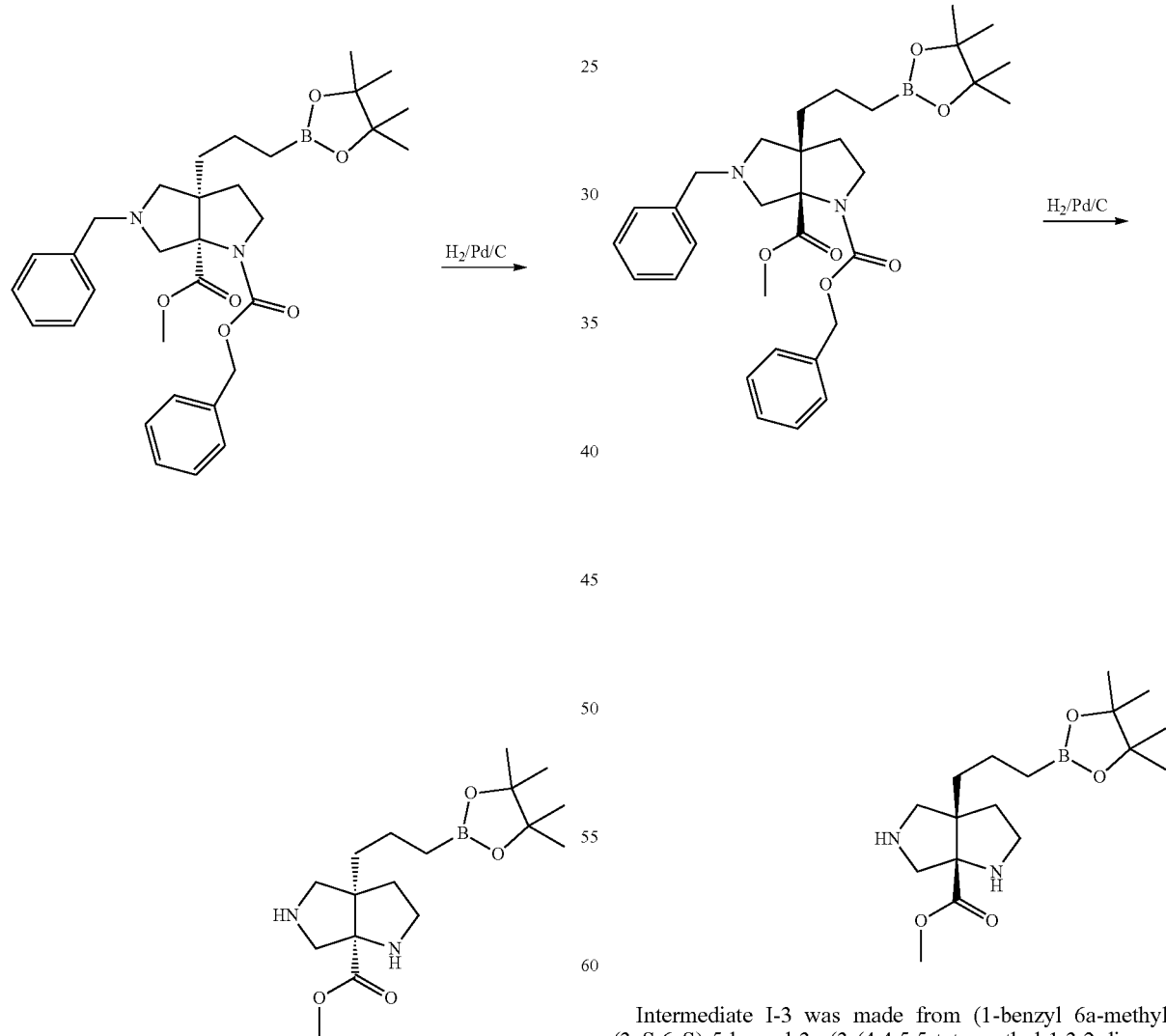
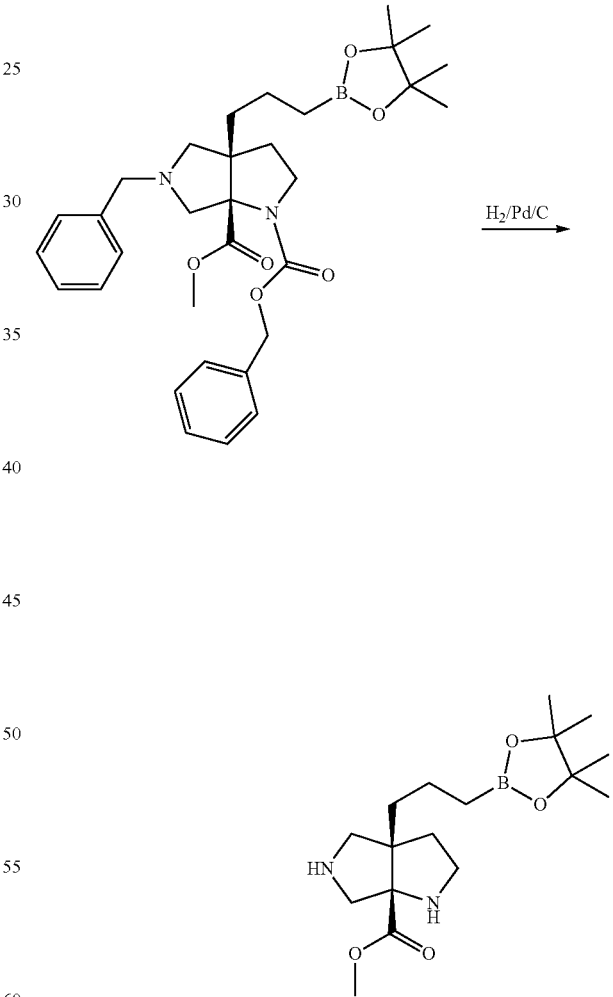

A flask containing 1-benzyl 6a-methyl (3aR,6aR)-5-benzyl-3a-(3-(4,4,5,5-tetramethyl-1,3,2-dioxaborolan-2-yl)propyl)hexahydropyrrolo[3,4-b]pyrrole-1,6a-dicarboxylate Intermediate I-3 was made from (1-benzyl 6a-methyl (3aS,6aS)-5-benzyl-3a-(3-(4,4,5,5-tetramethyl-1,3,2-dioxaborolan-2-yl)propyl)hexahydropyrrolo[3,4-b]pyrrole-1,6a-dicarboxylate (P2) using a similar procedure as Intermediate I-2 as a TFA salt. LCMS ($C_{17}H_{32}BN_2O_4^+$) (ES, m/z): 339 $[M+H]^+$.

Intermediate I-4: Racemic methyl 3a-(3-(4,4,5,5-tetramethyl-1,3,2-dioxaborolan-2-yl)propyl)hexahydropyrrolo[3,4-b]pyrrole-6a(1H)-carboxylate

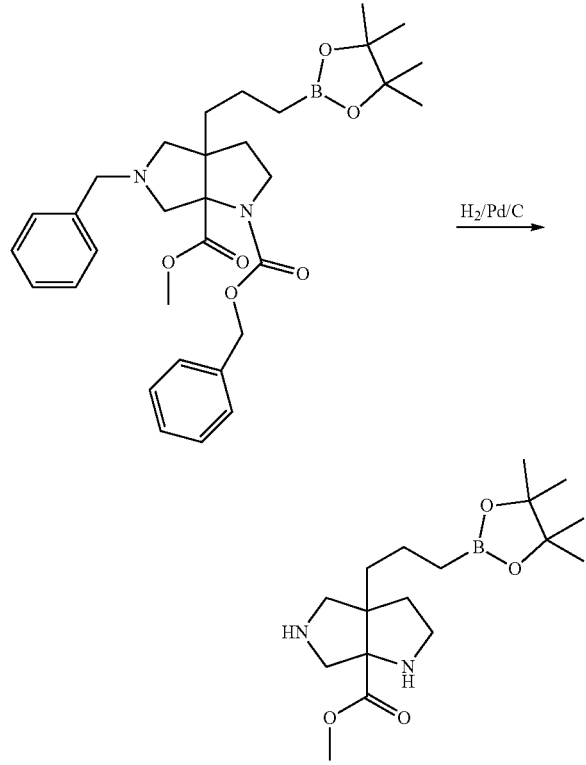

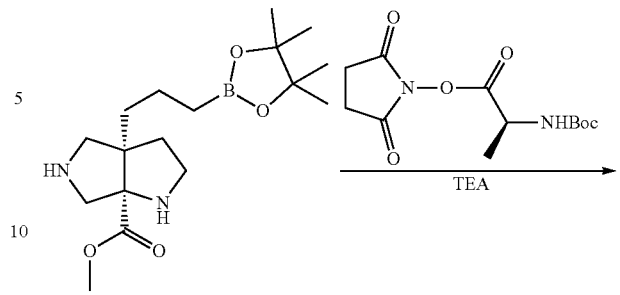

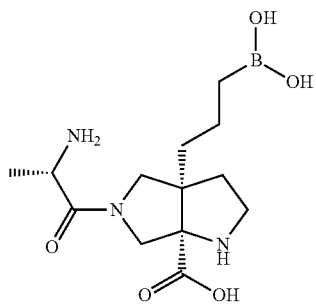 [SMILES: C[C@H](N)C(=O)N1C[C@@]2(CCCB(O)O)CCN[C@@]2(C(=O)O)C1]

Intermediate I-4 was made from racemic 1-benzyl 6a-methyl 5-benzyl-3a-(3-(4,4,5,5-tetramethyl-1,3,2-dioxaborolan-2-yl)propyl)hexahydropyrrolo[3,4-b]pyrrole-1,6a-dicarboxylate using a similar procedure as Intermediate I-2 as a TFA salt. LCMS ($C_{17}H_{32}BN_2O_4^+$) (ES, m/z): 339 [M+H]$^+$.

Example 1: (3aR,6aR)-5-(L-alanyl)-3a-(3-boronopropyl)hexahydropyrrolo[3,4-b]pyrrole-6a(H)-carboxylic acid Triethylamine (6.6 mL, 47 mmol) and 2,5-dioxopyrrolidin-1-yl (tert-butoxycarbonyl)-L-alaninate (4.7 g, 16 mmol) was added to a mixture of methyl (3aR,6aR)-3a-(3-(4,4,5,5-tetramethyl-1,3,2-dioxaborolan-2-yl)propyl)hexahydropyrrolo[3,4-b]pyrrole-6a(1H)-carboxylate (I-2, TFA salt, 7.7 g, 14 mmol) in DCM (104 mL). The reaction mixture was stirred overnight at room temperature. The reaction was quenched with water and saturated aq. NH$_4$Cl, and diluted with DCM. The mixture was stirred for 10 min. The organic layer was washed with water twice, and brine. The organic layer was dried over Na$_2$SO$_4$, filtered and concentrated under reduced pressure. The residue was purified by silica gel column chromatography (MeOH in DCM) to provide methyl (3aR,6aR)-5-((tert-butoxycarbonyl)-L-alanyl)-3a-(3-(4,4,5,5-tetramethyl-1,3,2-dioxaborolan-2-yl)propyl)hexahydropyrrolo[3,4-b]pyrrole-6a(1H)-carboxylate. LCMS ($C_{25}H_{45}BN_3O_7^+$) (ES, m/z): 510 [M+H]$^+$.

Step 2: (3aR,6aR)-3a-(3-boronopropyl)-5-((tert-butoxycarbonyl)-L-alanyl)hexahydropyrrolo[3,4-b]pyrrole-6a(1H)-carboxylic acid

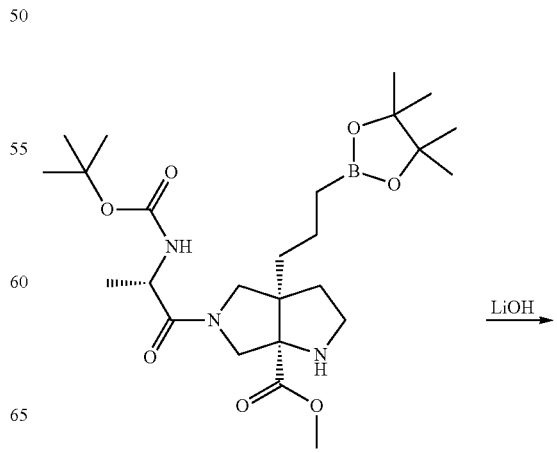

Step 1: methyl (3aR,6aR)-5-((tert-butoxycarbonyl)-L-alanyl)-3a-(3-(4,4,5,5-tetramethyl-1,3,2-dioxaborolan-2-yl)propyl)hexahydropyrrolo[3,4-b]pyrrole-6a(1H)-carboxylate -continued

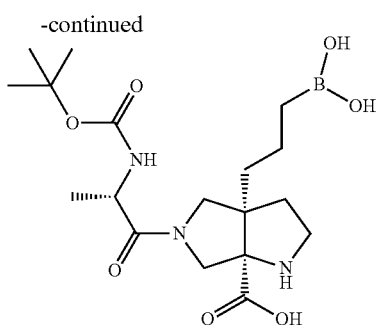

LiOH (52 mL, 52 mmol, 1.0 M aqueous solution) was added to a solution of methyl (3aR,6aR)-5-((tert-butoxycarbonyl)-L-alanyl)-3a-(3-(4,4,5,5-tetramethyl-1,3,2-dioxaborolan-2-yl)propyl)hexahydropyrrolo[3,4-b]pyrrole-6a (1H)-carboxylate (5.3 g, 10.4 mmol) in THF (107 mL) and MeOH (53 mL). The mixture was stirred at room temperature overnight. Water (52 mL) was added and the organic solvent was evaporated under reduced pressure with water bath temperature at room temperature. Then the aqueous layer was extracted with EtOAc three times. The aqueous layer containing (3aR,6aR)-3a-(3-boronopropyl)-5-((tert-butoxycarbonyl)-L-alanyl)hexahydropyrrolo[3,4-b]pyrrole-6a(1H)-carboxylic acid was used in the next step without further purification. Another batch of (3aR,6aR)-3a-(3-boronopropyl)-5-((tert-butoxycarbonyl)-L-alanyl)hexahydropyrrolo[3,4-b]pyrrole-6a(1H)-carboxylic acid (4.3 mmol) was prepared using a similar procedure. These two batches were combined and used in the next step. LCMS $(C_{18}H_{31}BN_3O_6^+)$ (ES, m/z): 396 $[M-H_2O+H]^+$.

Step 3: (3aR,6aR)-5-(L-alanyl)-3a-(3-boronopropyl) hexahydropyrrolo[3,4-b]pyrrole-6a(1H)-carboxylic acid

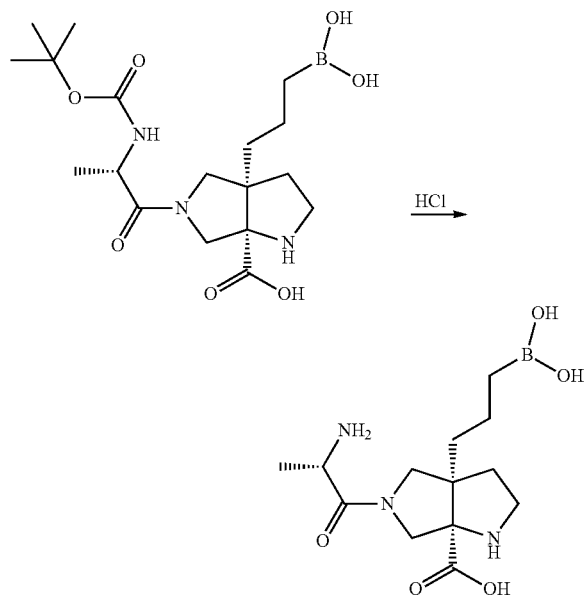

37% HCl in water (50 mL, 609 mmol) was added to (3aR,6aR)-3a-(3-boronopropyl)-5-((tert-butoxycarbonyl)-L-alanyl)hexahydropyrrolo[3,4-b]pyrrole-6a(1H)-carboxylic acid (15 mmol, aqueous solution prepared from previous step) at 0° C. dropwise. The mixture was stirred at room temperature for 5 min then at 50° C. for 70 min. The mixture was evaporated under reduced pressure with water bath temperature below 45° C. 120 mL of water was added, and the aqueous layer was washed with DCM (70 mL, five times). The aqueous layer containing the crude product was evaporated under reduced pressure for 5 min with water bath temperature below 45° C. to remove the residual DCM. DOWEX 50WX8 resin (120 g) was washed successively with MeOH (120 mL×4) and deionized water (120 mL×4). The resultant resin was then added to the aqueous solution of the crude product. The mixture was stirred very slowly for 60 min. The resin was washed with MeOH (120 mL×2), deionized water (120 mL×3). Then the resin was washed with 2N NH4OH (aqueous, 120 mL×4). The combined NH4OH solution was lyophilized to give (3aR,6aR)-5-(L-alanyl)-3a-(3-boronopropyl)hexahydropyrrolo[3,4-b]pyrrole-6a(1H)-carboxylic acid as free base. The title compound was obtained as a 3:2 mixture of rotamers at room temperature. LCMS $(C_{13}H_{23}BN_3O_4^+)$ (ES, m/z): 296 $[M-H_2O+H]^+$. $^1$HNMR (499 MHz, Deuterium Oxide) δ 4.15 (d, J=12.0 Hz, 0.4H), 4.07 (d, J=13.4 Hz, 0.6H), 3.42 (q, J=6.8 Hz, 1H), 3.80 (d, J=12.1 Hz, 0.4H), 3.76 (d, J=11.0 Hz, 0.6H), 3.69 (d, J=12.4 Hz, 0.4H), 3.62 (d, J=11.1 Hz, 0.6H), 3.60 (d, J=13.4 Hz, 0.6H), 3.44 (d, J=12.5 Hz, 0.4H), 3.41-3.31 (m, 1H), 3.18 (ddd, J=11.9, 8.6, 5.7 Hz, 0.6H), 3.11 (dt, J=11.68, 7.57 Hz, 0.4H), 2.19 (ddd, J=13.7, 8.1, 5.7 Hz, 0.6H), 2.06 (ddd, J=13.2, 8.1, 7.0 Hz, 0.4H), 1.99-1.91 (m, 1H), 1.54-1.24 (m, 4H), 1.32 (d, J=3.4 Hz, 2H), 1.31 (d, J=3.3 Hz, 1H), 0.86-0.73 (m, 2H)

Example 2: (3aR,6aR)-5-(L-alanyl)-3a-(3-boronopropyl)hexahydropyrrolo[3,4-b]pyrrole-6a(H)-carboxylic acid (HCl Salt)

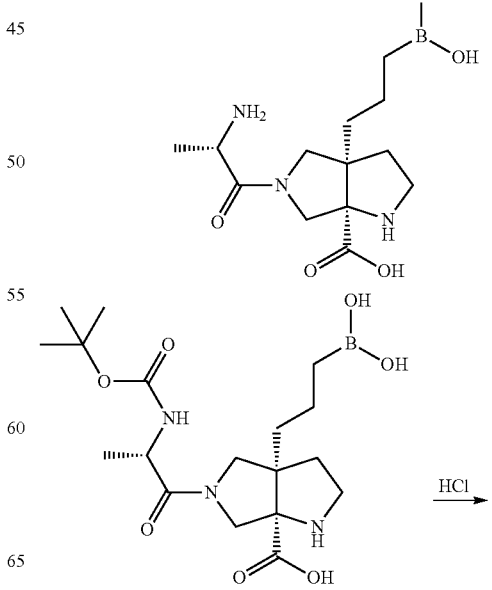

-continued

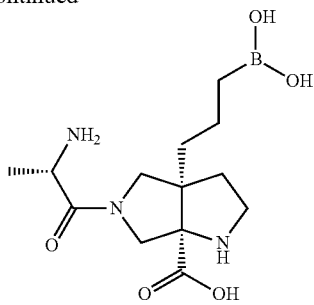

A mixture of HCl in water (6.0 N, 2.0 mL, 12 mmol) and (3aR,6aR)-3a-(3-boronopropyl)-5-((tert-butoxycarbonyl)-L-alanyl)hexahydropyrrolo[3,4-b]pyrrole-6a(1H)-carboxylic acid (60 mg, 0.12 mmol) was irradiated in a microwave oven at 90° C. for 30 min. The mixture was then cooled to room temperature, diluted with water (4 mL), and extracted with dichloromethane (5 mL×5). The aqueous layer was concentrated under reduced pressure. The residue was purified by RP-HPLC (Column: Waters Atlantis T3 19×250 mm Sum, water (20 mM HFBA and 0.1% TFA)-CH$_3$CN), and lyophilized to afford product. The product was dissolved in HCl (2.0 N aqueous, 2.0 mL, 4.0 mmol) and lyophilized to give (3aR,6aR)-5-(L-alanyl)-3a-(3-boronopropyl)hexahydropyrrolo[3,4-b]pyrrole-6a(1H)-carboxylic acid as a HCl salt. The title compound was obtained as a 2:1 mixture of rotamers at room temperature. LCMS ($C_{13}H_{23}BN_3O_4^+$) (ES, m/z): 296 [M–H$_2$O+H]$^+$. $^1$H NMR (499 MHz, Deuterium Oxide) δ 4.39-4.32 (m, 1.66H), 4.29 (d, J=14.1 Hz, 0.66H), 4.12 (d, J=12.7 Hz, 0.33H), 3.91 (d, J=14.0 Hz, 0.66H), 3.85-3.80 (m, 0.66H), 3.74 (d, J=11.1 Hz, 0.66H), 3.69-3.59 (m, 1H), 3.58-3.50 (m, 1H), 2.37 (ddd, J=14.0, 8.0, 6.0 Hz, 0.66H), 2.27 (dt, J=14.7, 7.6 Hz, 0.33H), 2.17 (dt, J=10.3, 4.2 Hz, 1H), 1.55-1.46 (m, 6.33H), 1.46-1.36 (m, 0.66H), 0.86-0.79 (m, 2H)

Example 3: (3aR,6aR)-3a-(3-boronopropyl)-5-glycylhexahydropyrrolo[3,4-b]pyrrole-6a(H)-carboxylic acid (HFBA Salt)

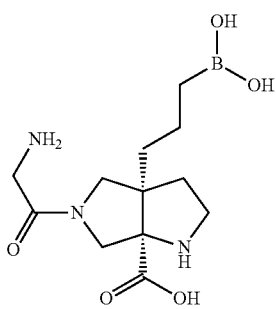 [SMILES: NCC(=O)N1C[C@@]2(CCCB(O)O)CCN[C@@]2(C(=O)O)C1]

Step 1: methyl (3aR,6aR)-5-((tert-butoxycarbonyl)glycyl)-3a-(3-(4,4,5,5-tetramethyl-1,3,2-dioxaborolan-2-yl)propyl)hexahydropyrrolo[3,4-b]pyrrole-6a(1H)-carboxylate

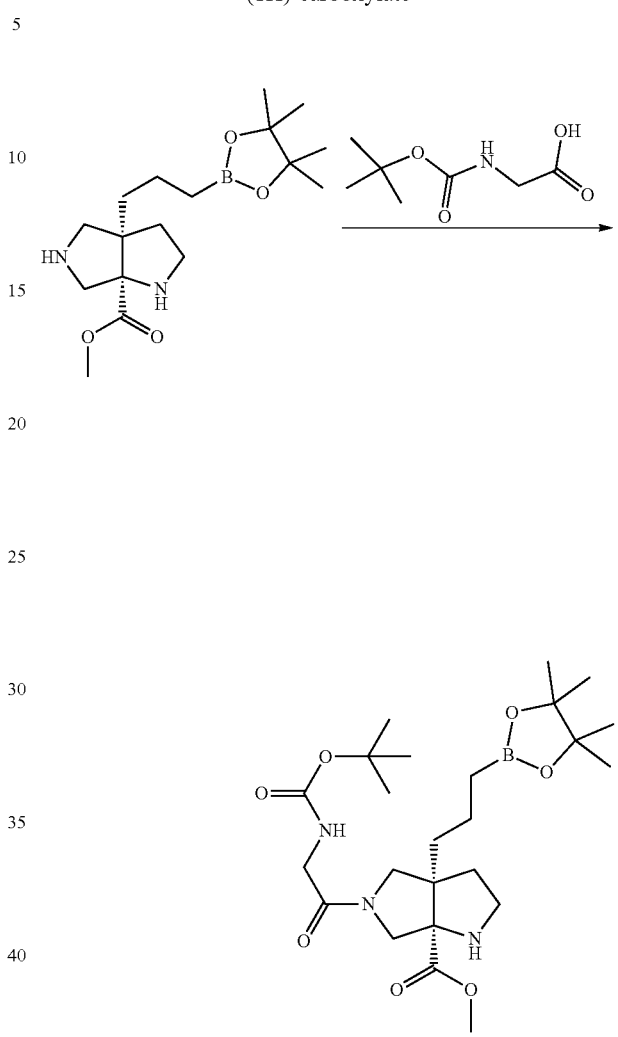

HATU (202 mg, 0.53 mmol) was added to a solution of (tert-butoxycarbonyl)glycine (78 mg, 0.44 mmol) in DCM (8.9 mL). The reaction mixture was stirred for a few minutes. Then methyl (3aR,6aR)-3a-(3-(4,4,5,5-tetramethyl-1,3,2-dioxaborolan-2-yl)propyl)hexahydropyrrolo[3,4-b]pyrrole-6a(1H)-carboxylate (I-2, 150 mg, 0.44 mmol), and DIEA (271 µL, 1.6 mmol) was added. The reaction was stirred at room temperature for 2 h. The reaction was diluted with ethyl acetate. The organic layer was washed with water, brine, saturated aqueous NaHCO$_3$ solution. The organic layer was dried over Na$_2$SO$_4$, filtered and concentrated under reduced pressure. The residue was purified by silica gel column chromatography (MeOH in DCM) to provide methyl (3aR,6aR)-5-((tert-butoxycarbonyl)glycyl)-3a-(3-(4,4,5,5-tetramethyl-1,3,2-dioxaborolan-2-yl)propyl)hexahydropyrrolo[3,4-b]pyrrole-6a(1H)-carboxylate. LCMS ($C_{24}H_{43}BN_3O_7^+$) (ES, m/z): 496 [M+H]$^+$.

Step 2: (3aR,6aR)-3a-(3-boronopropyl)-5-((tert-butoxycarbonyl)glycyl)hexahydropyrrolo[3,4-b]pyrrole-6a(1H)-carboxylic acid

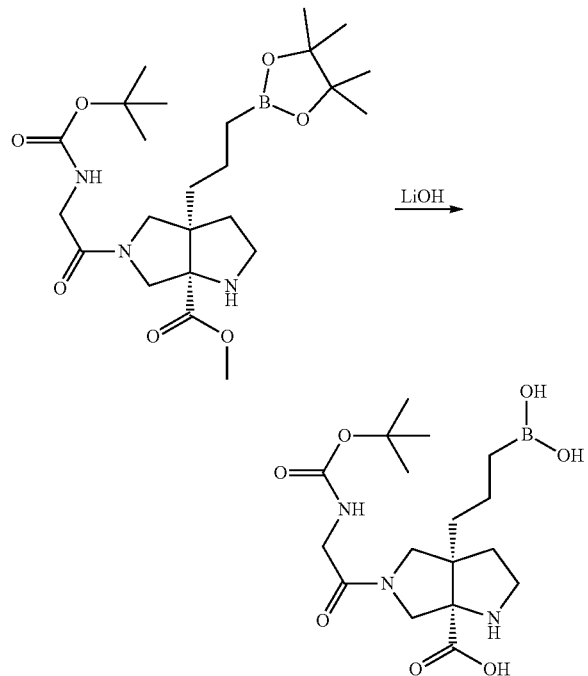

LiOH (6.7 mL, 6.7 mmol, 1.0 M in water) was added to a solution of methyl (3aR,6aR)-5-((tert-butoxycarbonyl)glycyl)-3a-(3-(4,4,5,5-tetramethyl-1,3,2-dioxaborolan-2-yl)propyl)hexahydropyrrolo[3,4-b]pyrrole-6a(1H)-carboxylate (220 mg, 0.44 mmol) in THF (4.6 mL) and MeOH (2.3 mL). The mixture was stirred at room temperature overnight. The organic solvents were evaporated under reduced pressure with water bath temperature at room temperature. Then water was added and the aqueous layer was extracted with EtOAc twice. The aqueous layer containing (3aR,6aR)-3a-(3-boronopropyl)-5-((tert-butoxycarbonyl)glycyl)hexahydropyrrolo[3,4-b]pyrrole-6a(1H)-carboxylic acid was used in the next step without further purification. LCMS $(C_{17}H_{29}BN_3O_6^+)$ (ES, m/z): 382 [M−H$_2$O+H]$^+$.

Step 3: (3aR,6aR)-3a-(3-boronopropyl)-5-glycyl-hexahydropyrrolo[3,4-b]pyrrole-6a(H)-carboxylic acid (HFBA Salt)

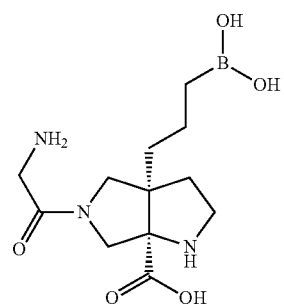

37% HCl in water (216 μL, 2.6 mmol) was added to (3aR,6aR)-3a-(3-boronopropyl)-5-((tert-butoxycarbonyl)glycyl)hexahydropyrrolo[3,4-b]pyrrole-6a(1H)-carboxylic acid (25 mg, 0.063 mmol) in water (935 μL) at 0° C. dropwise. The mixture was stirred at room temperature for 5 min then at 50° C. for 70 min. The mixture was evaporated with water bath temperature below 45° C. The residue was purified by RP-HPLC (Column: Waters Atlantis T3 19×250 mm 5 um, water (20 mM HFBA and 0.1% TFA)-CH$_3$CN), and lyophilized to give (3aR,6aR)-3a-(3-boronopropyl)-5-glycylhexahydropyrrolo[3,4-b]pyrrole-6a(1H)-carboxylic acid as a HFBA salt. The title compound was obtained as a 1:1 mixture of rotamers at room temperature. LCMS $(C_{12}H_{21}BN_3O_4^+)$ (ES, m/z): 282 [M−H$_2$O+H]$^+$. $^1$H NMR (499 MHz, Deuterium Oxide) δ 4.14 (d, J=13.2 Hz, 1H), 4.07 (d, J=16.7 Hz, 1H), 3.95 (d, J=16.7 Hz, 1H), 3.86 (d, J=13.1 Hz, 1H), 3.91-3.81 (m, 2H), 3.73 (ddd, J=11.0, 9.2, 7.0 Hz, 1H), 3.56 (d, J=12.8 Hz, 1H), 3.37 (d, J=12.7 Hz, 1H), 2.22 (ddd, J=10.3, 7.0, 3.5 Hz, 1H), 2.19-2.10 (m, 1H), 1.61-1.43 (m, 1H), 1.51-1.40 (m, 3H), 0.83 (t, J=7.0 Hz, 2H)

Example 4: (3aR,6aR)-3a-(3-boronopropyl)hexahydropyrrolo[3,4-b]pyrrole-6a(1H)-carboxylic acid (HFBA Salt)

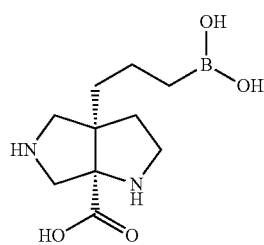

-continued

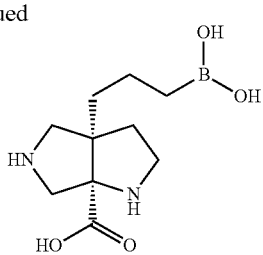

(3aR,6aR)-methyl 3a-(3-(4,4,5,5-tetramethyl-1,3,2-dioxaborolan-2-yl)propyl)octahydropyrrolo[3,4-b]pyrrole-6a-carboxylate (I-2, 75 mg, 0.22 mmol) in a microwave vial was dissolved in a mixture of 37% HCl in water:acetic acid:water (2:1:1, 3.0 mL) and irradiated in a microwave at 130° C. for 90 min. The mixture was then cooled to room temperature, diluted with water (4 mL), and extracted with dichloromethane (5 mL×5). The aqueous layer was concentrated under reduced pressure. The residue was purified by RP-HPLC (Column: Waters Atlantis T3 19×250 mm 5um, water (20 mM HFBA and 0.1% TFA)-CH$_3$CN), and lyophilized to give (3aR,6aR)-3a-(3-boronopropyl)hexahydropyrrolo[3,4-b]pyrrole-6a(1H)-carboxylic acid as a HFBA salt. LCMS (C$_{10}$H$_{15}$BN$_2$O$_3{}^+$) (ES, m/z): 225 [M−H$_2$O+H]$^+$. $^1$H NMR (499 MHz, Deuterium Oxide) δ 4.18 (d, J=13.7 Hz, 1H), 3.78-3.72 (m, 1H), 3.71 (d, J=13.7 Hz, 1H), 3.68-3.60 (m, 1H), 3.60-3.36 (m, 2H), 2.41-2.12 (m, 2H), 1.70-1.55 (m, 1H), 1.54-1.44 (m, 2H), 1.42-1.32 (m, 1H), 0.82 (t, J=7.5 Hz, 2H).

Example 5: (3aS,6aS)-3a-(3-boronopropyl)hexahydropyrrolo[3,4-b]pyrrole-6a(H)-carboxylic acid (HFBA salt) was prepared using a similar procedure as Example 4 using methyl (3aS,6aS)-3a-(3-(4,4,5,5-tetramethyl-1,3,2-dioxaborolan-2-yl)propyl)hexahydropyrrolo[3,4-b]pyrrole-6a(1H)-carboxylate (I-3)

Example 6: racemic 3a-(3-boronopropyl)hexahydropyrrolo[3,4-b]pyrrole-6a(H)-carboxylic acid (HFBA salt) was prepared using a similar procedure as Example 4 using racemic methyl 3a-(3-(4,4,5,5-tetramethyl-1,3,2-dioxaborolan-2-yl)propyl)hexahydropyrrolo[3,4-b]pyrrole-6a(1H)-carboxylate (I-4).

| Example # | Structure | Chemical Name | Mass [M − H$_2$O + H]+ | $^1$HNMR |
|---|---|---|---|---|
| 5 | 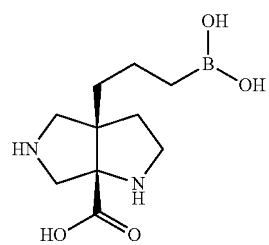 [SMILES: O=C(O)[C@@]12CNC[C@]1(CCCB(O)O)CCN2] | (3aS,6aS)-3a-(3-boronopropyl)hexahydropyrrolo[3,4-b]pyrrole-6a(1H)-carboxylic acid, HFBA salt | 225 | $^1$H NMR (499 MHz, Deuterium Oxide) δ 4.18 (d, J = 13.7 Hz, 1H), 3.78-3.72 (m, 1H), 3.71 (d, J = 13.7 Hz, 1H), 3.68-3.60 (m, 1H), 3.60-3.36 (m, 2H), 2.41-2.12 (m, 2H), 1.70-1.55 (m, 1H), 1.54-1.44 (m, 2H), 1.42-1.32 (m, 1H), 0.82 (t, J = 7.5 Hz, 2H) |
| 6 | 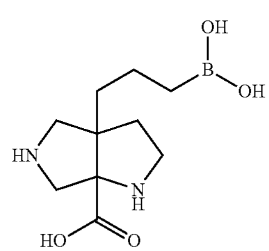 [SMILES: O=C(O)C12CNCC1(CCCB(O)O)CCN2] | racemic 3a-(3-boronopropyl)hexahydropyrrolo[3,4-b]pyrrole-6a(1H)-carboxylic acid, HFBA salt | 225 | $^1$H NMR (499 MHz, Deuterium Oxide) δ 4.18 (d, J = 13.7 Hz, 1H), 3.78-3.72 (m, 1H), 3.71 (d, J = 13.7 Hz, 1H), 3.68-3.60 Hz, 1H), 3.60-3.36 (m, 2H), 2.41-2.12 (m, 2H), 1.70-1.55 (m, 1H), 1.54-1.44 (m, 2H), 1.42-1.32 (m, 1H), 0.82 (t, J = 7.5 Hz, 2H) |

Example 7: Racemic 3a-(3-boronopropyl)-5-methyl-hexahydropyrrolo[3,4-b]pyrrole-6a(1H)-carboxylic acid (HFBA Salt)

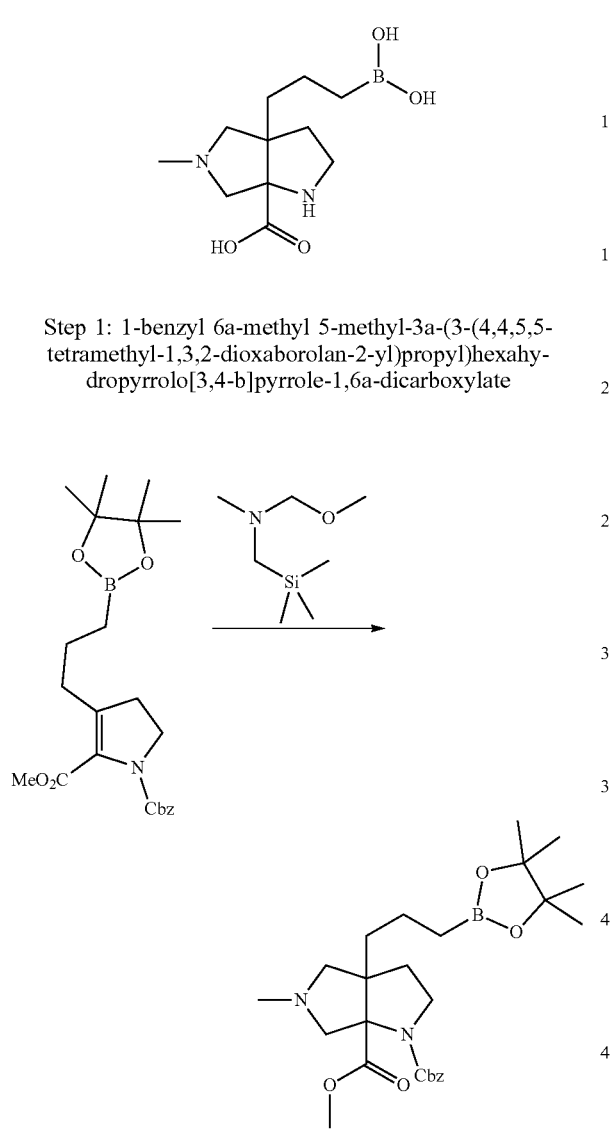

Step 1: 1-benzyl 6a-methyl 5-methyl-3a-(3-(4,4,5,5-tetramethyl-1,3,2-dioxaborolan-2-yl)propyl)hexahydropyrrolo[3,4-b]pyrrole-1,6a-dicarboxylate A solution of 1-methoxy-N-methyl-N-((trimethylsilyl)methyl)methanamine (0.94 g, 5.8 mmol) and 1-benzyl 2-methyl 3-(3-(4,4,5,5-tetramethyl-1,3,2-dioxaborolan-2-yl)propyl)-4,5-dihydro-1H-pyrrole-1,2-dicarboxylate (I-1, 1.0 g, 2.3 mmol) in acetonitrile (23 mL) was stirred at room temperature for 20 minutes. LiF (0.30 g, 12 mmol) and the mixture was irradiated in a microwave at 165° C. for 4 h. 1-methoxy-N-methyl-N-((trimethylsilyl)methyl)methanamine (0.94 g, 5.8 mmol) and LiF (0.30 g, 12 mmol) were added and reaction was irradiated in a microwave at 165° C. for 1 h. The reaction was cooled to room temperature and filtered. The solvent was concentrated under reduced pressure. The residue was purified by silica gel column chromatography (EtOAc in hexanes) to provide racemic 1-benzyl 6a-methyl 5-methyl-3a-(3-(4,4,5,5-tetramethyl-1,3,2-dioxaborolan-2-yl)propyl)hexahydropyrrolo[3,4-b]pyrrole-1,6a-dicarboxylate. LCMS ($C_{26}H_{40}BN_2O_6^+$) (ES, m/z): 487 [M+H]$^+$.

Step 2: Racemic 3a-(3-boronopropyl)-5-methyl-hexahydropyrrolo[3,4-b]pyrrole-6a(1H)-carboxylic acid

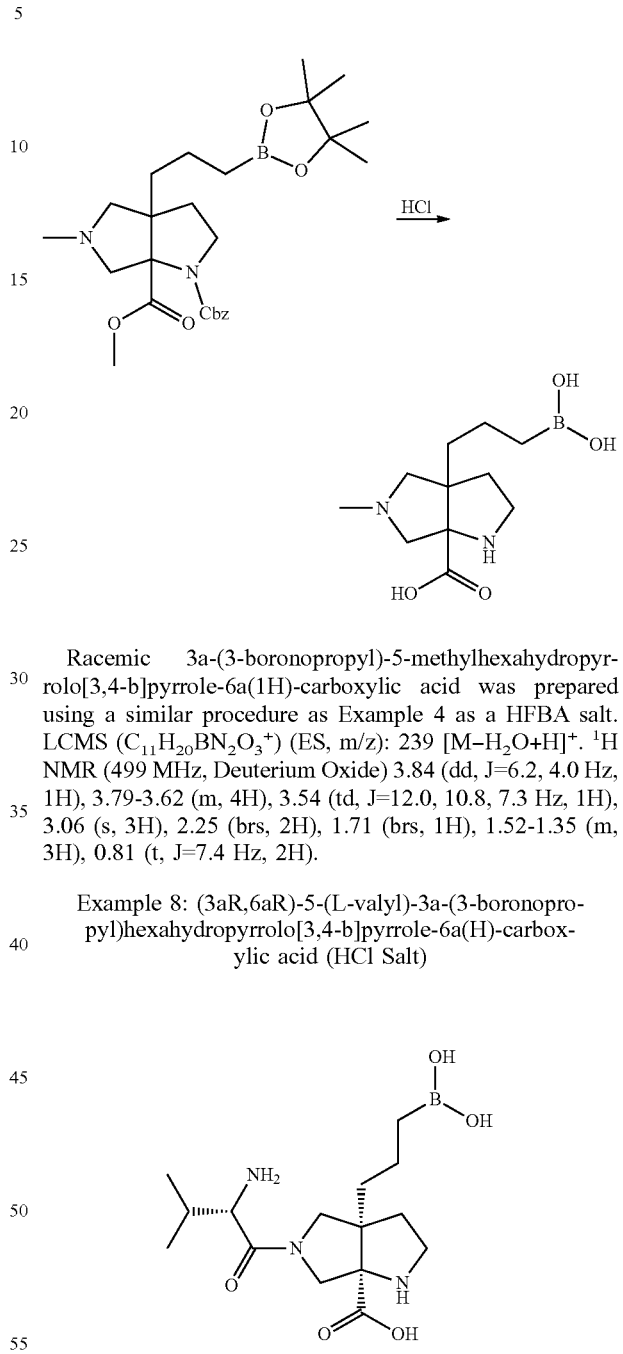

Racemic 3a-(3-boronopropyl)-5-methylhexahydropyrrolo[3,4-b]pyrrole-6a(1H)-carboxylic acid was prepared using a similar procedure as Example 4 as a HFBA salt. LCMS ($C_{11}H_{20}BN_2O_3^+$) (ES, m/z): 239 [M–H$_2$O+H]$^+$. $^1$H NMR (499 MHz, Deuterium Oxide) 3.84 (dd, J=6.2, 4.0 Hz, 1H), 3.79-3.62 (m, 4H), 3.54 (td, J=12.0, 10.8, 7.3 Hz, 1H), 3.06 (s, 3H), 2.25 (brs, 2H), 1.71 (brs, 1H), 1.52-1.35 (m, 3H), 0.81 (t, J=7.4 Hz, 2H).

Example 8: (3aR,6aR)-5-(L-valyl)-3a-(3-boronopropyl)hexahydropyrrolo[3,4-b]pyrrole-6a(H)-carboxylic acid (HCl Salt)

(3aR,6aR)-5-(L-valyl)-3a-(3-boronopropyl)hexahydropyrrolo[3,4-b]pyrrole-6a(H)-carboxylic acid (HCl salt) was prepared using a similar procedure as Example 2 as a HCl salt. The title compound was obtained as a 2:1 mixture of rotamers at room temperature. LCMS ($C_{15}H_{27}BN_3O_4^+$) (ES, m/z): 324 [M–H$_2$O+H]$^+$. $^1$H NMR (499 MHz, Deuterium Oxide) δ 4.40 (d, J=12.9 Hz, 0.33H), 4.32 (d, J=14.0 Hz, 0.66H), 4.19-4.12 (m, 1H), 3.88 (d, J=14.0 Hz, 0.66H), 3.85 (d, J=11.0 Hz, 0.33H), 3.83 (d, J=12.8 Hz, 0.66H), 3.74 (d, J=11.1 Hz, 0.66H), 3.67-3.57 (m, 1.66H), 3.58-3.46 (m, 1H), 2.37 (dq, J=13.3, 6.6 Hz, 1H), 2.29 (dq, J=14.3, 7.5, 6.4 Hz, 1H), 2.23 (m, 0.33H), 2.21-2.09 (m, 1H), 1.60-1.41 (m, 3H), 1.40-1.33 (m, 1H), 1.11 (d, J=6.9 Hz, 3H), 1.05 (d, J=6.9 Hz, 2H), 1.03 (d, J=6.9 Hz, 1H), 0.85-0.79 (m, 2H).

Example 9: (3aR,6aR)-5-(L-seryl)-3a-(3-boronopropyl)hexahydropyrrolo[3,4-b]pyrrole-6a(1H)-carboxylic acid

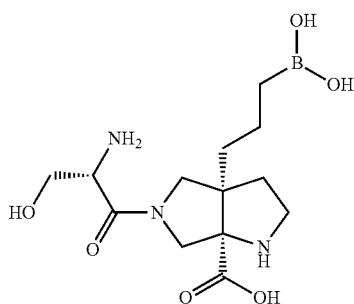

Step 1: methyl (3aR,6aR)-5-(O-benzyl-N-(tert-butoxycarbonyl)-L-seryl)-3a-(3-(4,4,5,5-tetramethyl-1,3,2-dioxaborolan-2-yl)propyl)hexahydropyrrolo[3,4-b]pyrrole-6a(1H)-carboxylate

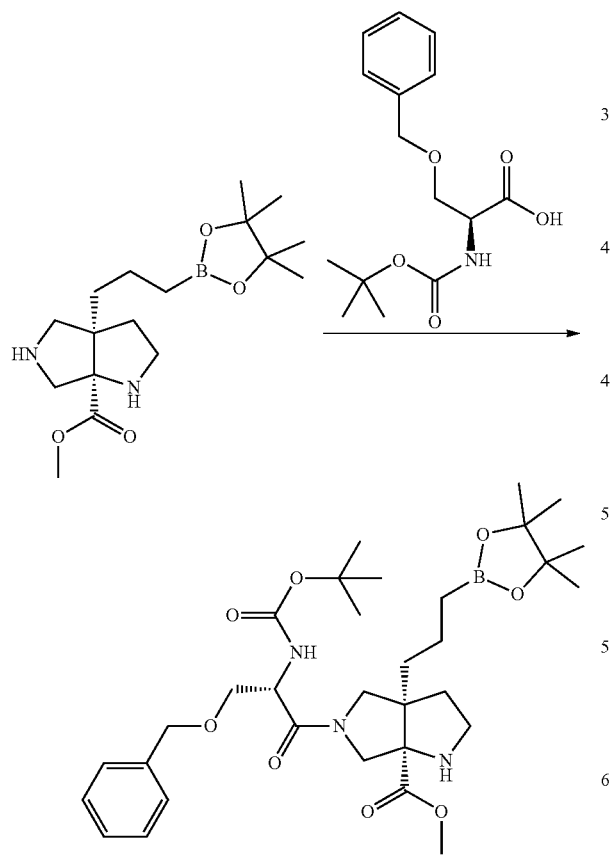

HATU (120 mg, 0.32 mmol), Boc-Ser(Bzl)-OH (78 mg, 0.27 mmol) and DIPEA (190 µL, 1.1 mmol) were added to a solution of methyl (3aR,6aR)-3a-(3-(4,4,5,5-tetramethyl-1,3,2-dioxaborolan-2-yl)propyl)hexahydropyrrolo[3,4-b]pyrrole-6a(1H)-carboxylate (I-2, TFA salt, 150 mg, 0.27 mmol) in DCM (1.4 mL). The reaction mixture was stirred at ambient temperature for 19 hours. The reaction mixture was concentrated under reduced pressure and the resulting residue was purified by silica gel chromatography (EtOAc in DCM) to afford methyl (3aR,6aR)-5-(O-benzyl-N-(tert-butoxycarbonyl)-L-seryl)-3a-(3-(4,4,5,5-tetramethyl-1,3,2-dioxaborolan-2-yl)propyl)hexahydropyrrolo[3,4-b]pyrrole-6a(1H)-carboxylate. LCMS ($C_{32}H_{51}BN_3O_8^+$) (ES, m/z): 616 [M+H]$^+$.

Step 2: methyl (3aR,6aR)-5-((tert-butoxycarbonyl)-L-seryl)-3a-(3-(4,4,5,5-tetramethyl-1,3,2-dioxaborolan-2-yl)propyl)hexahydropyrrolo[3,4-b]pyrrole-6a(1H)-carboxylate

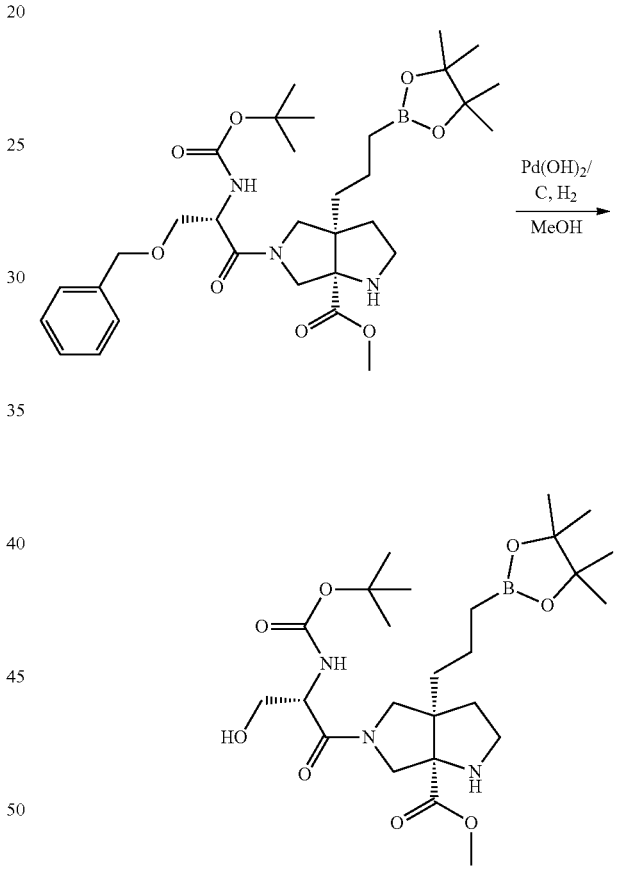

Pd(OH)$_2$/C (23 mg, 0.033 mmol) was added to a solution of methyl (3aR,6aR)-5-(O-benzyl-N-(tert-butoxycarbonyl)-L-seryl)-3a-(3-(4,4,5,5-tetramethyl-1,3,2-dioxaborolan-2-yl)propyl)hexahydropyrrolo[3,4-b]pyrrole-6a(1H)-carboxylate (100 mg, 0.17 mmol) in MeOH (2 mL). The reaction mixture was degassed and backfilled with H$_2$ three times then stirred under an atmosphere of H$_2$ for 45 hours. The mixture was filtered and concentrated under reduced pressure to afford crude methyl (3aR,6aR)-5-((tert-butoxycarbonyl)-L-seryl)-3a-(3-(4,4,5,5-tetramethyl-1,3,2-dioxaborolan-2-yl)propyl)hexahydropyrrolo[3,4-b]pyrrole-6a(1H)-carboxylate. LCMS ($C_{25}H_{45}BN_3O_8^+$) (ES, m/z): 526 [M+H]$^+$.

Step 3: (3aR,6aR)-3a-(3-boronopropyl)-5-((tert-butoxycarbonyl)-L-seryl)hexahydropyrrolo[3,4-b]pyrrole-6a(1H)-carboxylic acid

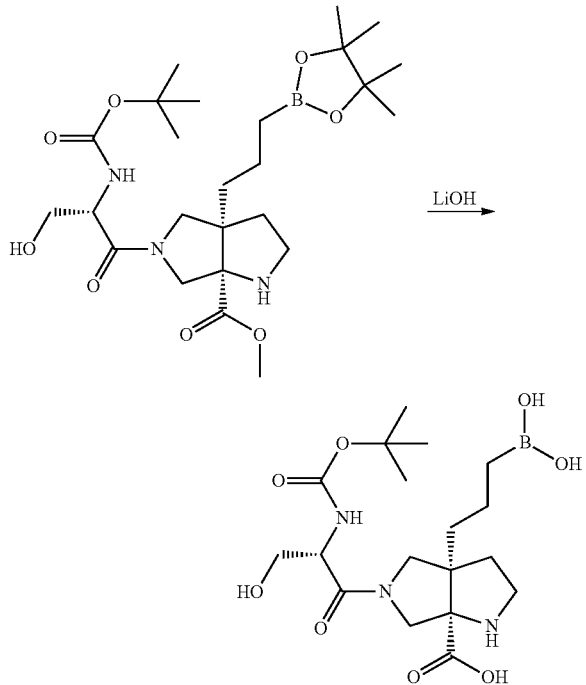

LiOH (2.5 mL, 2.5 mmol, 1.0 M in water) was added to a solution of methyl (3aR,6aR)-5-((tert-butoxycarbonyl)-L-seryl)-3a-(3-(4,4,5,5-tetramethyl-1,3,2-dioxaborolan-2-yl)propyl)hexahydropyrrolo[3,4-b]pyrrole-6a(1H)-carboxylate (88 mg, 0.17 mmol) in THF (2.2 mL) and MeOH (1.1 mL). The mixture was stirred at ambient temperature for 67 hours then concentrated under reduced pressure. The resulting residue was purified by prep-HPLC (MeCN/H$_2$O with 0.1% TFA) to afford (3aR,6aR)-3a-(3-boronopropyl)-5-((tert-butoxycarbonyl)-L-seryl)hexahydropyrrolo[3,4-b]pyrrole-6a(1H)-carboxylic acid as the TFA salt. LCMS (C$_{18}$H$_{31}$BN$_3$O$_7^+$) (ES, m/z): 412 [M−H$_2$O+H]$^+$.

Step 4: (3aR,6aR)-5-(L-seryl)-3a-(3-boronopropyl)hexahydropyrrolo[3,4-b]pyrrole-6a(H)-carboxylic acid

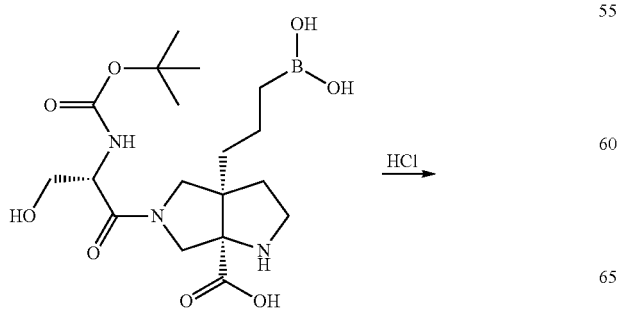

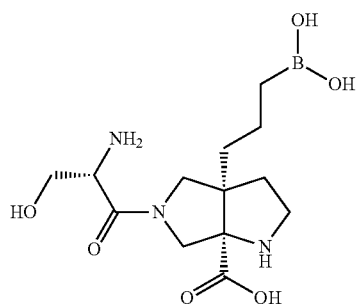

A mixture of (3aR,6aR)-3a-(3-boronopropyl)-5-((tert-butoxycarbonyl)-L-seryl)hexahydropyrrolo[3,4-b]pyrrole-6a(1H)-carboxylic acid (28 mg, 0.051 mmol) and 3 M HCl (1 mL, 3 mmol) was brought to 50° C. for 3 hours. The reaction mixture was cooled to room temperature and concentrated under reduced pressure. The resulting residue was purified by prep-HPLC (Column: Waters Atlantis T3 19×250 mm Sum, water (20 mM HFBA and 0.1% TFA)-CH$_3$CN). Fractions containing product were concentrated under reduced pressure, and the resulting residue was taken up in 1 M HCl (2 mL), frozen and lyophilized to dryness to afford (3aR, 6aR)-5-(L-seryl)-3a-(3-boronopropyl)hexahydropyrrolo[3,4-b]pyrrole-6a(1H)-carboxylic acid as HCl salt. The product exhibited a 2:1 distribution of amide rotamers by $^1$H NMR at room temperature. LCMS (C$_{13}$H$_{23}$BN$_3$O$_5^+$) (ES, m/z): 312 [M−H$_2$O+H]$^+$. $^1$H NMR (499 MHz, D$_2$O) δ 4.34 (t, J=5.1 Hz, 1H), 4.30 (d, J=12.8 Hz, 0.35H), 4.20 (d, J=14.1 Hz, 0.65H), 4.06 (d, J=12.9 Hz, 0.35H), 3.96-3.87 (m, 1.7H), 3.85-3.77 (m, 1.3H), 3.75 (d, J=12.7 Hz, 0.35H), 3.65 (d, J=11.2 Hz, 0.65H), 3.57-3.50 (m, 1.3H), 3.49-3.37 (m, 1.35H), 2.31-2.03 (m, 2H), 1.49-1.22 (m, 4H), 0.79-0.68 (m, 2H).

Example 10: (3aR,6aR)-5-(L-prolyl)-3a-(3-boronopropyl)hexahydropyrrolo[3,4-b]pyrrole-6a(1H)-carboxylic acid (HCl Salt)

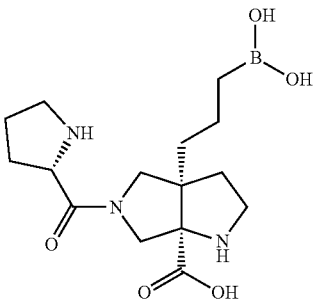 [SMILES: O=C([C@@H]1CCCN1)N1C[C@@]2(CCCB(O)O)CCN[C@@]2(C(=O)O)C1]

Step 1: methyl (3aR,6aR)-5-((tert-butoxycarbonyl)-L-prolyl)-3a-(3-(4,4,5,5-tetramethyl-1,3,2-dioxaborolan-2-yl)propyl)hexahydropyrrolo[3,4-b]pyrrole-6a(1H)-carboxylate

Step 2: (3aR,6aR)-3a-(3-boronopropyl)-5-((tert-butoxycarbonyl)-L-prolyl)hexahydropyrrolo[3,4-b]pyrrole-6a(1H)-carboxylic acid

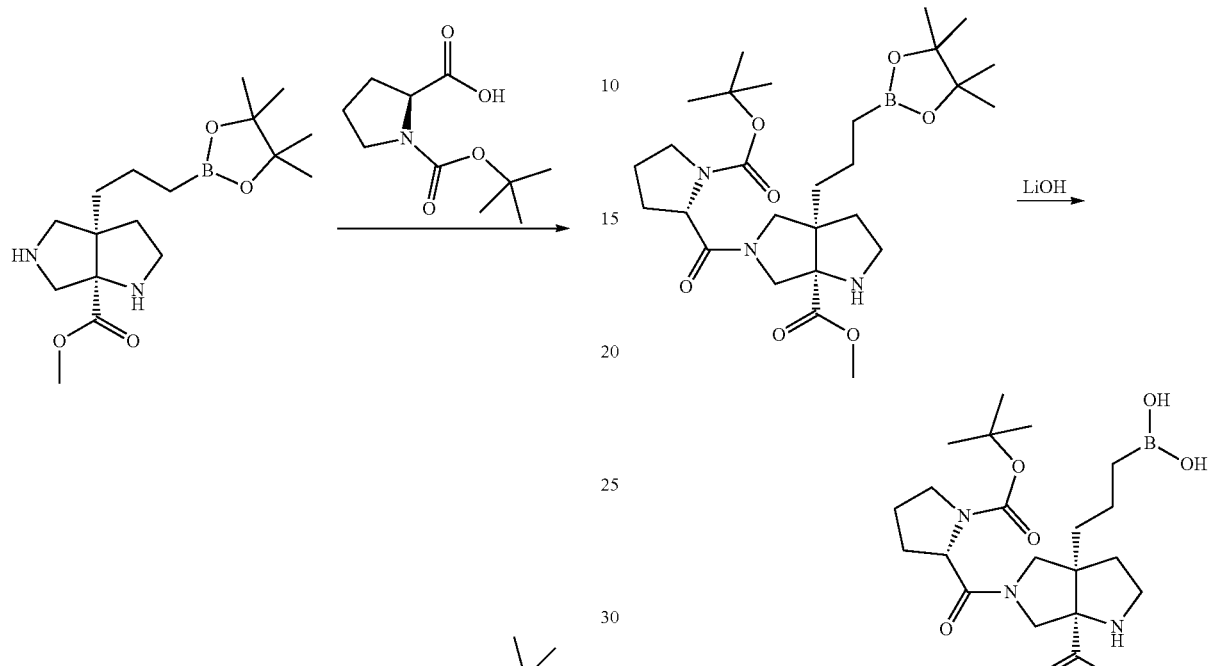

LiOH (2.2 mL, 2.5 mmol, 1.0 M in water) was added to a solution of methyl (3aR,6aR)-5-((tert-butoxycarbonyl)-L-prolyl)-3a-(3-(4,4,5,5-tetramethyl-1,3,2-dioxaborolan-2-yl)propyl)hexahydropyrrolo[3,4-b]pyrrole-6a(1H)-carboxylate (47 mg, 0.088 mmol) in THF (1.7 mL) and MeOH (0.85 mL). The mixture was stirred at ambient temperature for 66 hours then concentrated under reduced pressure. The resulting residue was purified by prep-HPLC (MeCN/H$_2$O with 0.1% TFA) to afford (3aR,6aR)-3a-(3-boronopropyl)-5-((tert-butoxycarbonyl)-L-prolyl)hexahydropyrrolo[3,4-b]pyrrole-6a(1H)-carboxylic acid as the TFA salt. LCMS (C$_{20}$H$_{33}$BN$_3$O$_6^+$) (ES, m/z): 422 [M–H$_2$O+H]$^+$.

Step 3: (3aR,6aR)-5-(L-prolyl)-3a-(3-boronopropyl)hexahydropyrrolo[3,4-b]pyrrole-6a(H)-carboxylic acid HATU (67 mg, 0.18 mmol), Boc-L-Proline (32 mg, 0.15 mmol) and DIPEA (100 µL, 0.59 mmol) were added to a solution of methyl (3aR,6aR)-3a-(3-(4,4,5,5-tetramethyl-1,3,2-dioxaborolan-2-yl)propyl)hexahydropyrrolo[3,4-b]pyrrole-6a(1H)-carboxylate (TFA salt, 50 mg, 0.088 mmol) in DCM (1 mL). The reaction mixture was stirred at ambient temperature for 18 hours then concentrated under reduced pressure, and the resulting residue was purified by silica gel chromatography (MeOH in DCM) to afford methyl (3aR,6aR)-5-((tert-butoxycarbonyl)-L-prolyl)-3a-(3-(4,4,5,5-tetramethyl-1,3,2-dioxaborolan-2-yl)propyl)hexahydropyrrolo[3,4-b]pyrrole-6a(1H)-carboxylate as a colorless oil. LCMS (C$_{27}$H$_{47}$BN$_3$O$_7^+$) (ES, m/z): 536 [M+H]$^+$.

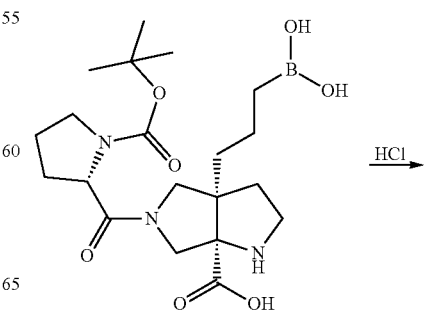

-continued

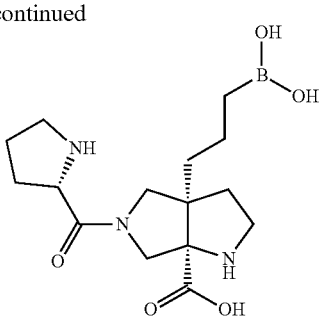

A mixture of (3aR,6aR)-3a-(3-boronopropyl)-5-((tert-butoxycarbonyl)-L-prolyl)hexahydropyrrolo[3,4-b]pyrrole-6a(1H)-carboxylic acid (TFA salt, 30 mg, 0.054 mmol) and 3 M HCl (1 mL, 3 mmol) was brought to 50° C. for 2 hours. The reaction mixture was cooled to room temperature and concentrated under reduced pressure. The resulting residue was purified by prep-HPLC (Column: Waters Atlantis T3 19×250 mm 5 um, water (20 mM HFBA and 0.1% TFA)-CH$_3$CN). Product fractions were concentrated under reduced pressure and the resulting residue was taken up in 1 M HCl (3 mL), frozen and lyophilized to dryness to afford (3aR,6aR)-5-(L-prolyl)-3a-(3-boronopropyl)hexahydropyrrolo[3,4-b]pyrrole-6a(1H)-carboxylic acid as the HCl salt. LCMS (C$_{15}$H$_{25}$BN$_3$O$_4^+$) (ES, m/z): 322 [M–H$_2$O+H]$^+$.

Step 4: (3aR,6aR)-5-(L-prolyl)-3a-(3-((3aR,4R,6R,7aS)-3a,5,5-trimethylhexahydro-4,6-methanobenzo[d][1,3,2]dioxaborol-2-yl)propyl)hexahydropyrrolo[3,4-b]pyrrole-6a(1H)-carboxylic acid

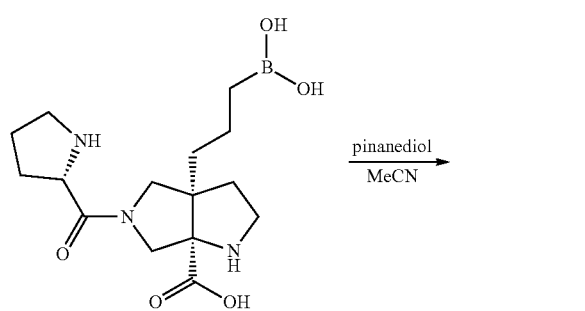

(1R,2R,3S,5R)-2,6,6-trimethylbicyclo[3.1.1]heptane-2,3-diol (5.8 mg, 0.034 mmol) was added to a solution of (3aR,6aR)-5-(L-prolyl)-3a-(3-boronopropyl)hexahydropyrrolo[3,4-b]pyrrole-6a(1H)-carboxylic acid (HCl salt, 7 mg, 0.017 mmol) in acetonitrile (1 mL). The resulting slurry was brought to 85° C. for 5 h. The reaction mixture was cooled to room temperature, diluted with MeOH (1 mL) and directly purified by prep-HPLC (ACN/H$_2$O with 0.1% TFA) to afford (3aR,6aR)-5-(L-prolyl)-3a-(3-((3aR,4R,6R,7aS)-3a,5,5-trimethylhexahydro-4,6-methanobenzo[d][1,3,2]dioxaborol-2-yl)propyl)hexahydropyrrolo[3,4-b]pyrrole-6a(1H)-carboxylic acid as the TFA salt. LCMS (C$_{25}$H$_{41}$BN$_3$O$_5^+$) (ES, m/z): 474 [M+H]$^+$.

Step 5: (3aR,6aR)-5-(L-prolyl)-3a-(3-boronopropyl)hexahydropyrrolo[3,4-b]pyrrole-6a(1H)-carboxylic acid

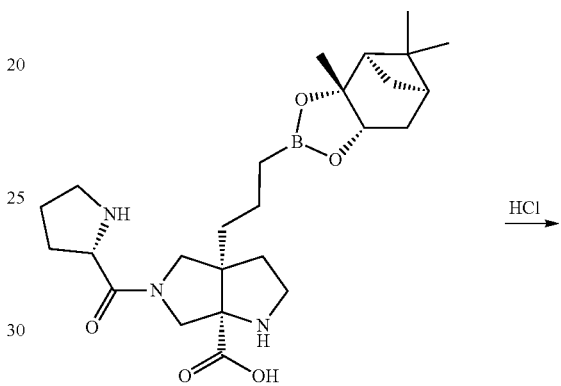

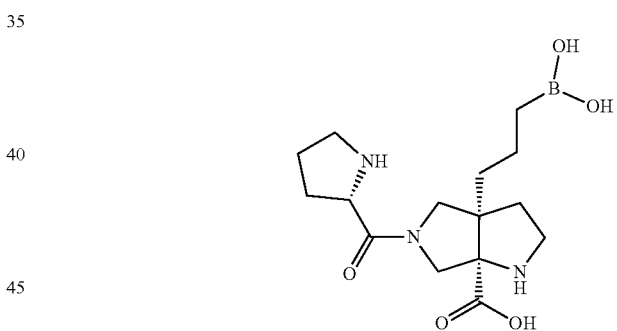

A mixture of (3aR,6aR)-5-(L-prolyl)-3a-(3-((3aR,4R,6R,7aS)-3a,5,5-trimethylhexahydro-4,6-methanobenzo[d][1,3,2]dioxaborol-2-yl)propyl)hexahydropyrrolo[3,4-b]pyrrole-6a(1H)-carboxylic acid (TFA salt, 11 mg, 0.016 mmol) and 2 M HCl (0.4 mL, 0.8 mmol) was brought to 60° C. for 19 hours. The reaction mixture was cooled to room temperature and washed with DCM. The resulting aqueous layer was concentrated to give (3aR,6aR)-5-(L-prolyl)-3a-(3-boronopropyl)hexahydropyrrolo[3,4-b]pyrrole-6a(1H)-carboxylic acid as the HCl salt. The title compound was obtained as a 2:1 mixture of rotamers at room temperature. LCMS (C$_{15}$H$_{25}$BN$_3$O$_4^+$) (ES, m/z): 322 [M–H$_2$O+H]$^+$. $^1$H NMR (499 MHz, Deuterium Oxide) δ 4.55-4.45 (m, 0.75H), 4.34-4.27 (m, 0.25H), 4.26-4.21 (m, 0.25H), 4.21-4.17 (m, 0.5H), 4.13-4.06 (m, 0.25H), 4.05-4.00 (m, 0.25H), 3.88-3.77 (m, 0.5H), 3.73-3.60 (m, 1.5H), 3.59-3.25 (m, 4.75H), 2.55-2.22 (m, 2H), 2.21-1.88 (m, 4H), 1.58-1.21 (m, 4H), 0.76-0.66 (m, 2H).

Example 11: (1S,5R)-1-(3-boronopropyl)-3,6-diazabicyclo[3.2.0]heptane-5-carboxylic acid

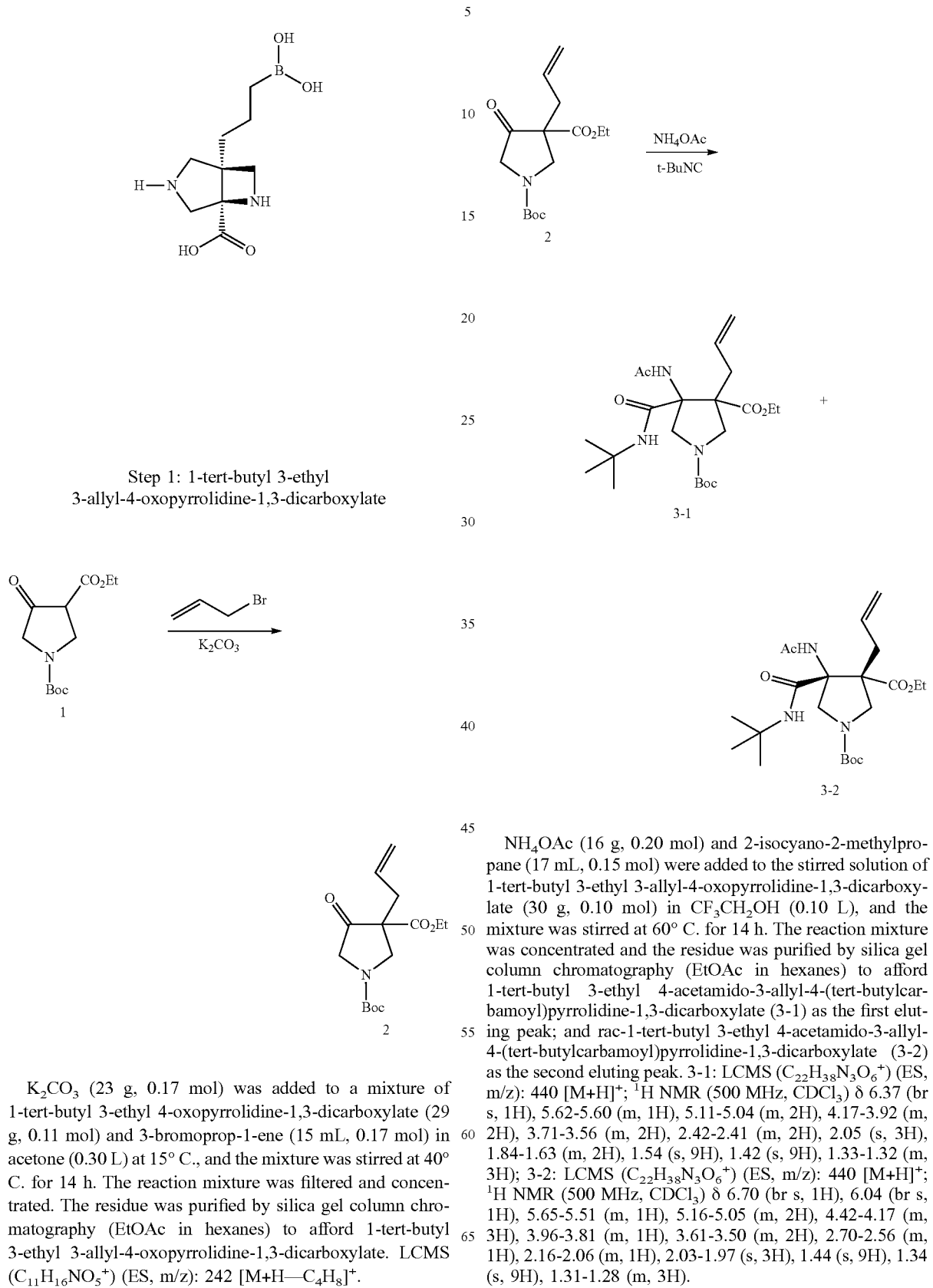

Step 1: 1-tert-butyl 3-ethyl 3-allyl-4-oxopyrrolidine-1,3-dicarboxylate

K$_2$CO$_3$ (23 g, 0.17 mol) was added to a mixture of 1-tert-butyl 3-ethyl 4-oxopyrrolidine-1,3-dicarboxylate (29 g, 0.11 mol) and 3-bromoprop-1-ene (15 mL, 0.17 mol) in acetone (0.30 L) at 15° C., and the mixture was stirred at 40° C. for 14 h. The reaction mixture was filtered and concentrated. The residue was purified by silica gel column chromatography (EtOAc in hexanes) to afford 1-tert-butyl 3-ethyl 3-allyl-4-oxopyrrolidine-1,3-dicarboxylate. LCMS (C$_{11}$H$_{16}$NO$_5^+$) (ES, m/z): 242 [M+H—C$_4$H$_8$]$^+$.

Step 2: rac-1-(tert-butyl) 3-ethyl 4-acetamido-3-allyl-4-(tert-butylcarbamoyl)pyrrolidine-1,3-dicarboxylate NH$_4$OAc (16 g, 0.20 mol) and 2-isocyano-2-methylpropane (17 mL, 0.15 mol) were added to the stirred solution of 1-tert-butyl 3-ethyl 3-allyl-4-oxopyrrolidine-1,3-dicarboxylate (30 g, 0.10 mol) in CF$_3$CH$_2$OH (0.10 L), and the mixture was stirred at 60° C. for 14 h. The reaction mixture was concentrated and the residue was purified by silica gel column chromatography (EtOAc in hexanes) to afford 1-tert-butyl 3-ethyl 4-acetamido-3-allyl-4-(tert-butylcarbamoyl)pyrrolidine-1,3-dicarboxylate (3-1) as the first eluting peak; and rac-1-tert-butyl 3-ethyl 4-acetamido-3-allyl-4-(tert-butylcarbamoyl)pyrrolidine-1,3-dicarboxylate (3-2) as the second eluting peak. 3-1: LCMS (C$_{22}$H$_{38}$N$_3$O$_6^+$) (ES, m/z): 440 [M+H]$^+$; $^1$H NMR (500 MHz, CDCl$_3$) δ 6.37 (br s, 1H), 5.62-5.60 (m, 1H), 5.11-5.04 (m, 2H), 4.17-3.92 (m, 2H), 3.71-3.56 (m, 2H), 2.42-2.41 (m, 2H), 2.05 (s, 3H), 1.84-1.63 (m, 2H), 1.54 (s, 9H), 1.42 (s, 9H), 1.33-1.32 (m, 3H); 3-2: LCMS (C$_{22}$H$_{38}$N$_3$O$_6^+$) (ES, m/z): 440 [M+H]$^+$; $^1$H NMR (500 MHz, CDCl$_3$) δ 6.70 (br s, 1H), 6.04 (br s, 1H), 5.65-5.51 (m, 1H), 5.16-5.05 (m, 2H), 4.42-4.17 (m, 3H), 3.96-3.81 (m, 1H), 3.61-3.50 (m, 2H), 2.70-2.56 (m, 1H), 2.16-2.06 (m, 1H), 2.03-1.97 (s, 3H), 1.44 (s, 9H), 1.34 (s, 9H), 1.31-1.28 (m, 3H).

Step 3: rac-4-acetamido-3-allyl-1-(tert-butoxycarbonyl)-4-(tert-butylcarbamoyl)pyrrolidine-3-carboxylic acid

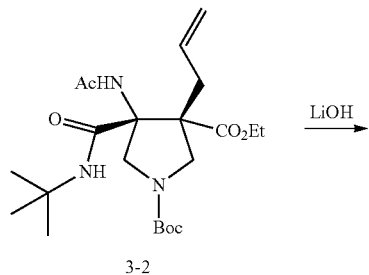

3-2

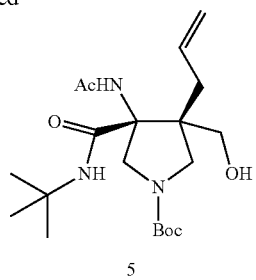

5

TEA (0.51 mL, 3.7 mmol) was added to the stirred mixture of isobutyl chloroformate (0.47 mL, 3.7 mmol) and 4-acetamido-3-allyl-1-(tert-butoxycarbonyl)-4-(tert-butylcarbamoyl)pyrrolidine-3-carboxylic acid (1.0 g, 2.4 mmol) in THF (10 mL) at 0° C., and the mixture was stirred at 20° C. for 1 h. The reaction mixture was diluted with diethyl ether, filtered and concentrated. The residue was dissolved in MeOH (5.0 mL), followed by addition of NaBH$_4$ (0.18 g, 4.9 mmol), and the resulting mixture was stirred at 20° C. for 1 h. The reaction mixture was quenched with saturated aqueous NH$_4$Cl and extracted with EtOAc. The combined organic phase was concentrated, and the residue was purified by RP-HPLC [C18 column, water (0.1% TFA)-CH$_3$CN] to give rac-tert-butyl 3-acetamido-4-allyl-3-(tert-butylcarbamoyl)-4-(hydroxymethyl)pyrrolidine-1-carboxylate. LCMS (C$_{20}$H$_{36}$N$_3$O$_5{}^+$) (ES, m/z): 398 [M+H]$^+$.

Step 5: tert-butyl 3-acetamido-4-allyl-3-(tert-butylcarbamoyl)-4-(hydroxymethyl)pyrrolidine-1-carboxylate

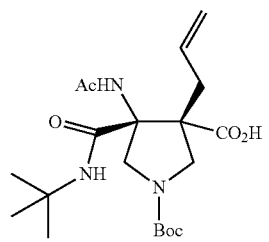

4

LiOH (1 M in water, 4.6 mL, 4.6 mmol) was added to the stirred solution of 1-tert-butyl 3-ethyl 4-acetamido-3-allyl-4-(tert-butylcarbamoyl)pyrrolidine-1,3-dicarboxylate (3-2, 1.0 g, 2.3 mmol) in THF (2.3 mL) at 20° C., and the mixture was stirred at 20° C. for 12 h. The reaction mixture was acidified with 1 N HCl in water to pH~ 6, and extracted with EtOAc. The combined organic phase was concentrated to give crude rac-4-acetamido-3-allyl-1-(tert-butoxycarbonyl)-4-(tert-butylcarbamoyl)pyrrolidine-3-carboxylic acid, which was used in the next step directly without further purification. LCMS (C$_{20}$H$_{34}$N$_3$O$_6{}^+$) (ES, m/z): 412 [M+H]$^+$.

Step 4: rac-tert-butyl 3-acetamido-4-allyl-3-(tert-butylcarbamoyl)-4-(hydroxymethyl)pyrrolidine-1-carboxylate

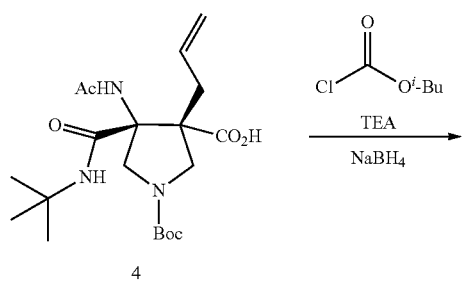

4

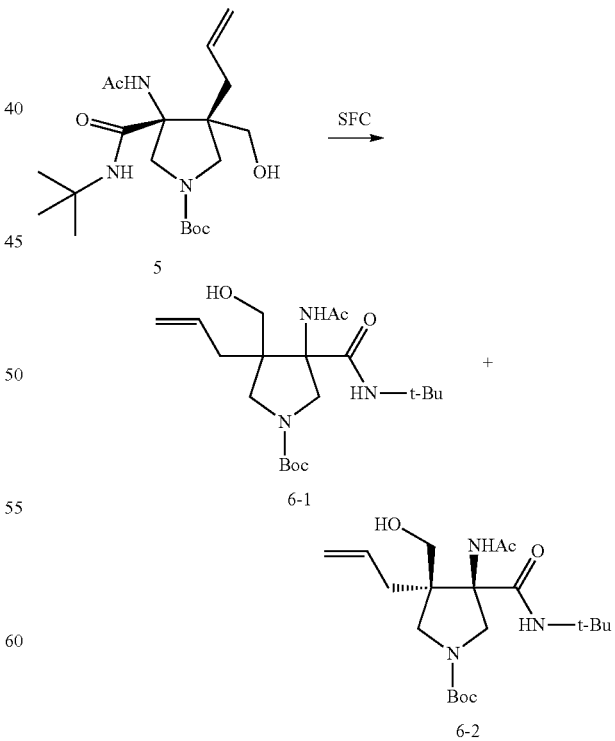

The tert-butyl 3-acetamido-4-allyl-3-(tert-butylcarbamoyl)-4-(hydroxymethyl)pyrrolidine-1-carboxylate (0.40 g, 1.0 mmol) was resolved by Chiral-SFC [Column: DAICEL CHIRALPAK AD-H (250 mm*50 mm, 10 um), Mobile phase: A: $CO_2$, B: EtOH (0.1% $NH_3 \cdot H_2O$), Gradient: 30% of B in 3.5 min, and hold 30% of B for 1 min, Flow Rate (mL/min) 180, Column Temperature: 40° C.] to give tert-butyl 3-acetamido-4-allyl-3-(tert-butylcarbamoyl)-4-(hydroxymethyl)pyrrolidine-1-carboxylate (6-1: $t_r$=2.13 min) as the first eluting peak, and tert-butyl 3-acetamido-4-allyl-3-(tert-butylcarbamoyl)-4-(hydroxymethyl)pyrrolidine-1-carboxylate (6-2: $t_r$=2.29 min) as the second eluting peak. 6-1: LCMS ($C_{20}H_{36}N_3O_5^+$) (ES, m/z): 398 [M+H]$^+$; $^1$H NMR (500 MHz, $CDCl_3$) δ 6.07-5.89 (m, 1H), 5.83-5.58 (m, 1H), 5.23-5.08 (m, 2H), 4.38-4.21 (m, 1H), 3.84-3.76 (m, 2H), 3.72-3.71 (m, 2H), 3.58 (br d, J=11.9 Hz, 1H), 3.47-3.34 (m, 2H), 2.43-2.23 (m, 1H), 2.16-2.05 (m, 1H), 2.01 (s, 3H), 1.50-1.40 (s, 9H), 1.34 (s, 9H); 6-2: LCMS ($C_{20}H_{36}N_3O_5^+$) (ES, m/z): 398 [M+H]+; $^1$H NMR (500 MHz, $CDCl_3$) δ 6.11-5.91 (m, 1H), 5.81-5.57 (m, 1H), 5.23-5.02 (m, 2H), 4.42-4.21 (m, 1H), 3.86-3.72 (m, 3H), 3.65-3.53 (m, 1H), 3.46-3.33 (m, 2H), 2.43-2.21 (m, 1H), 2.14-2.10 (m, 2H), 2.00 (s, 3H), 1.43 (s, 9H), 1.34 (s, 9H).

Step 6: tert-butyl (3R,4R)-3-acetamido-4-allyl-3-(tert-butylcarbamoyl)-4-((tosyloxy)methyl)pyrrolidine-1-carboxylate

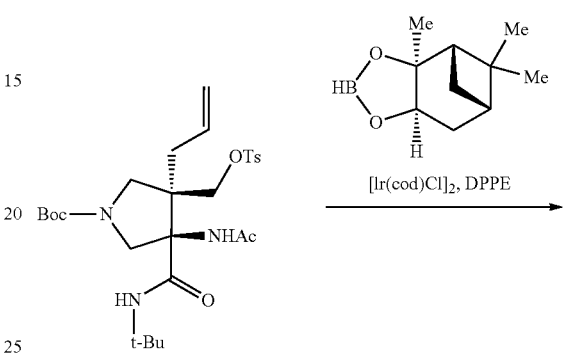

p-Toluenesulfonyl chloride (147 mg, 774 μmol) was added to a solution of tert-butyl (3R,4R)-3-acetamido-4-allyl-3-(tert-butylcarbamoyl)-4-(hydroxymethyl)pyrrolidine-1-carboxylate (205 mg, 516 μmol), triethylamine (216 μL, 157 mg, 1.6 mmol), and 4-dimethylaminopyridine (6.3 mg, 52 μmol) in DCM (2.58 mL) at 23° C. The reaction mixture was stirred for 20 h before it was loaded directly onto silica gel for purification by silica gel column chromatography (EtOAc/hexanes) to provide tert-butyl (3R,4R)-3-acetamido-4-allyl-3-(tert-butylcarbamoyl)-4-((tosyloxy)methyl)pyrrolidine-1-carboxylate. LCMS ($C_{22}H_{34}N_3O_5S^+$) (ES, m/z): 452 [M+H—$C_5O_2H_8$]$^+$.

Step 7: tert-butyl (3R,4R)-3-acetamido-3-(tert-butylcarbamoyl)-4-((tosyloxy)methyl)-4-(3-((3aS,4S,6S,7aR)-3a,5,5-trimethylhexahydro-4,6-methanobenzo[d][1,3,2]dioxaborol-2-yl)propyl)pyrrolidine-1-carboxylate

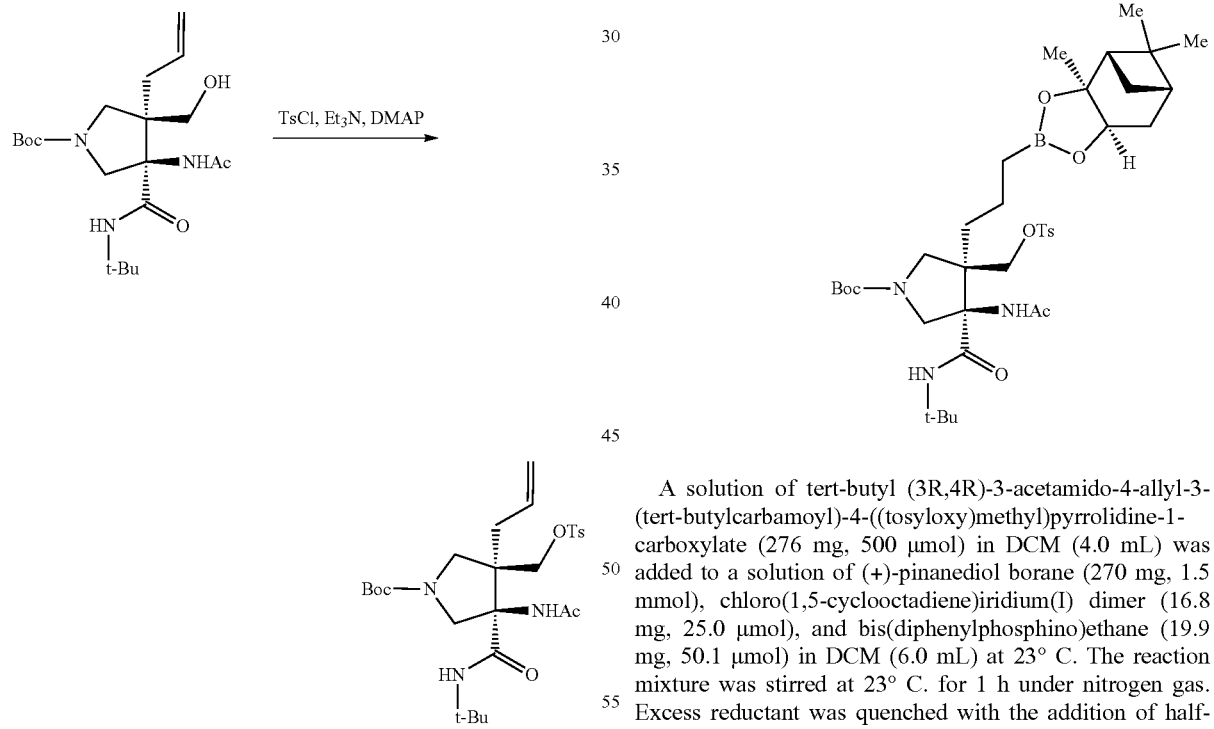

A solution of tert-butyl (3R,4R)-3-acetamido-4-allyl-3-(tert-butylcarbamoyl)-4-((tosyloxy)methyl)pyrrolidine-1-carboxylate (276 mg, 500 μmol) in DCM (4.0 mL) was added to a solution of (+)-pinanediol borane (270 mg, 1.5 mmol), chloro(1,5-cyclooctadiene)iridium(I) dimer (16.8 mg, 25.0 μmol), and bis(diphenylphosphino)ethane (19.9 mg, 50.1 μmol) in DCM (6.0 mL) at 23° C. The reaction mixture was stirred at 23° C. for 1 h under nitrogen gas. Excess reductant was quenched with the addition of half-saturated aq. NaCl solution, and the resulting biphasic mixture was stirred until bubbling ceased. The layers were then separated, and the aqueous phase was extracted with DCM. The combined organic extracts were dried over $Na_2SO_4$, filtered, and concentrated. The residue was purified by silica gel column chromatography (EtOAc/hexanes) to provide tert-butyl (3R,4R)-3-acetamido-3-(tert-butylcarbamoyl)-4-((tosyloxy)methyl)-4-(3-((3aS,4S,6S,7aR)-3a,5,5-trimethylhexahydro-4,6-methanobenzo[d][1,3,2]dioxaborol-2-yl)propyl)pyrrolidine-1-carboxylate. LCMS ($C_{32}H_{51}BN_3O_7S$)$^+$ (ES, m/z): 632 [M+H—$C_5O_2H_8$]$^+$.

Step 8: (1S,5R)-1-(3-boronopropyl)-3,6-diazabicyclo[3.2.0]heptane-5-carboxylic acid

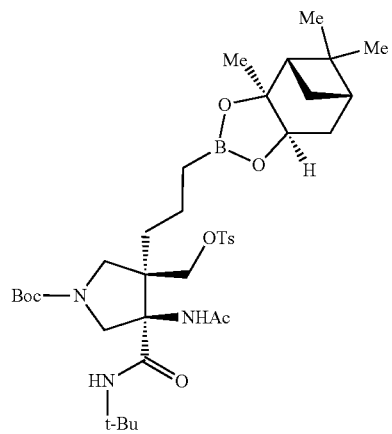

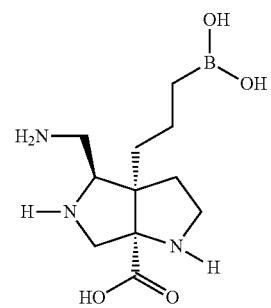

tert-butyl (3R,4R)-3-acetamido-3-(tert-butylcarbamoyl)-4-((tosyloxy)methyl)-4-(3-((3aS,4S,6S,7aR)-3a,5,5-trimethylhexahydro-4,6-methanobenzo[d][1,3,2]dioxaborol-2-yl)propyl)pyrrolidine-1-carboxylate (329 mg, 449 µmol) and 48% w/w aq. HBr solution (9.0 mL) were combined, and the resulting mixture was heated to 130° C. for 1 h. The mixture was then cooled to 23° C. before it was diluted with water (10 mL). The diluted aqueous solution was washed with DCM until both the aqueous layer and the organic washes were colorless, and then the aqueous layer was diluted with MeCN (10 mL). The diluted solution was concentrated under reduced pressure. This dried residue was then re-dissolved in water (9.0 mL). A portion of this solution (6.7 mL, 337 µmol theoretical) was treated with aq. NaHCO$_3$ solution (1.1 M, 920 µL, 1.0 mmol) at 23° C., in order to achieve pH=8. After 45 min, the reaction mixture was acidified with the addition of trifluoroacetic acid (91 µL, 130 mg, 1.2 mmol) at 23° C. to pH=2. The mixture was then concentrated under reduced pressure, and the residue was purified by RP-HPLC (Column: Waters Atlantis T3 19×250 mm, 5 µm, water [20 mM HFBA and 0.1% TFA]-CH$_3$CN). Fractions containing product were concentrated under reduced pressure to provide (1S,5R)-1-(3-boronopropyl)-3,6-diazabicyclo[3.2.0]heptane-5-carboxylic acid as an HFBA salt. LCMS (C$_9$H$_{16}$BN$_2$O$_3^+$) (ES, m/z): 211 [M–H$_2$O+H]$^+$.
$^1$H NMR (499 MHz, Deuterium Oxide) δ: 4.21 (d, J=14.6 Hz, 1H), 4.09 (d, J=12.2 Hz, 1H), 4.04 (d, J=12.0 Hz, 1H), 4.02 (d, J=14.6 Hz, 1H), 3.91 (d, J=12.9 Hz, 1H), 3.35 (d, J=12.9 Hz, 1H), 1.84 (app td, J=12.9, 4.8 Hz, 1H), 1.71 (app td, J=12.1, 5.0 Hz, 1H), 1.42-1.25 (m, 2H), 0.80 (t, J=7.7 Hz, 2H).

Example 12: (3aR,4R,6aR)-4-(aminomethyl)-3a-(3-boronopropyl)hexahydropyrrolo[3,4-b]pyrrole-6a(1H)-carboxylic acid as an HCl Salt

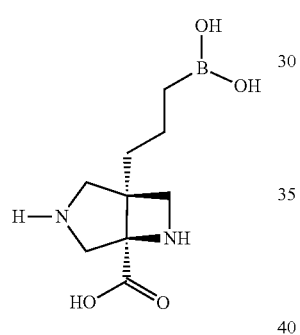

Step 1: methyl (3aR,6aR)-5-(2,6-dichlorobenzyl)-4-(nitromethyl)-3a-(3-(4,4,5,5-tetramethyl-1,3,2-dioxaborolan-2-yl)propyl)hexahydropyrrolo[3,4-b]pyrrole-6a(1H)-carboxylate

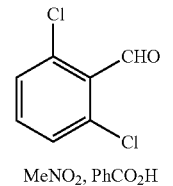

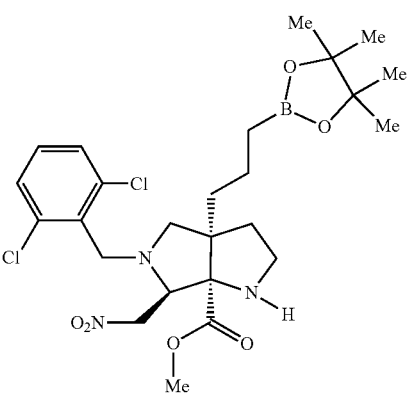

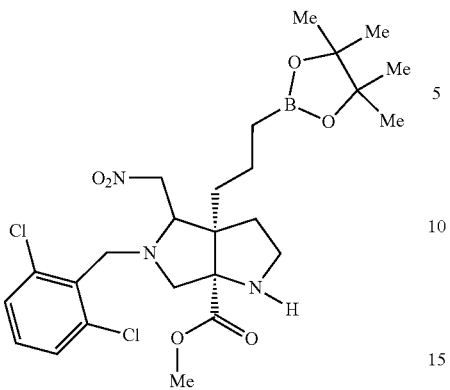

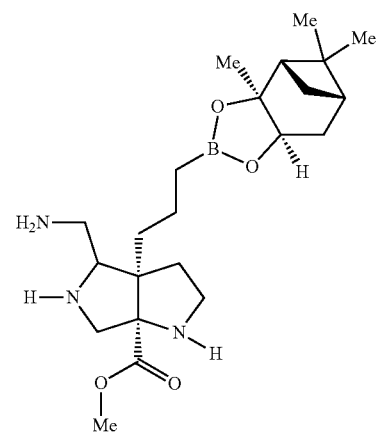

A solution of 2,6-dichlorobenzaldehyde (279 mg, 1.60 mmol) in toluene (2.0 mL) was added dropwise over 5 h via a syringe pump to a stirred, refluxing solution of methyl (3aR,6aR)-3a-(3-(4,4,5,5-tetramethyl-1,3,2-dioxaborolan-2-yl)propyl)hexahydropyrrolo[3,4-b]pyrrole-6a(1H)-carboxylate (I-2, TFA salt, 600 mg, 1.77 mmol), nitromethane (191 μL, 217 mg, 3.55 mmol), and benzoic acid (65.0 mg, 0.532 mmol) in toluene (8.9 mL). After reagent addition was complete, the reaction mixture was allowed to cool to 23° C. before it was diluted with DCM (20 mL). The diluted organic solution was shaken with sat. aq. NaHCO₃ solution, and the layers were then separated. The aqueous layer was extracted with DCM. The combined organic extracts were dried over Na₂SO₄, filtered, and concentrated under reduced pressure. The residue was purified by silica gel column chromatography (EtOAc/hexanes) to provide methyl (3aR, 6R,6aR)-5-(2,6-dichlorobenzyl)-6-(nitromethyl)-3a-(3-(4,4,5,5-tetramethyl-1,3,2-dioxaborolan-2-yl)propyl)hexahydropyrrolo[3,4-b]pyrrole-6a(1H)-carboxylate as the first-eluting isomer, and methyl (3aR,6aR)-5-(2,6-dichlorobenzyl)-4-(nitromethyl)-3a-(3-(4,4,5,5-tetramethyl-1,3,2-dioxaborolan-2-yl)propyl)hexahydropyrrolo[3,4-b]pyrrole-6a(1H)-carboxylate as the second-eluting isomer. LCMS ($C_{25}H_{37}BCl_2N_3O_6^+$) (ES, m/z): 557 [M+H]⁺.

Step 2: methyl (3aR,6aR)-4-(aminomethyl)-3a-(3-((3aS,4S,6S, aR)-3a,5,5-trimethylhexahydro-4,6-methanobenzo[d][1,3,2]dioxaborol-2-yl)propyl)hexahydropyrrolo[3,4-b]pyrrole-6a(1H)-carboxylate

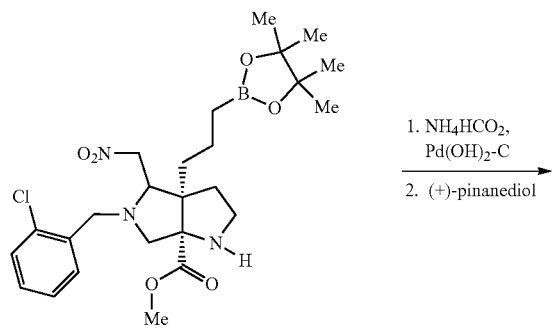

Palladium hydroxide on carbon (20% w/w, 241 mg, 0.343 mmol) was added to a solution of methyl (3aR,6aR)-5-(2,6-dichlorobenzyl)-4-(nitromethyl)-3a-(3-(4,4,5,5-tetramethyl-1,3,2-dioxaborolan-2-yl)propyl)hexahydropyrrolo[3,4-b]pyrrole-6a(1H)-carboxylate (191 mg, 0.343 mmol) and ammonium formate (217 mg, 3.43 mmol) in methanol (6.87 mL). The mixture was heated to 60° C. for 1 h. The mixture was then cooled to 23° C. and was filtered through a pad of CELITE in order to remove the heterogeneous catalyst. The filter cake was rinsed with methanol, and the filtrate was concentrated under reduced pressure. The residue was re-suspended in acetonitrile (1.72 mL) before (+)-pinanediol (117 mg, 0.686 mmol) was added. The resulting mixture was heated to 85° C. with stirring for 40 min before it was concentrated to dryness under reduced pressure. The residue was purified by RP-HPLC (C18 column, water [0.1% TFA]-CH₃CN) to give methyl (3aR,6aR)-4-(aminomethyl)-3a-(3-((3aS,4S,6S,7aR)-3a,5,5-trimethylhexahydro-4,6-methanobenzo[d][1,3,2]dioxaborol-2-yl)propyl)hexahydropyrrolo[3,4-b]pyrrole-6a(1H)-carboxylate as a TFA salt. LCMS ($C_{22}H_{39}BN_3O_4^+$) (ES, m/z): 420 (M+H)⁺.

Step 3: (3aR,4R,6aR)-4-(aminomethyl)-3a-(3-((3aS, 4S,6S, aR)-3a,5,5-trimethylhexahydro-4,6-methanobenzo[d][1,3,2]dioxaborol-2-yl)propyl)hexahydropyrrolo[3,4-b]pyrrole-6a(H)-carboxylic acid

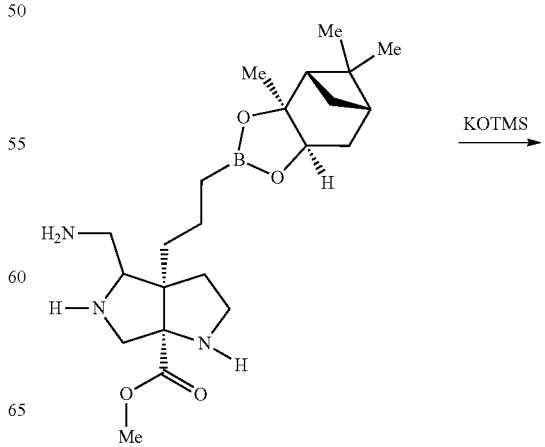

-continued

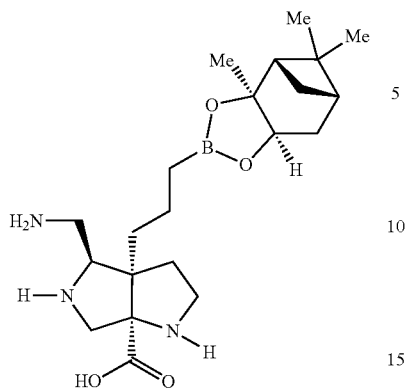

Potassium trimethylsilanolate (151 mg, 1.17 mmol) was added to a solution of methyl (3aR,6aR)-4-(aminomethyl)-3a-(3-((3aS,4S,6S,7aR)-3a,5,5-trimethylhexahydro-4,6-methanobenzo[d][1,3,2]dioxaborol-2-yl)propyl)hexahydropyrrolo[3,4-b]pyrrole-6a(1H)-carboxylate (TFA salt, 95.0 mg, 0.147 mmol) in THF (978 μL) at 23° C. The mixture was heated to 35° C. for 2.5 h before it was cooled to 23° C. A solution of trifluoroacetic acid (90.0 μL, 134 mg, 1.17 mmol) in toluene (9.0 mL) was added, and the resulting mixture was concentrated under reduced pressure. The residue was purified by RP-HPLC (C18 column, water [0.1% TFA]-CH$_3$CN) to give (3aR,4R,6aR)-4-(aminomethyl)-3a-(3-((3aS,4S,6S,7aR)-3a,5,5-trimethylhexahydro-4,6-methanobenzo[d][1,3,2]dioxaborol-2-yl)propyl)hexahydropyrrolo[3,4-b]pyrrole-6a(1H)-carboxylic acid as a TFA salt. LCMS (C$_{21}$H$_{37}$BN$_3$O$_4{}^+$) (ES, m/z): 406 (M+H)$^+$.

Step 4: (3aR,4R,6aR)-4-(aminomethyl)-3a-(3-boronopropyl)hexahydropyrrolo[3,4-b]pyrrole-6a(1H)-carboxylic acid

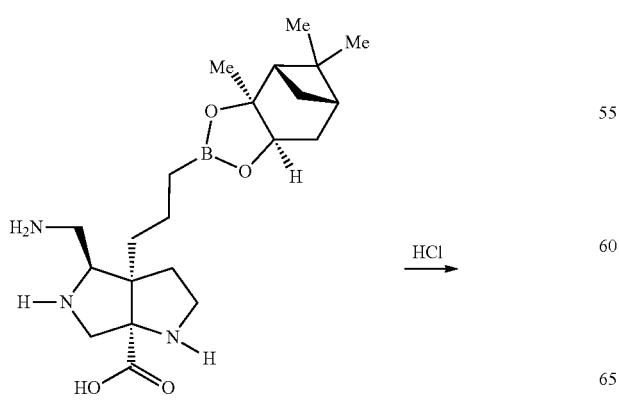

(3aR,4R,6aR)-4-(aminomethyl)-3a-(3-((3aS,4S,6S,7aR)-3a,5,5-trimethylhexahydro-4,6-methanobenzo[d][1,3,2]dioxaborol-2-yl)propyl)hexahydropyrrolo[3,4-b]pyrrole-6a (1H)-carboxylic acid (TFA salt, 22 mg, 35 μmol) and 6N aq. HCl solution (700 μL) were combined, and the resulting mixture was heated to 60° C. for 1.5 h. The mixture was then cooled to 23° C. before it was diluted with water (10 mL). The diluted solution was washed repeatedly with DCM, and the washed aqueous layer was then diluted with acetonitrile (10 mL). This diluted solution was concentrated under reduced pressure to provide (3aR,4R,6aR)-4-(aminomethyl)-3a-(3-boronopropyl)hexahydropyrrolo[3,4-b]pyrrole-6a(1H)-carboxylic acid as an HCl salt. LCMS (C$_{11}$H$_{21}$BN$_3$O$_3{}^+$) (ES, m/z): 254 (M–H$_2$O+H)$^+$. $^1$H NMR (499 MHz, Deuterium Oxide) δ: 4.13 (d, J=13.8 Hz, 1H), 4.09 (d, J=10.1 Hz, 1H), 3.80 (d, J=13.7 Hz, 1H), 3.68-3.60 (m, 3H), 3.49 (dd, J=14.5, 10.6 Hz, 1H), 2.35-2.31 (m, 1H), 2.25-2.19 (m, 1H), 1.73 (app td, J=12.9, 6.0 Hz, 1H), 1.61 (app td, J=12.8 Hz, 3.8 Hz, 1H), 1.52-1.44 (m, 2H), 0.80 (t, J=7.4 Hz, 2H).

The following examples were prepared using a general procedure outlined above for Example 10.

| Example | Structure | [M − H₂O + H]+. | NMR |
|---|---|---|---|
| 13 | 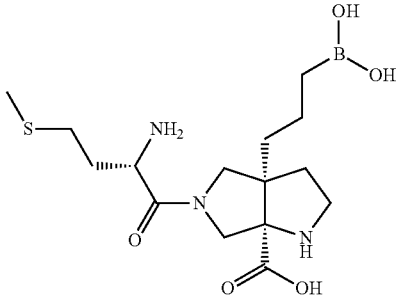 [SMILES: CSCC[C@H](N)C(=O)N1C[C@@]2(CCCB(O)O)CCN[C@@]2(C(=O)O)C1] | 356 | 1H NMR (499 MHz, Deuterium Oxide) δ 4.41-4.31 (m, 2H), 4.24 (d, J = 14.1 Hz, 1H), 3.88-3.74 (m, 2H), 3.70 (t, J = 12.2 Hz, 1H), 3.55 (dq, J = 13.4, 7.1, 6.3 Hz, 2H), 3.46 (ddd, J = 15.0, 10.4, 7.0 Hz, 1H), 2.66-2.55 (m, 2H), 2.31 (ddd, J = 13.7, 7.8, 5.8 Hz, 1H), 2.14 (ddt, J = 16.5, 9.7, 5.3 Hz, 3H), 2.05 (d, J = 3.8 Hz, 3H), 1.41 (dd, J = 14.0, 7.6 Hz, 3H), 0.77-0.65 (m, 2H). |
| 14 | 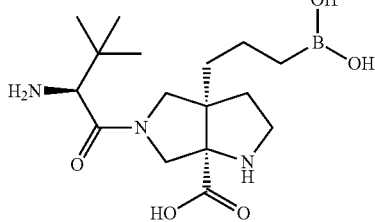 | 338 | 1H NMR (499 MHz, Deuterium Oxide) δ 4.33 (dd, J = 25.0, 13.7 Hz, 1H), 4.16-3.96 (m, 1H), 3.87-3.69 (m, 3H), 3.64-3.42 (m, 3H), 2.36-2.23 (m, 1H), 2.14-2.02 (m, 1H), 1.52-1.34 (m, 3H), 1.34-1.19 (m, 1H), 1.02 (d, J = 5.5 Hz, 9H), 0.89 (dt, J = 12.7, 6.4 Hz, 1H), 0.72 (t, J = 6.7 Hz, 2H). |
| 15 | 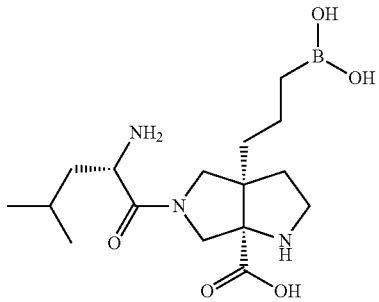 [SMILES: CC(C)C[C@H](N)C(=O)N1C[C@@]2(CCCB(O)O)CCN[C@@]2(C(=O)O)C1] | 338 | 1H NMR (499 MHz, Deuterium Oxide) δ 4.31-4.12 (m, 2H), 4.04 (dd, J = 12.7, 8.4 Hz, 1H), 3.85-3.71 (m, 1H), 3.71-3.59 (m, 1H), 3.57-3.47 (m, 1H), 3.47-3.36 (m, 1H), 2.29 (ddd, J = 13.7, 7.7, 5.8 Hz, 1H), 2.21-1.95 (m, 2H), 1.81-1.51 (m, 4H), 1.51-1.18 (m, 4H), 0.97-0.81 (m, 6H), 0.73 (d, J = 6.8 Hz, 2H). |
| 16 | 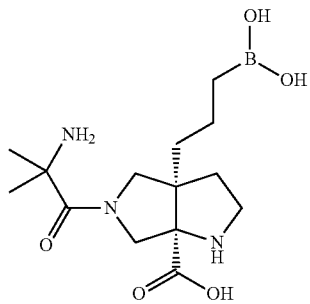 | 310 | 1H NMR (499 MHz, Deuterium Oxide) δ 4.16 (d, J = 12.9 Hz, 1H), 3.99-3.80 (m, 2H), 3.73-3.62 (m, 1H), 3.52 (d, J = 5.8 Hz, 1H), 3.44 (d, J = 7.2 Hz, 1H), 2.23 (s, 2H), 2.07 (s, 2H), 1.68-1.56 (m, 6H), 1.41 (d, J = 14.7 Hz, 3H), 1.33 (d, J = 7.7 Hz, 1H), 0.73 (t, J = 6.7 Hz, 2H). |

| Example | Structure | [M − H₂O + H]+. | NMR |
|---------|-----------|-----------------|-----|
| 17 | 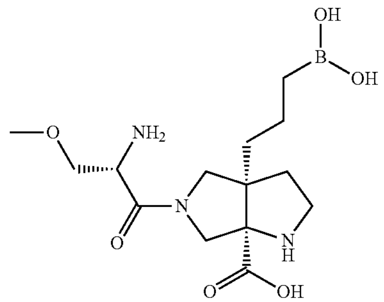 [SMILES: COC[C@H](N)C(=O)N1C[C@@]2(CCCB(O)O)CCN[C@@]2(C(=O)O)C1] | 326 | Note: LC-MS showed the compound is not very pure. NMR data cannot be interpreted |

Example 18: (3aR,6aR)-5-(L-alanyl)-3a-(3-((3aS,4S,6S,7aR)-3a,5,5-trimethylhexahydro-4,6-methanobenzo[d][1,3,2]dioxaborol-2-yl)propyl)hexahydropyrrolo[3,4-b]pyrrole-6a(1H)-carboxylic acid

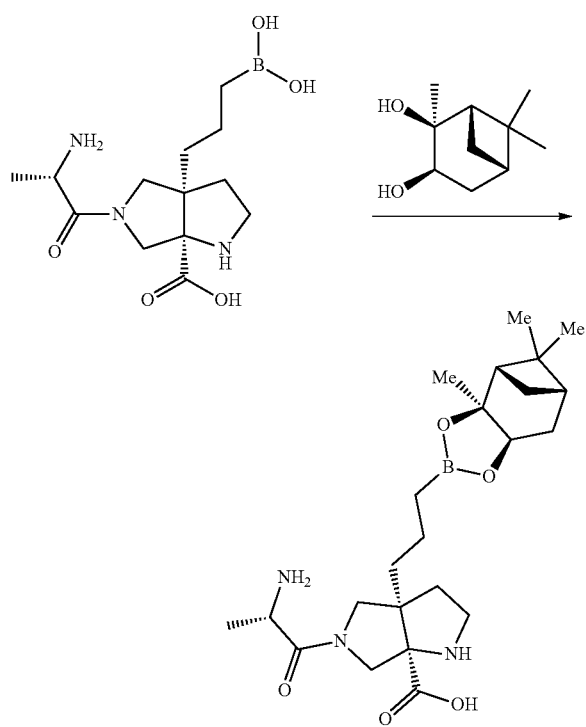

(1S,2S,3R,5S)-2,6,6-trimethylbicyclo[3.1.1]heptane-2,3-diol (0.98 g, 5.8 mmol) was added to a mixture of (3aR,6aR)-5-(L-alanyl)-3a-(3-boronopropyl)hexahydropyrrolo[3,4-b]pyrrole-6a(1H)-carboxylic acid (Example 1, 1.8 g, 5.8 mmol) in CH₃CN (58 mL). The reaction mixture was stirred at 85° C. overnight. The solvent was removed, and the residue was directly purified by mass-directed reverse phase chromatography (C18 column, water [0.1% TFA]-CH₃CN) to give (3aR,6aR)-5-(L-alanyl)-3a-(3-((3aS,4S,6S,7aR)-3a,5,5-trimethylhexahydro-4,6-methanobenzo[d][1,3,2]dioxaborol-2-yl)propyl)hexahydropyrrolo[3,4-b]pyrrole-6a(1H)-carboxylic acid as TFA salt. LCMS ($C_{23}H_{39}BN_3O_5^+$) (ES, m/z): 448 (M+H)⁺. ¹H NMR (499 MHz, DMSO-d₆) δ 4.28 (d, J=8.6 Hz, 1H), 3.98 (d, J=11.7 Hz, 0.5H), 3.89-3.79 (m, 1H), 3.66-3.44 (m, 3H), 3.28-3.20 (m, 1.5H), 3.10-3.03 (m, 1H), 2.35-2.24 (m, 1H), 2.22-2.08 (m, 1H), 1.97-1.75 (m, 4H), 1.74-1.65 (m, 1H), 1.58-1.43 (m, 1H), 1.32 (s, 3H), 1.30 (s, 3H), 1.25 (s, 3H), 1.14-1.11 (m, 4H), 1.02-0.96 (m, 1H), 0.82 (s, 3H), 0.76-0.57 (m, 2H).

Assay

Arginase Thioornithine Generating Assay (TOGA)

Compounds were serially diluted in ten 3-fold steps in DMSO starting from 10 mM DMSO stocks. Compound dilutions or DMSO alone were then dispensed from the dilution plate into a Greiner black 384-well assay plate (catalog #781086) using an Echo 555 acoustic liquid handler (Labcyte).

Arginase protein was recombinantly expressed in Escherichia coli. Purified protein was then diluted in assay buffer (50 mM Tris pH 7.5, 50 mM NaCl, 1 mM manganese chloride, 0.0500 bovine serum albumin to obtain a final Arginase concentration of 1.88 nM. Arginase solution (20 M)) or buffer alone (20 µL) were dispensed to wells of the assay plate using a BioRAPTR liquid dispenser (Beckman Coulter). Assay plates containing compound and arginase enzyme were incubated at room temperature for 30 minutes. Afterwards, 5 L of 2.5 mM thioarginine (Cayman Chemicals) in assay buffer were added to each well of the assay plate using a BioRAPTR liquid dispenser. Plates were incubated at room temperature for 60 minutes and reactions were quenched by addition of 15 µL of 200 uM 7-Diethylamine-3-(4-maleimidophenyl)-4-methyl coumarin (Sigma Chemical) in 70% ethanol. Plates were briefly shaken to mix and the fluorescence was measured in an Spectramax plate reader (Molecular Devices) with a 410 nm excitation wavelength and an 490 nm emission wavelength.

The fluorescence intensity of each well was corrected for the background observed in wells that did not receive arginase and was expressed as a fraction of the intensity observed in wells that received arginase enzyme and DMSO only. Potencies were calculated by linear least squares fit to the four parameter logistic IC50 equation.

| Example | TOGA IC₅₀ (nM) | Percent Inhibition at Top Dose | Top Dose (nM) |
|---------|----------------|-------------------------------|---------------|
| 1 | 14 | 99.73 | 10000 |
| 2 | 22 | 97.64 | 10000 |
| 3 | 1825 | 89.5 | 10000 |
| 4 | 46 | 98.18 | 10000 |
| 5 | 362 | 92.96 | 10000 |
| 6 | 98 | 91.89 | 10000 |
| 7 | 557 | 85.1 | 10000 |

| Example | TOGA IC$_{50}$ (nM) | Percent Inhibition at Top Dose | Top Dose (nM) |
|---|---|---|---|
| 8 | 8 | 99 | 10000 |
| 9 | 67 | 97.29 | 10000 |
| 10 | 26 | 96.63 | 10000 |
| 11 | 39 | 99.47 | 10000 |
| 12 | 34 | 100.5 | 10000 |
| 13 | 21 | 102 | 10000 |
| 14 | 45 | 101.8 | 10000 |
| 15 | 29 | 96.74 | 10000 |
| 16 | 81 | 97.28 | 10000 |
| 17 | 9 | 97.85 | 10000 |
| 18 | 136 | 97.91 | 10000. |

-continued
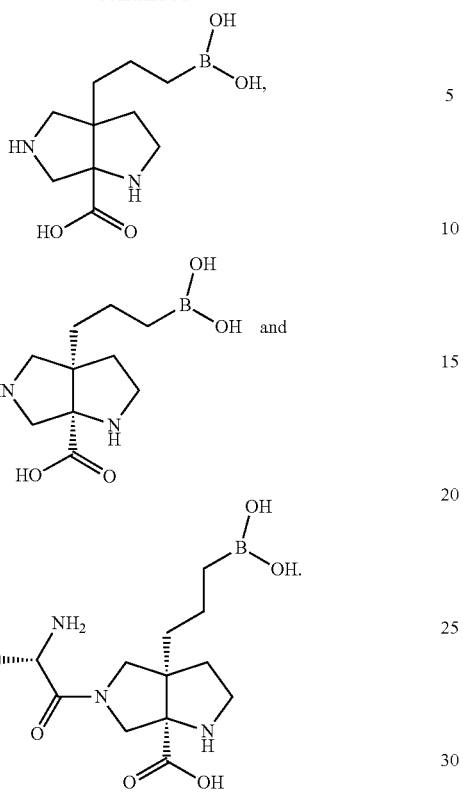

What is claimed:

1. A compound of Formula I:

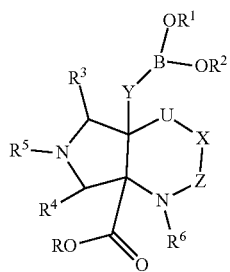

I or a pharmaceutically acceptable salt thereof, wherein:

Y is a straight or branched (C$_2$-C$_5$) alkylenyl, wherein one or more —CH$_2$— groups in Y are optionally and independently replaced with a moiety selected from the group consisting of O, S and NH;

U is CR$^7$R$^8$ or O;

X is a bond or CR$^9$R$^{10}$;

Z is a bond or CR$^{11}$R$^{12}$;

R is hydrogen, C$_1$-C$_6$alkyl, haloC$_1$-C$_6$alkyl, C$_1$-C$_6$alkylOH or C$_1$-C$_6$alkylOC$_1$-C$_6$alkyl;

R$^1$ is hydrogen, C$_3$-C$_6$cycloalkyl or C$_1$-C$_6$alkyl or, taken with R$^2$ forms a C$_3$-C$_8$cycloalkyl, wherein the C$_3$-C$_8$cycloalkyl is unsubstituted or substituted with one to four substituents selected from the group consisting of halogen, C$_1$-C$_6$alkyl, oxo and OH;

R$^2$ is hydrogen, C$_3$-C$_6$cycloalkyl or C$_1$-C$_6$alkyl or, taken with R$^1$ forms a C$_3$-C$_8$cycloalkyl, wherein the C$_3$-C$_8$cycloalkyl is unsubstituted or substituted with one to four substituents selected from the group consisting of halogen, C$_1$-C$_6$alkyl, oxo and OH;

R$^3$ is hydrogen, C$_1$-C$_6$alkyl, C$_3$-C$_6$cycloalkyl, haloC$_1$-C$_6$alkyl, C$_1$-C$_6$alkylOH, C$_1$-C$_6$alkylNH$_2$ or C$_1$-C$_6$alkylOC$_1$-C$_6$alkyl, or when taken with the carbon to which it is attached and the adjacent hydrogen forms C=O;

R$^4$ is hydrogen, C$_1$-C$_6$alkyl, C$_3$-C$_6$cycloalkyl, haloC$_1$-C$_6$alkyl, C$_1$-C$_6$alkylOH, or C$_1$-C$_6$alkylOC$_1$-C$_6$alkyl, or when taken with the carbon to which it is attached and the adjacent hydrogen forms C=O;

R$^5$ is hydrogen, C$_1$-C$_6$alkyl, C$_3$-C$_6$cycloalkyl, haloC$_1$-C$_6$alkyl, C$_1$-C$_6$alkylOH, C$_1$-C$_6$alkylNH$_2$;

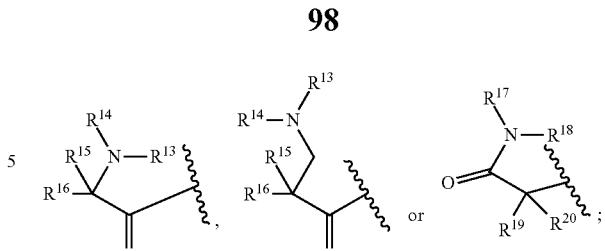

R$^6$ is hydrogen, C$_1$-C$_6$alkyl, C$_3$-C$_6$cycloalkyl, haloC$_1$-C$_6$alkyl, C$_1$-C$_6$alkylOH or C$_1$-C$_6$alkylOC$_1$-C$_6$alkyl;

R$^7$ is hydrogen, C$_1$-C$_6$alkyl, C$_3$-C$_6$cycloalkyl, haloC$_1$-C$_6$alkyl, OH, C$_1$-C$_6$alkylOH, NH$_2$, or C$_1$-C$_6$alkylOC$_1$-C$_6$alkyl, or when taken with R$^8$ forms =O;

R$^8$ is hydrogen, C$_1$-C$_6$alkyl, C$_3$-C$_6$cycloalkyl, haloC$_1$-C$_6$alkyl, OH, C$_1$-C$_6$alkylOH, NH$_2$, or C$_1$-C$_6$alkylOC$_1$-C$_6$alkyl, or when taken with R$^7$ forms =O;

R$^9$ is hydrogen, C$_1$-C$_6$alkyl, C$_3$-C$_6$cycloalkyl, haloC$_1$-C$_6$alkyl, OH, C$_1$-C$_6$alkylOH, C$_1$-C$_6$alkylN(R$^{23}$)(R$^{24}$) or C$_1$-C$_6$alkylOC$_1$-C$_6$alkyl, or when taken with R$^{10}$ forms =O;

R$^{10}$ is hydrogen, C$_1$-C$_6$alkyl, C$_3$-C$_6$cycloalkyl, haloC$_1$-C$_6$alkyl, OH, C$_1$-C$_6$alkylOH, C$_1$-C$_6$alkylN(R$^{23}$)(R$^{24}$) or C$_1$-C$_6$alkylOC$_1$-C$_6$alkyl, or when taken with R$^9$ forms =O;

R$^{11}$ is hydrogen, C$_1$-C$_6$alkyl, C$_3$-C$_6$cycloalkyl, haloC$_1$-C$_6$alkyl, C$_1$-C$_6$alkylOH, C$_1$-C$_6$alkylN(R$^{23}$)(R$^{24}$) or C$_1$-C$_6$alkylOC$_1$-C$_6$alkyl, or when taken with R$^{12}$ forms =O;

R$^{12}$ is hydrogen, C$_1$-C$_6$alkyl, C$_3$-C$_6$cycloalkyl, haloC$_1$-C$_6$alkyl, C$_1$-C$_6$alkylOH, C$_1$-C$_6$alkylN(R$^{23}$)(R$^{24}$) or C$_1$-C$_6$alkylOC$_1$-C$_6$alkyl, or when taken with R$^{11}$ forms =O;

R$^{13}$ is hydrogen, C$_1$-C$_6$alkyl, C$_3$-C$_6$cycloalkyl, haloC$_1$-C$_6$alkyl, C$_1$-C$_6$alkylOH, COC$_1$-C$_6$alkylN(R$^{21}$)(R$^{22}$), or C$_1$-C$_6$alkylOC$_1$-C$_6$alkyl or when taken with R$^{14}$ forms a nitrogen containing heterocycle or when taken with R$^{15}$ or R$^{16}$ forms a nitrogen containing heteroaryl or heterocycle;

R$^{14}$ is hydrogen, C$_1$-C$_6$alkyl, C$_3$-C$_6$cycloalkyl, haloC$_1$-C$_6$alkyl, C$_1$-C$_6$alkylOH, COC$_1$-C$_6$alkylN(R$^{21}$)(R$^{22}$), or C$_1$-C$_6$alkylOC$_1$-C$_6$alkyl or when taken with R$^{13}$ forms a nitrogen containing heterocycle or when taken with R$^{15}$ or R$^{16}$ forms a nitrogen containing heteroaryl or heterocycle;

R$^{15}$ is hydrogen, C$_1$-C$_6$alkyl, C$_3$-C$_6$cycloalkyl, haloC$_1$-C$_6$alkyl, C$_1$-C$_6$alkylOH, C$_1$-C$_6$alkylN(R$^{21}$)(R$^{22}$), C$_1$-C$_6$alkylCOOR$^{21}$, C$_1$-C$_6$alkylCON(R$^{21}$)(R$^{22}$), C$_1$-C$_6$alkylSH, C$_1$-C$_6$alkylSC$_1$-C$_6$alkyl or C$_1$-C$_6$alkylOC$_1$-C$_6$alkyl, C$_1$-C$_6$alkylaryl, C$_1$-C$_6$alkylheteroaryl, C$_1$-C$_6$alkylheterocycle or when taken with R$^{13}$ or R$^{14}$ forms a nitrogen containing heterocycle, or when taken with R$^{16}$ forms a C$_3$-C$_7$cycloalkyl or heterocycle;

R$^{16}$ is hydrogen, C$_1$-C$_6$alkyl, C$_3$-C$_6$cycloalkyl, haloC$_1$-C$_6$alkyl, C$_1$-C$_6$alkylOH, C$_1$-C$_6$alkylN(R$^{21}$)(R$^{22}$), C$_1$-C$_6$alkylCOOR$^{21}$, C$_1$-C$_6$alkylCON(R$^{21}$)(R$^{22}$), C$_1$-C$_6$alkylSH, C$_1$-C$_6$alkylSC$_1$-C$_6$alkyl or C$_1$-C$_6$alkylOC$_1$-C$_6$alkyl, C$_1$-C$_6$alkylaryl, C$_1$-C$_6$alkylheteroaryl, C$_1$-C$_6$alkylheterocycle or when taken with R$^{13}$ or R$^{14}$ forms a nitrogen containing heterocycle, or when taken with R$^{15}$ forms a C$_3$-C$_7$cycloalkyl or heterocycle;

R$^{17}$ is hydrogen, C$_1$-C$_6$alkyl, C$_3$-C$_6$cycloalkyl, haloC$_1$-C$_6$alkyl, OH, C$_1$-C$_6$alkylOH, or C$_1$-C$_6$alkylOC$_1$-C$_6$alkyl or when taken with R$^{18}$ forms a nitrogen containing heterocycle;

$R^{18}$ is hydrogen, $C_1$-$C_6$alkyl, $C_3$-$C_6$cycloalkyl, halo$C_1$-$C_6$alkyl, OH, $C_1$-$C_6$alkylOH, or $C_1$-$C_6$alkylOC$_1$-$C_6$alkyl or when taken with $R^{17}$ forms a nitrogen containing heterocycle;

$R^{19}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylS $C_1$-$C_6$alkyl or $C_1$-$C_6$alkylOC$_1$-$C_6$alkyl;

$R^{20}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylS $C_1$-$C_6$alkyl or $C_1$-$C_6$alkylOC$_1$-$C_6$alkyl;

each occurrence of $R^{21}$ is independently selected from the group consisting of hydrogen, $C_1$-$C_6$alkyl and $C_3$-$C_6$cycloalkyl;

each occurrence of $R^{22}$ is independently selected from the group consisting of hydrogen, $C_1$-$C_6$alkyl and $C_3$-$C_6$cycloalkyl;

each occurrence of $R^{23}$ is independently selected from the group consisting of hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylN($R^{21}$)($R^{22}$), $C_1$-$C_6$alkylCOOR$^{21}$, $C_1$-$C_6$alkylCON($R^{21}$)($R^{22}$), $C_1$-$C_6$alkylSH, $C_1$-$C_6$alkylSC$_1$-$C_6$alkyl, $C_1$-$C_6$alkylOC$_1$-$C_6$alkyl, $C_1$-$C_6$alkylaryl, $C_1$-$C_6$alkylheteroaryl or $C_1$-$C_6$alkylheterocycle; and each occurrence of $R^{24}$ is independently selected from the group consisting of hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylN($R^{21}$)($R^{22}$), $C_1$-$C_6$alkylCOOR$^{21}$, $C_1$-$C_6$alkylCON($R^{21}$)($R^{22}$), $C_1$-$C_6$alkylSH, $C_1$-$C_6$alkylSC$_1$-$C_6$alkyl, $C_1$-$C_6$alkylOC$_1$-$C_6$alkyl, $C_1$-$C_6$alkylaryl, $C_1$-$C_6$alkylheteroaryl or $C_1$-$C_6$alkylheterocycle.

2. The compound of claim 1, or a pharmaceutically acceptable salt thereof, wherein $R^1$ and $R^2$ are both hydrogen.

3. The compound of claim 1, or a pharmaceutically acceptable salt thereof, wherein Y is propylenyl.

4. The compound of claim 1, or a pharmaceutically acceptable salt thereof, wherein $R^3$ is hydrogen, CH$_2$NH$_2$ or methyl.

5. The compound of claim 1, or a pharmaceutically acceptable salt thereof, wherein $R^4$ is hydrogen.

6. The compound of claim 1, or a pharmaceutically acceptable salt thereof, wherein X is a bond.

7. The compound of claim 1, or a pharmaceutically acceptable salt thereof, wherein Z is a bond.

8. The compound of claim 1, or a pharmaceutically acceptable salt thereof, wherein X is CR$^9$R$^{10}$ and Z is a bond.

9. The compound of claim 8, or a pharmaceutically acceptable salt thereof, wherein $R^9$ is hydrogen.

10. The compound of claim 8, or a pharmaceutically acceptable salt thereof, wherein $R^{10}$ is hydrogen, ethanol or methyl.

11. The compound of claim 1, or a pharmaceutically acceptable salt thereof, wherein $R^6$ is hydrogen.

12. The compound of claim 1, or a pharmaceutically acceptable salt thereof, wherein $R^5$ is hydrogen.

13. The compound of claim 1, or a pharmaceutically acceptable salt thereof, wherein $R^5$ is $C_1$-$C_6$alkyl.

14. The compound of claim 1, or a pharmaceutically acceptable salt thereof, wherein $R^5$ is methyl.

15. The compound of claim 1, or a pharmaceutically acceptable salt thereof, wherein $R^5$ is

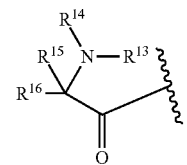

wherein,
$R^{13}$ is hydrogen, $C_1$-$C_6$alkyl, $C_3$-$C_6$cycloalkyl, halo$C_1$-$C_6$alkyl, $C_1$-$C_6$alkylOH, COC$_1$-$C_6$alkylN($R^{21}$)($R^{22}$), or $C_1$-$C_6$alkylOC$_1$-$C_6$alkyl or when taken with $R^{14}$ forms a nitrogen containing heterocycle or when taken with $R^{15}$ or $R^{16}$ forms a nitrogen containing heteroaryl or heterocycle;

$R^{14}$ is hydrogen, $C_1$-$C_6$alkyl, $C_3$-$C_6$cycloalkyl, halo$C_1$-$C_6$alkyl, $C_1$-$C_6$alkylOH, COC$_1$-$C_6$alkylN($R^{21}$)($R^{22}$), or $C_1$-$C_6$alkylOC$_1$-$C_6$alkyl or when taken with $R^{13}$ forms a nitrogen containing heterocycle or when taken with $R^{15}$ or $R^{16}$ forms a nitrogen containing heteroaryl or heterocycle;

$R^{15}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylN($R^{21}$)($R^{22}$), $C_1$-$C_6$alkylCOOR$^{21}$, $C_1$-$C_6$alkylCON($R^{21}$)($R^{22}$), $C_1$-$C_6$alkylSH, $C_1$-$C_6$alkylSC$_1$-$C_6$alkyl or $C_1$-$C_6$alkylOC$_1$-$C_6$alkyl, $C_1$-$C_6$alkylaryl, $C_1$-$C_6$alkylheteroaryl, $C_1$-$C_6$alkylheterocycle or when taken with $R^{13}$ or $R^{14}$ forms a nitrogen containing heterocycle, or when taken with $R^{16}$ forms a $C_3$-$C_7$cycloalkyl or heterocycle;

$R^{16}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylN($R^{21}$)($R^{22}$), $C_1$-$C_6$alkylCOOR$^{21}$, $C_1$-$C_6$alkylCON($R^{21}$)($R^{22}$), $C_1$-$C_6$alkylSH, $C_1$-$C_6$alkylSC$_1$-$C_6$alkyl or $C_1$-$C_6$alkylOC$_1$-$C_6$alkyl, $C_1$-$C_6$alkylaryl, $C_1$-$C_6$alkylheteroaryl, $C_1$-$C_6$alkylheterocycle or when taken with $R^{13}$ or $R^{14}$ forms a nitrogen containing heterocycle, or when taken with $R^{15}$ forms a $C_3$-$C_7$cycloalkyl or heterocycle; and each occurrence of $R^{22}$ is independently selected from the group consisting of hydrogen, $C_1$-$C_6$alkyl and $C_3$-$C_6$cycloalkyl.

16. The compound of claim 1, or a pharmaceutically acceptable salt thereof, wherein $R^5$ is

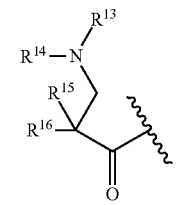

wherein,
$R^{13}$ is hydrogen, $C_1$-$C_6$alkyl, $C_3$-$C_6$cycloalkyl, halo$C_1$-$C_6$alkyl, $C_1$-$C_6$alkylOH, COC$_1$-$C_6$alkylN($R^{21}$)($R^{22}$), or $C_1$-$C_6$alkylOC$_1$-$C_6$alkyl or when taken with $R^{14}$ forms a nitrogen containing heterocycle or when taken with $R^{15}$ or $R^{16}$ forms a nitrogen containing heteroaryl or heterocycle;

$R^{14}$ is hydrogen, $C_1$-$C_6$alkyl, $C_3$-$C_6$cycloalkyl, halo$C_1$-$C_6$alkyl, $C_1$-$C_6$alkylOH, COC$_1$-$C_6$alkylN($R^{21}$)($R^{22}$), or $C_1$-$C_6$alkylOC$_1$-$C_6$alkyl or when taken with $R^{13}$ forms a nitrogen containing heterocycle or when taken with $R^{15}$ or $R^{16}$ forms a nitrogen containing heteroaryl or heterocycle;

$R^{15}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylN($R^{21}$)($R^{22}$), $C_1$-$C_6$alkylCOOR$^{21}$, $C_1$-$C_6$alkylCON($R^{21}$)($R^{22}$), $C_1$-$C_6$alkylSH, $C_1$-$C_6$alkylSC$_1$-$C_6$alkyl or $C_1$-$C_6$alkylOC$_1$-$C_6$alkyl, $C_1$-$C_6$alkylaryl, $C_1$-$C_6$alkylheteroaryl, $C_1$-$C_6$alkylheterocycle or when taken with $R^{13}$ or $R^{14}$ forms a nitrogen containing heterocycle, or when taken with $R^{16}$ forms a $C_3$-$C_7$cycloalkyl or heterocycle;

$R^{16}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylN($R^{21}$)($R^{22}$), $C_1$-$C_6$alkylCOOR$^{21}$, $C_1$-$C_6$alkylCON($R^{21}$)($R^{22}$), $C_1$-$C_6$alkylSH, $C_1$-$C_6$alkylSC$_1$-$C_6$alkyl or $C_1$-$C_6$alkylOC$_1$-$C_6$alkyl, $C_1$-$C_6$alkylaryl, $C_1$-$C_6$alkylheteroaryl, $C_1$-$C_6$alkylheterocycle or when taken with $R^{13}$ or $R^{14}$ forms a nitrogen containing heterocycle, or when taken with $R^{15}$ forms a $C_3$-$C_7$cycloalkyl or heterocycle; and each occurrence of $R^{22}$ is independently selected from the group consisting of hydrogen, $C_1$-$C_6$alkyl and $C_3$-$C_6$cycloalkyl.

17. The compound of claim 1, or a pharmaceutically acceptable salt thereof, wherein $R^5$ is

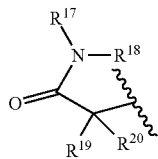

wherein, $R^{17}$ is hydrogen, $C_1$-$C_6$alkyl, $C_3$-$C_6$cycloalkyl, halo$C_1$-$C_6$alkyl, OH, $C_1$-$C_6$alkylOH, or $C_1$-$C_6$alkylOC$_1$-$C_6$alkyl or when taken with $R^{18}$ forms a nitrogen containing heterocycle;

$R^{18}$ is hydrogen, $C_1$-$C_6$alkyl, $C_3$-$C_6$cycloalkyl, halo$C_1$-$C_6$alkyl, OH, $C_1$-$C_6$alkylOH, or $C_1$-$C_6$alkylOC$_1$-$C_6$alkyl or when taken with $R^{17}$ forms a nitrogen containing heterocycle;

$R^{19}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylS $C_1$-$C_6$alkyl or $C_1$-$C_6$alkylOC$_1$-$C_6$alkyl; and $R^{20}$ is hydrogen, $C_1$-$C_6$alkyl, $C_3$-$C_6$cycloalkyl, halo$C_1$-$C_6$alkyl, $C_1$-$C_6$alkylOH, $C_1$-$C_6$alkylS $C_1$-$C_6$alkyl or $C_1$-$C_6$alkylOC$_1$-$C_6$alkyl.

18. A compound, or pharmaceutically acceptable salt thereof, selected from the group consisting of:

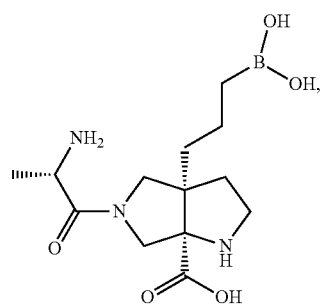

-continued

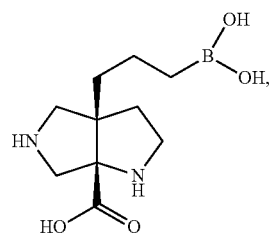

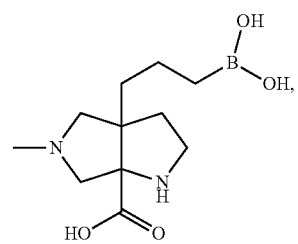

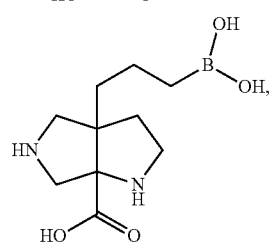

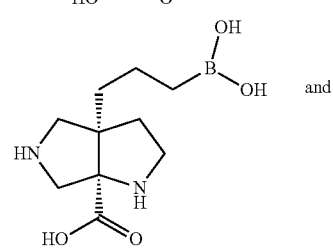

and

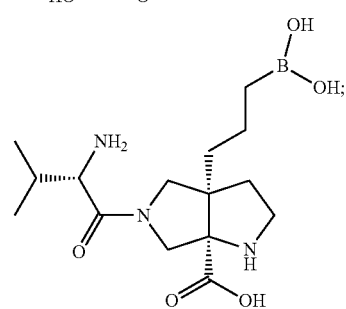

or a pharmaceutically acceptable salt thereof.

19. A compound selected from the group consisting of:

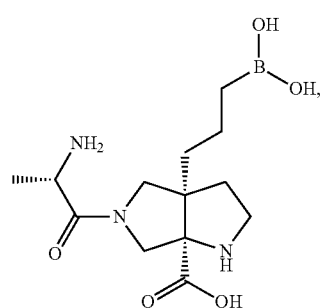

103
-continued
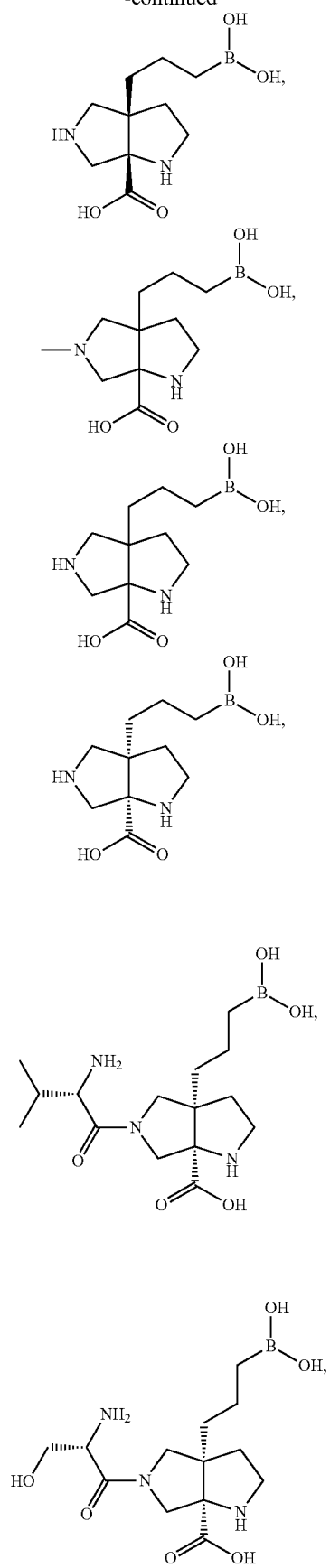
104
-continued
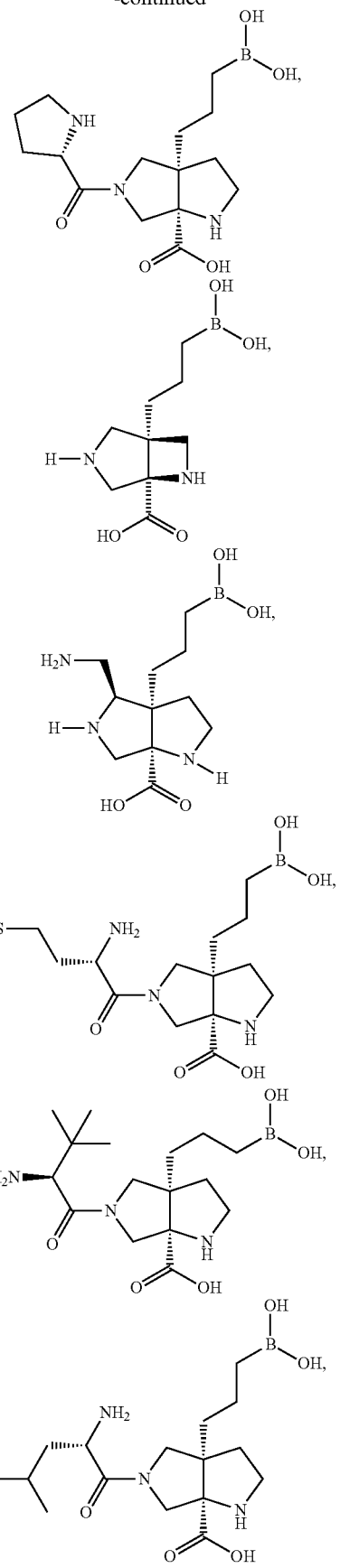

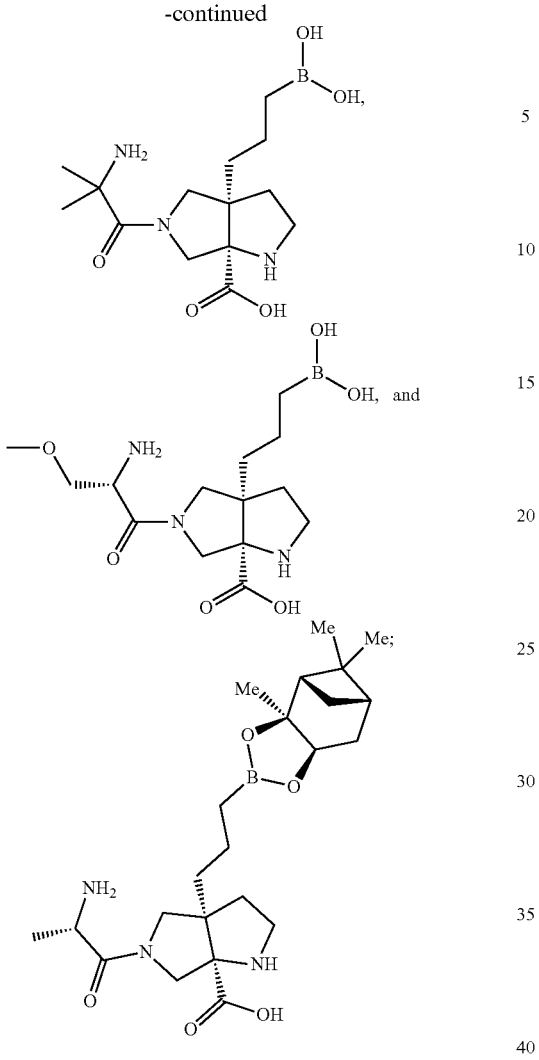

or a pharmaceutically acceptable salt thereof.

20. A method of treating cancer comprising administering to a patient in need thereof a compound or pharmaceutically acceptable salt of claim 1, wherein the cancer is selected from the group consisting of renal cell carcinoma, prostate cancer, colorectal, breast cancer, skin cancer, lung cancer, ovarian cancer, and gastric cancer.

21. A pharmaceutical composition comprising a compound or a pharmaceutically acceptable salt of claim 1 and a pharmaceutically acceptable carrier.

22. A compound selected from the group consisting of:

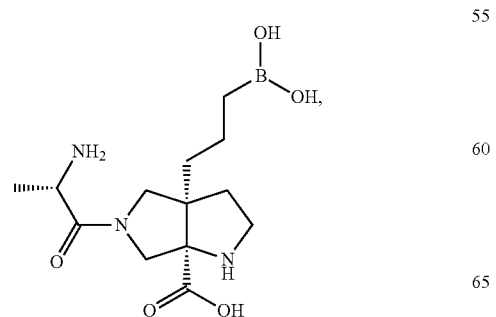

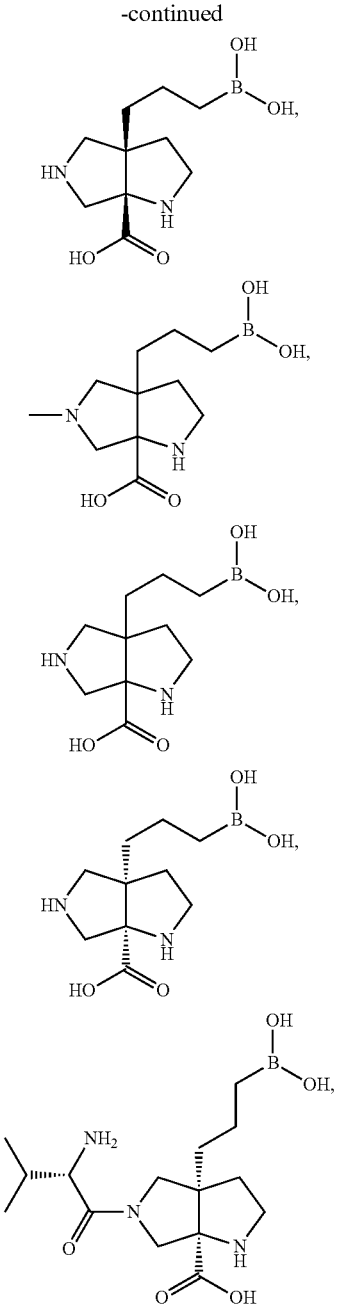

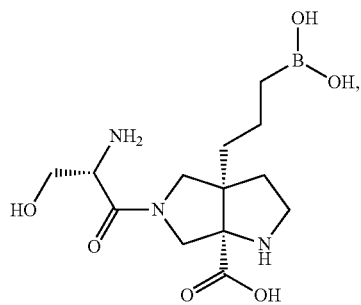

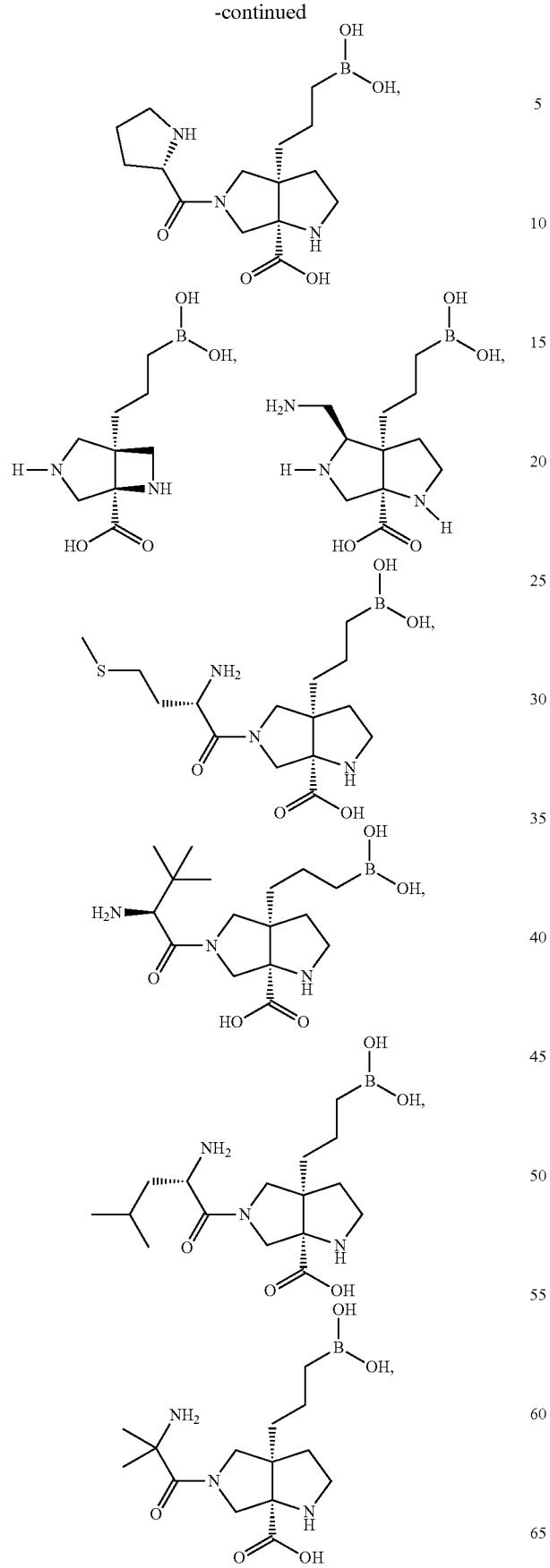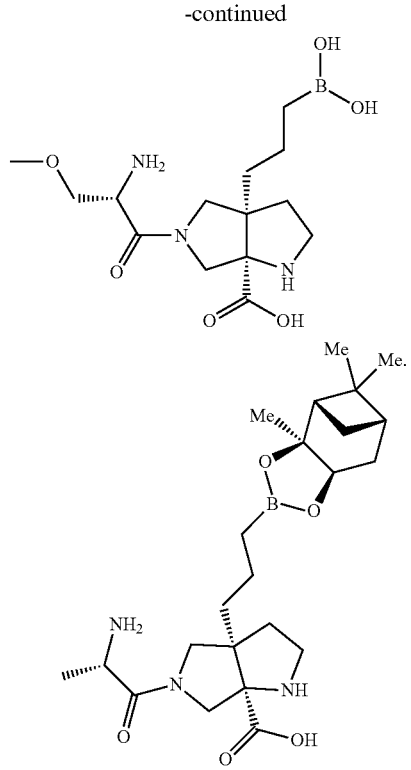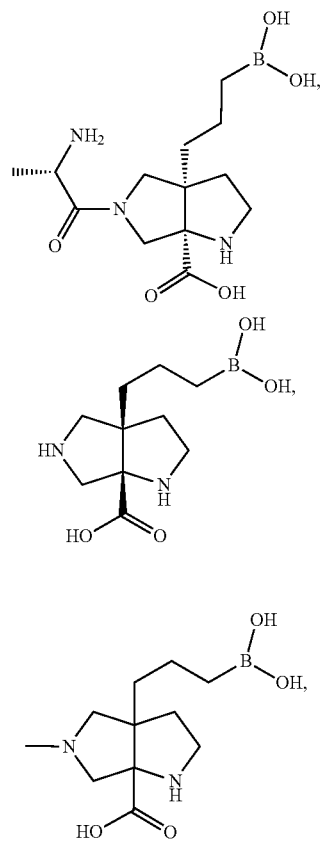
23. A compound selected from the group consisting of: